United States Patent
Navalgund et al.

(10) Patent No.: US 11,826,170 B2
(45) Date of Patent: Nov. 28, 2023

(54) ARTIFICIAL INTELLIGENCE MODELS FOR WIRELESS PATCH DATA ACQUISITION FOR GASTROINTESTINAL ELECTRODIAGNOSTICS

(71) Applicant: G-TECH MEDICAL, INC., Mountain View, CA (US)

(72) Inventors: Anand Navalgund, San Jose, CA (US); Steve Axelrod, Los Altos, CA (US); Lindsay Axelrod, Los Altos, CA (US)

(73) Assignee: G-Tech Medical, Inc., Mountain View, CA (US)

( * ) Notice: Subject to any disclaimer, the term of this patent is extended or adjusted under 35 U.S.C. 154(b) by 770 days.

(21) Appl. No.: 16/708,288

(22) Filed: Dec. 9, 2019

(65) Prior Publication Data
US 2020/0107781 A1 Apr. 9, 2020

Related U.S. Application Data

(63) Continuation-in-part of application No. 15/919,578, filed on Mar. 13, 2018, now Pat. No. 10,499,829,
(Continued)

(51) Int. Cl.
*A61B 5/392* (2021.01)
*A61B 5/00* (2006.01)
*A61B 5/296* (2021.01)

(52) U.S. Cl.
CPC .......... *A61B 5/6823* (2013.01); *A61B 5/0004* (2013.01); *A61B 5/296* (2021.01); *A61B 5/392* (2021.01)

(58) Field of Classification Search
CPC ....... A61B 5/6823; A61B 5/296; A61B 5/392; A61B 5/0004
See application file for complete search history.

(56) References Cited

U.S. PATENT DOCUMENTS 5,704,368 A 1/1998 Asano et al.
5,709,213 A * 1/1998 Kruse .................... A61B 5/327
600/509
(Continued)

FOREIGN PATENT DOCUMENTS

NO 2010068818 A2 6/2010
WO 199610358 A1 4/1996
(Continued)

OTHER PUBLICATIONS

Daniel, E. E., Chapman, K.M. Electrical activity of the gastrointestinal tract as an indication of mechanical activity. Digest Dis Sci 8, 54-102 (1963). (Year: 1963).
(Continued)

*Primary Examiner* — Daniel L Cerioni
(74) *Attorney, Agent, or Firm* — Aurora Consulting LLC; Kristen J. Hansen; Ashley Sloat

(57) ABSTRACT

Systems and methods for analyzing electrical activity in smooth muscle of the gastrointestinal tract of a patient are disclosed. The systems includes an electromyographic-sensing patch adapted for placement on the skin of the abdomen of the patient. The patch has at least one bipolar electrode pair, or a multitude arranged in an array, and is enabled for communication of a signal indicative of a sensed electromyographic signal. The methods include artifact removal, data normalization, and peak detection methods on data derived from the sensed electromyographic signal and employ, at least for example, machine learning methods.

21 Claims, 58 Drawing Sheets

Related U.S. Application Data which is a continuation of application No. 14/051,440, filed on Oct. 10, 2013, now Pat. No. 9,943,264, application No. 16/708,288 is a continuation-in-part of application No. 16/692,550, which is a continuation of application No. 15/518,929, filed as application No. PCT/US2015/056282 on Oct. 19, 2015, now Pat. No. 10,485,444.

(60) Provisional application No. 62/065,226, filed on Oct. 17, 2014, provisional application No. 62/065,235, filed on Oct. 17, 2014, provisional application No. 62/065,216, filed on Oct. 17, 2014, provisional application No. 61/712,100, filed on Oct. 10, 2012.

(56) References Cited

U.S. PATENT DOCUMENTS

| | | | |
|---|---|---|---|
| 5,795,304 | A | 8/1998 | Sun et al. |
| 5,857,980 | A | 1/1999 | Wilson |
| 6,351,665 | B1 | 2/2002 | Koch |
| 7,160,254 | B2 | 1/2007 | Noar |
| 7,593,768 | B1 | 9/2009 | Vasilev et al. |
| 9,943,264 | B2 | 4/2018 | Axelrod et al. |
| 9,955,914 | B2 | 5/2018 | Dunki-Jacobs et al. |
| 2003/0069714 | A1 | 4/2003 | Wigley et al. |
| 2004/0260164 | A1 | 12/2004 | Kilcoyne et al. |
| 2005/0075578 | A1 | 4/2005 | Gharib et al. |
| 2005/0209709 | A1 | 9/2005 | Bradshaw |
| 2005/0215917 | A1 | 9/2005 | Noar |
| 2006/0058606 | A1 | 3/2006 | Davis et al. |
| 2006/0107954 | A1 | 5/2006 | Katz et al. |
| 2006/0149541 | A1 | 7/2006 | Jaklitsch et al. |
| 2006/0258927 | A1 | 11/2006 | Edgar, Jr. et al. |
| 2007/0150007 | A1 | 6/2007 | Anderson et al. |
| 2007/0167859 | A1 | 7/2007 | Finneran |
| 2007/0225576 | A1 | 9/2007 | Brown et al. |
| 2007/0276270 | A1 | 11/2007 | Tran |
| 2007/0287931 | A1 | 12/2007 | Dilorenz |
| 2008/0154110 | A1 | 6/2008 | Burnes et al. |
| 2008/0281312 | A1 | 11/2008 | Werneth et al. |
| 2009/0076565 | A1* | 3/2009 | Surwit ............... A61N 1/36007 607/144 |
| 2009/0318783 | A1 | 12/2009 | Rohde et al. |
| 2010/0172839 | A1 | 7/2010 | Walker |
| 2010/0228105 | A1 | 9/2010 | Policker et al. |
| 2010/0292606 | A1 | 11/2010 | Prakash et al. |
| 2011/0134820 | A1 | 6/2011 | Young |
| 2011/0306862 | A1* | 12/2011 | Hayes-Gill .......... A61B 5/4362 600/382 |
| 2012/0209102 | A1 | 8/2012 | Ylotalo et al. |
| 2013/0046150 | A1 | 2/2013 | Devanaboyina |
| 2013/0158476 | A1* | 6/2013 | Olson .................... A61B 34/30 604/95.01 |
| 2013/0073002 | A1 | 11/2013 | Paul |
| 2014/0206976 | A1 | 7/2014 | Thompson et al. |
| 2014/0226158 | A1 | 8/2014 | Trainer |
| 2014/0275886 | A1 | 9/2014 | Teixeira |
| 2014/0378963 | A1* | 12/2014 | Batchelor .......... A61B 18/1477 606/41 |
| 2015/0250445 | A1 | 9/2015 | William |
| 2016/0045133 | A1* | 2/2016 | Balachandran ........ A61B 5/349 600/509 |
| 2016/0103967 | A1 | 4/2016 | Bulut et al. |
| 2016/0121111 | A1 | 5/2016 | Levine et al. |
| 2016/0296157 | A1 | 10/2016 | Girouard |
| 2017/0231521 | A1* | 8/2017 | Axelrod ................ A61B 5/392 600/546 |
| 2018/0317800 | A1* | 11/2018 | Coleman ................ A61B 5/296 |

FOREIGN PATENT DOCUMENTS

| | | | |
|---|---|---|---|
| WO | 0067637 | A1 | 11/2000 |
| WO | 2010121038 | A1 | 10/2010 |
| WO | 2012060874 | A2 | 5/2012 |

OTHER PUBLICATIONS

Brown, B. H. et al.; "Intestinal smooth muscle electrical potentials recorded from surface electrodes"; Medical and Biological Engineering; Jan. 1975; p. 97-103. (Year: 1975).
Norali, A. M., et al., article entitled "Surface Electromyography Signal Processing and Application: A Review"; Proceedings of the International Conference on Man-Machine Systems (ICoMMS), Oct. 11-13, 2009; Batu Ferringhi, Penang, Malaysia, p. 1A4-1 to 1A4-9, (Year: 2009).
Verhagen, M.A.M.T., article entitled "Electrogastrography.," Clinical Autonomic Research, 15.6 (2005), p. 364-367 (Year: 2005).
Velcro® Brand Trademark Guidelines 2021, p. 1-8 (Year: 2021).
Chen, J.; article entitled "A computerized data analysis system for electrogastrogram," Computers in Biology and Medicine, vol. 22, Issues 1-2, 1992, p. 45-57, Pergamon Press (Year: 1992).
Alvarez, W. C., "The Electrogastrogram and what it shows," JAMA, Apr. 15, 1992, vol. 72, p. 1116-1119 (Year: 1922).
Darwish, A. et al., article entitled "Wearable and implantable wireless sensor network solutions for healthcare monitoring," Sensors 2011, May 26, 2011, p. 5561-5595 (2011) (Year: 2011).
Youn, W. et al., "Development of a compact-size and wireless surface EMG measurement system," ICROS-SICE International Joint Conference 2009, Aug. 18-21, 2009, Fukuoka International Congress Center, Japan, p. 1625-1628, IEEE (Year: 2009).
Ohyama, M. et al., article entitled "Active Wireless Electrodes for Surface Electromyography," 18th Annual International Conference of the IEEE Engineering in Medicine and Biology Society, Amsterdam 1996 1.7.2: Telemetry II, p. 295-296 (Year: 1996).
Lindberg, G. et al.; article entitled "24-Hour ambulator electrogastrography in healthy volunteers," Scand J Gastroenterol 31:658-664 (Year: 1996).
European Search Report dated Sep. 6, 2021, Reference P003264PC(EP)01.
Haddab, S. et al., "Microcontroller-Based System for Electrogastrography Monitoring Through Wireless Transmission," Measurement Science Review, 2009,p. 122-126, vol. 9, No. 5.
Chen, J. D. Z. et al., "Detection of gastric slow wave propagation from the cutaneous electrogastrogram," Am J Physiol, 1999, p. G424-G430 vol. 277.
Kim, D. W. et al., "Usefulness of a Developed Four-Channel EGG System with running spectrum analysis," Yonsei Medical Journal, 2000, p. 230-236, vol. 41. No. 2.
Garcia-Casado, J. et al., "Noninvasive Measurement and Analysis of Intestinal Myoelectrical Activity Using Surface Electrodes," IEEE Transactions on Biomedical Engineering, Jun. 2005, p. 983-991, vol. 52, No. 6.
Chen, J. D. Z. et al., "Measurement of Electrical Activity of the Human Small Intestine Using Surface Electrodes," IEEE Transactions on Biomedical Engineering, Jun. 1993, p. 598-602, vol. 40, No. 6.
Lammers, W. J. E. P et al., "Orgin and propagation of the slow wave in the canine stomach: the outlines of a gastric conduction system," Am J Physiol Gastrointest Liver Physiol, 2009, p. G1200-G1210, vol. 296.
Leahy, A. et al., "Abnormalities of the Electrogastrogram in Functional Gastrointestinal Disorders," American Journal of Gastroenterology, 1999, p. 1023-1028, vol. 94, No. 4.
Myers, T. J. et al., "Human Surface Electrogastrograms: AC and DC measurements," Annals of Biomedical Engineering, 1984, p. 319-333, vol. 12.
Wang, Z. S. et al., "Detection of gastric slow wave uncoupling from multi-channel electrogastrogram: validations and applications," Neurogastroenterol Motil, 2003, p. 457-465, vol. 15.
Written Opinion issued on PCT Application Serial No. PCT/US2011/01848 by ISA/US dated May 21, 2012, p. 1-5.
International Search Report issued on PCT Application Serial No. PCT/US2011/01848 by ISA/US dated May 21, 2012, p. 1-4.
Madsen et al., "Listening to Bowel Sounds: An Evidence-Based Practice Project," Dec. 2005, AJN, vol. 105, No. 12, p. 40-48.
"Home—ePatch," DELTA Danish Electronics, Light & Acoustics, [Accessed Jul. 1, 2016] <http://epatch.madebydelta.com>.

(56) References Cited

OTHER PUBLICATIONS

Haahr, R. et al., "A wearable 'electronic patch' for wireless continuous monitoring of chronically diseased patients," 5th International Summer School and Symposium on Medical Devices and Biosensors, 2008, p. 66-70.

Sanders, K. M. et al., "Interstitial cells of Cajal as pacemakers in the gastrointestinal tract," Annu Rev Physiol, 2006, p. 307-343, vol. 68.

International Search Report and Written Opinion issued for PCT/US2015/056282 by ISA/US dated Jan. 20, 2016 (9 pages).

Armstrong, S. "Wireless connectivity for health and sports monitoring: a review"; British Journal of Sports Medicine 2007; 41:285-289. (Year: 2007).

Patel et al.; "A review of wearable sensors and systems with application in rehabilitation". Journal of NeuroEngineering and Rehabilitation 2012 9:21; p. 1-17 (Year: 2012).

Kaneoke, Y. et al.; "Gastrointestinal dysfunction in Parkinson's disease detected by Electrogastroenterography"; Journal of the Autonomic Nervous System 50 (1995) 275-281. (Year: 1995).

Reddy, S. N. et al.; "Frequency analysis of gut EMG"; CRC Critical reviews in biomedical Engineering; vol. 15; issue 2 (1987) p. 95-116. (Year: 1987).

Code, C. et al; "The inter-digestive myoelectric complex of the stomach and small bowel of dogs"; J. Physiol. (1975), 246, pp. 289-309. (Year: 1975).

Biopac Systems, Inc, "Bipolar EEG" website page; 1 page.

De Luca et al., "Inter-electrode spacing of surface EMG sensors: Reduction of crosstalk contamination during voluntary contractions," Journal of Biomechanics (2011), doi: 10.1016/j.jbiomech 2011.11.010; 7 pages.

Puurtinen et al., "Best Electrode Locations for a Small Bipolar ECG Device: Signal Strength Analysis of Clinical Data," Annuals of Biomedical Engineering, vol. 37, No. 2, Feb. 2009 pp. 331-336, DOI: 10.1007/s10439-008-9604-y.

Szarka et al. "Methods for measurement of gastric motility." American Journal of Physiology-Gastrointestinal and Liver Physiology 296.3 (2009): G461-G475 (Year: 2009); 15 pages.

\* cited by examiner

LABELLED – EARLY RECOVERY        LABELLED – LATE RECOVERY
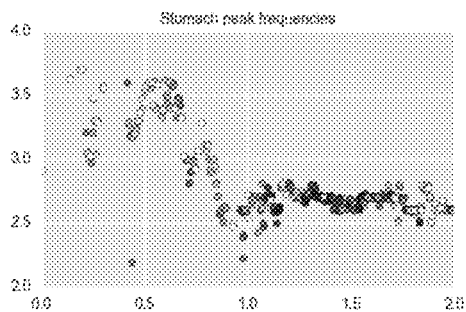
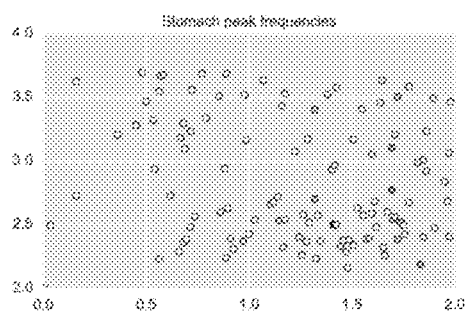
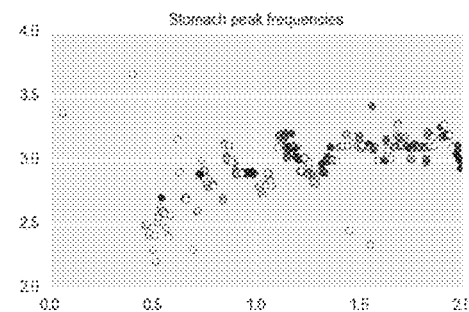
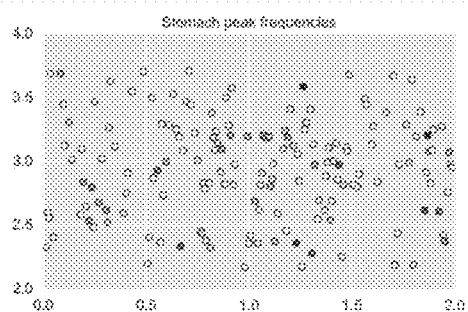
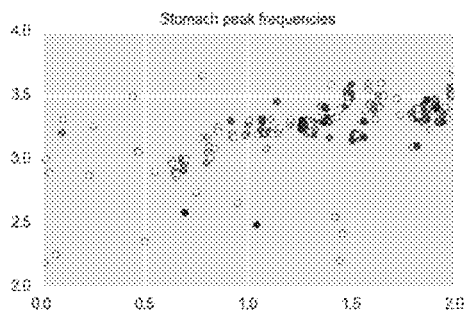
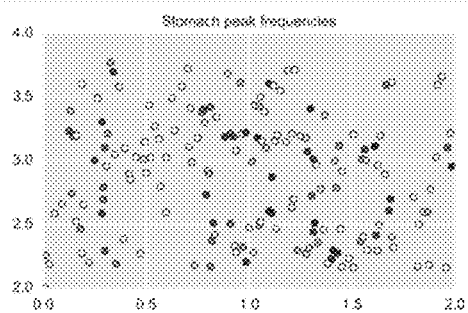
FIG. 57

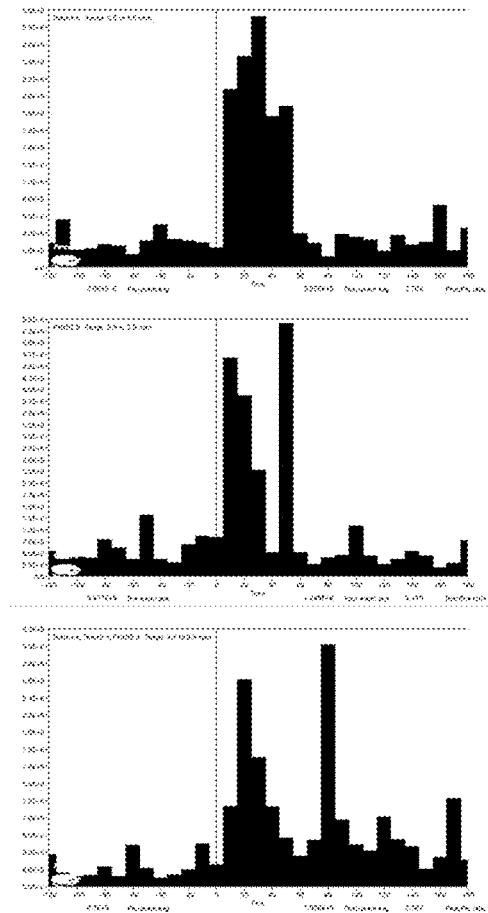 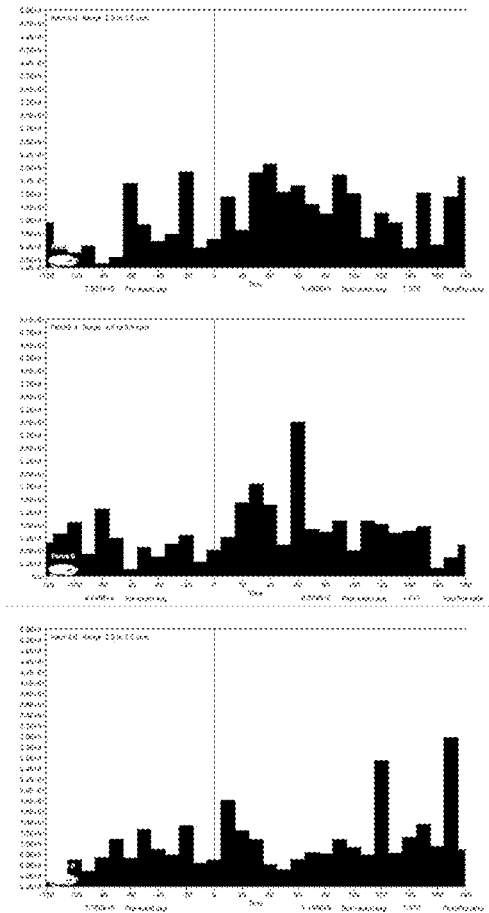
FIG. 58

ARTIFICIAL INTELLIGENCE MODELS FOR WIRELESS PATCH DATA ACQUISITION FOR GASTROINTESTINAL ELECTRODIAGNOSTICS

CROSS-REFERENCE TO RELATED APPLICATIONS

This application is a continuation-in-part of U.S. patent application Ser. No. 15/919,578, filed Mar. 13, 2018, which is a continuation of U.S. patent application Ser. No. 14/051,440, filed Oct. 10, 2013, now issued as U.S. Pat. No. 9,943,264 on Apr. 17, 2018, which claims the benefit of U.S. Provisional Patent Application Ser. No. 61/712,100, filed Oct. 10, 2012, the contents of each of which are herein incorporated by reference in their entireties.

This application is a continuation-in-part of U.S. patent application Ser. No. 16/692,550, filed Nov. 22, 2019, which is a continuation of U.S. patent application Ser. No. 15/518,929, filed Apr. 13, 2017, now issued as U.S. Pat. No. 10,485,444 on Nov. 26, 2019; which is the U.S. National Stage Application for PCT Application Ser. No. PCT/US2015/056282, filed Oct. 19, 2015, which claims the benefit of: U.S. Provisional Application No. 62/065,216, filed Oct. 17, 2014; U.S. Provisional Application No. 62/065,226, filed Oct. 17, 2014; and U.S. Provisional Application No. 62/065,235, filed Oct. 17, 2014, the contents of each of which are herein incorporated by reference in its entirety.

TECHNICAL FIELD

This disclosure relates generally to electromyographic (EMG) and electrodiagnostic systems and methods for profiling electrical activity within the smooth muscle of the gastrointestinal tract, and more particularly to systems and methods for mathematically extracting salient patterns of diseased electromyographic activity of the gastrointestinal tract from gathering large data sets of multi-hour and multi-day recordings from ambulatory patients with wearable, disposable, wirelessly-enabled sensor patches, and for diagnosing various gastrointestinal disorders. The disclosed invention can further be used in gastrointestinal drug research and discovery and for possible treatments of certain GI tract disorders.

BACKGROUND

The majority of gastrointestinal motility tests are invasive and a source of much discomfort and patient anxiety and expense. Therefore, advancing the state of the art in noninvasive technologies is highly desired. The present invention utilizes combinations of electrogastrography and electroenterography (EGG & EEnG), both of which allow for noninvasive and potentially long-term ambulatory data collection of patients, which in turn provides for greater patient convenience and comfort, lower costs, and more powerful diagnostic potential. EGG captures the rhythmical electrical activity of the stomach through electrodes located on the abdomen in the vicinity of the stomach, while EEnG captures the intestinal slow muscle electrical activity which may present anywhere on the abdomen.

Methods and systems for obtaining EMG data from the gastrointestinal tract of patients, particularly patients who appear to suffer from disorders related to gastrointestinal motility, are known in the prior art and practiced by specialists in the art. Such systems and methods typically are used in a procedure that occurs in a clinical setting, within a time frame of several hours, and wherein the patient needs to be substantially in repose. Further, the testing procedure usually asks the patient to adhere to a preliminary schedule of eating, and of eating a standardized meal. Finally, the typical electrographic measuring system is only taking measurements from a very small set of EMG bipolar electrodes, typically two or three, and thus measuring just a small sample of the entire gastrointestinal system, while using a large, extremely expensive, typical medical office electrodiagnostic signal amplification and data acquisition machine.

These constraints, however practical and appropriate, nevertheless likely limit the scope of data derived from such studies. The data are limited in GI tract coverage and time frame. A study is only feasible for several hours, during which a patient can tolerate or comply with the constraint on normal physical activity. This limitation should be understood against the perspective that, in reality, gastrointestinal activity occurs in the context of a daily cycle, and that daily cycle occurs in the context of activities of daily living. Gastrointestinal pain or discomfort also can be cyclical or chaotically intermittent throughout the day, or over the course of several days. Such intermittency may or may not be obviously tied to activities associated with the gastrointestinal tract specifically, or the more general and varied activities of daily living. Accordingly, it is proposed and likely that the diagnostic value of gastrointestinal activity data derived from tests that include such constraints has always been limited in its potential, thus greatly limiting the adoption and use of this field of GI diagnostic technology.

Further, such a gastrointestinal EMG study, as currently practiced, is expensive in that it occupies space in the clinic, and it occupies the time of the healthcare provider who is administering the testing procedure. As a consequence of a cost that limits the prevalence of such testing, the testing is generally applied to severe cases of gastrointestinal distress or to cases that are otherwise difficult to diagnose. And further still, the limited use of such testing limits the accumulation of data as a whole, which would advance understanding of the relationship between dysfunctional gastrointestinal electrical activity and gastrointestinal disorders.

Thus, there is a strong need in the medical marketplace for systems and methods that are more affordable, and which provide a more comprehensive view of gastrointestinal activity throughout a day or for longer periods, and which can monitor such activity while the patient is free to conduct the normal activities of daily living.

There are many examples in the prior art of remote, ambulatory, monitoring, recording and alarm EMG (and other medical sensor) systems. Although the presently disclosed system can include those functions, it is not the ideal objective and embodiment of this invention.

Instead, it is further a novel objective of the ideal embodiment of the present invention to allow for the easy and inexpensive collection of large spatial (skin attachable patches with distributed arrays of inexpensive orthogonal bipolar electrodes allowing coverage over the entire, or large sections, of the midsection) and temporal (overtime, ambulatory subjects going about their normal lives for hours to days) data sets.

All of the currently encountered prior art do not discuss concurrent multi-organ recordings, nor discuss whole digestive track, multi-day recordings for the purposes of GI tract disorder diagnosis. It is furthermore strongly suggested that the presently included invention is not wholly meant as a real-time monitor, since ideal embodiments will entail intermittent patch data storage and transmission in order to optimize battery life.

Additionally, the current state of the art generally allows for a few electrodes, without clear guidance on exact placement or spacing on the body, and recordings made in office for, at most, a few hours. The presently known art also teaches wearable EMG devices for continuous status monitoring, real-time disease event alarms, or personal health data recording. For example, in US patent application 20130046150, titled, Method for diagnosis and treatment of disorders of the gastrointestinal tract, and apparatus for use therewith, by inventor Uday Devanaboyina teaches a wearable, portable EMG system for long term home use, but does not teach a plurality of electrodes arranged in a paricular array on wireless patches, configured to cover the entire GI tract.

Additionally, wireless, wearable, home-use based ECG heart monitoring devices are well known in the art. For example, Biotronik US patent application 20130046150, teaches "Long-term cutaneous cardiac monitoring." The system disclosed is for long-term heart monitoring via a disposable adhesive surface patch for cutaneous mounting with built-in electrodes and wireless communication with a remote service center. However, the nature of cardiac heart muscle tissue signals is very different than that of the Gastrointestinal system, and thus, the patent does not teach about grids of electrodes or complex aggregate spatiotemporal data analysis. Cardiac systems typically require only two or three electrode pairs, and individual heart beats are analyzed or monitored, rather than presented as aggregate heartbeat data.

Furthermore, numerous examples of small, disposable, wireless, adhesive wearable medical EMG data collection patches exists in the marketplace. For example, DELTA Danish Electronics, Light & Acoustics, Inc., Denmark, has developed an ePatch® system for home health monitoring. (http://epatch.madebydelta.com). While this system and others are examples of the growing trend of wearable medical devices, it does not teach beyond the well-known EGG medical practices—few electrodes, primarily for monitoring purposes, and analyzed linearly rather than aggregately. No suggestion is made for full GI track monitoring by arrays of electrodes over long time periods for advanced spatiotemporal data pattern analysis.

Additionally, there are numerous research papers exploring the use of wireless EMG and EGG systems for home health monitoring. For example, S. Haddab, et al, proposes a "Microcontroller-Based System for Electrogastrography Monitoring Through Wireless Transmission" system. However, like all other commercial and scientific EGG efforts, his efforts are short term (four hours maximum), and with a minimum of traditional electrodes. No suggestion of multi-day recording is made. The mathematical analysis was of the traditional type designed to remove noise and artifact from the linear signal, rather than achieve diagnostic successes through spatiotemporal pattern analysis of data aggregated from in-situ subjects over multi-day periods.

The same is true of Haahr, R. G., et al, who despite their promising work on "A wearable 'electronic patch' for wireless continuous monitoring of chronically diseased patients," they specifically teach a "wearable health system . . . made as an electronic patch . . . (and) for the EMG application three standard dry silver electrodes are used separated by 10 mm."

U.S. Pat. No. 7,593,768, "Detection of smooth muscle motor activity," discloses EMG peak detection in the frequency spectrum and calculating the energy of the peaks for the stomach and small intestine using internal and surface electrodes. It does not teach towards the presently disclosed invention. Specifically, only mention of the recording time involved a maximum time of two hours, and the maximum number of electrodes mentioned was eight. Furthermore, these eight electrodes were implanted, not external, and their data was summed up into one time series, not analyzed as a spatial temporal pattern. Nor is there any mention of wearable or wireless data collection for ambulatory, at home data collection.

While there is a long history of minor success with EGG approaches, and EGG/EEnG possesses important information regarding the physiological and functional state of the GI tract, the cost and limited diagnostic benefit has so far prevented the mainstream and large scale medical mainstream use of EGG and EEnG.

Furthermore, there is enormous variability in the anatomical nature and structure and organ placement and tissue densities among patients. There is also enormous variability in both the healthy and disordered GI tract slow muscle rhythmic activity physical parameters and patterns. These two factors prevent any kind of EMG electrode placement standardization and limit the effectiveness of EMG in diagnosing the large number of different GI tract disorders commonly encountered in the clinical setting.

Thus, it is an objective of the present invention to create a system that places enough of an array of particularly arranged electrodes over larger GI tract areas, or the entire GI tract, to obviate the issues caused by non-standard electrode placements or individual anatomical variability.

SUMMARY

As described elsewhere herein, there exists an almost infinite variety of different electrode arrangements, some of which will possess differing advantages and disadvantages with regards to optimization of cost versus data collection versus additional engineering, diagnostic, and business consideration.

It is instead suggested that by having any plurality of variously spaced, orthogonally arranged bipolar electrode pairs on a patch, with one or more patches covering the entire, or large part, of one or more digestive organs, sufficiently ideal diagnostic data sets can be collected, throughout a single days normal digestive activities, (a single "gut beat"), for sufficient mathematical post-processing to yield great diagnostic value. Furthermore, by employing multiple electrodes and patches, it is also possible to dynamically alter which electrodes form bipolar pairs based on incoming data optimization algorithms. Importantly, a plurality of smaller patches, rather than one single giant patch, is an ideal embodiment because smaller patches help prevent significant lateral movement of electrodes on the skin.

In addition to the previously mentioned limitations of standard EGG, there are many sources of data variability, including patient height, weight, anatomy, skin condition, recent food consumption history, metabolic rest state, and the like.

Furthermore, data variability is additionally introduced from highly variable placement of electrodes or patches, or in equipment manufacturing variations, and of course the variability caused by different disorders and the general chaotic and nonlinear dynamic nature of biological systems. These large variations negatively impact diagnostic effectiveness of all previous known systems. This variability problem is compounded further by the fact that EGG is a lower amplitude signal compared to other bodily electrophysiological signals, such as the heartbeat or breathing, and thus easily influenced by both random sources of variation and systematic influence factors.

It is thus an objective of the presently disclosed invention to effectively avoid these limitations by use of the presently disclosed patches, in combination with continual or intermittent data collection and transmission over periods of many hours, days, in combination with advanced mathematical techniques, in both the time and frequency domains.

The usual 24-hour circadian cycle of the body is well representative of the digestive cycle of the normal or healthy body. Research has shown that the digestive system follows a similar 24-hour pattern, with low GI activity during sleep, increased activity after waking and temporary increases following breakfast and other meals, with defecation often occurring at more or less the same time each day. This full cycle of GI activity might be called a "gut beat" in analogy to the heartbeat cycle of the heart.

In as much as there are events such as Giant Migrating Contractions (GMC's) and Migrating Motor Complexes (MMC's) associated with propulsion of the contents of the intestines that occur on the order of a few to several times per gut beat, capturing data for at least one full day is essential to develop an understanding of the workings of an individual's digestive system with the intent to diagnose abnormality. In fact, due to normal variability, it is further advantageous to sample for several days to better quantify infrequent events, capture rare events, and reduce statistical noise in the measurement of common events.

An example of a common event is the increase in degree of muscular activity in any of the stomach, small intestine, or colon after a meal. In general, all these organs respond to meal ingestion either within minutes or tens of minutes, and quantifying that increase has diagnostic value. An example of an uncommon event is limited propulsion of the luminal contents of the small intestine, which typically happens several times per day in healthy subjects. An example of a rare event is defecation, which happens on average once per day for healthy subjects, but for patients with constipation it may only happen once every several days.

Thus, we would characterize this combination of multiple patches of multiple electrode pair arrays designed to sample, store, and wirelessly transmit data intermittently to remote computer servers over a larger segment of time, as the collection of spatio-temporal electromyographic data. And while there are an infinite number of ways for the remote servers to mathematically and algorithmically analyze and display said aggregates of such large data sets, the presently ideal embodied invention utilizes techniques such as time series analysis, time-dependent frequency analysis, and pattern matching analysis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

One aspect of the present disclosure is directed to a method of extracting valid gastrointestinal tract EMG data from a raw time series data set acquired from an electrode patch. In some embodiments, the method includes: obtaining data from an electrode patch configured to sense and acquire EMG voltage signals; identifying artifacts within a raw time series training data set derived from the EMG voltage signals, the identified artifacts comprising a set of data points nominally centered timewise on a point of largest excursion from an average value of zero-crossing and extending toward an average or zero-crossing; training a machine learning model on the identified artifacts in the raw time series training data set; and applying the machine learning model to a raw time series test data set.

In some embodiments, the machine learning model is configured to: identify the one or more artifacts in the raw time series test data set and classify each of the one or more artifacts based on one or more characteristics of the one or more artifacts; eliminate the one or more identified artifacts from the raw time series test data set by tracking them down to any of a zero-crossing or a midpoint-crossing point on either side of a high amplitude artifact; and replace the one or more identified artifacts with any of interpolated points or constant value points that span a gap across the eliminated artifacts to create a clean time series data set comprising the valid gastrointestinal tract EMG signals.

In some embodiments, the skin-surface mounted electrode patch comprises an array of bipolar electrode pairs.

In some embodiments, the array comprises two or more bipolar pairs of electrodes arranged substantially orthogonally relative to each other.

In some embodiments, identifying artifacts within the raw time series training data set is based on a standard deviation of the set of data points.

In some embodiments, identifying artifacts within the raw time series training data set is based on a percentile ranking of the set of points where the artifact is identified as a structure having at least one data point in an extreme percentile.

In some embodiments, identifying artifacts within the raw time series training data set comprises filtering the raw time series data to remove low frequencies or high frequencies from each channel.

In some embodiments, identifying artifacts within the raw time series training data set comprises offsetting data amplitude by an average amplitude, thereby creating a data set with an average value of zero.

In some embodiments, identifying artifacts within the raw time series training data set comprises tracking to the nearest zero-crossing or midpoint-crossing, the individual point nearest to zero/midpoint is selected on either side, and replacement points are interpolated between the two points so determined.

In some embodiments, identifying artifacts within the raw time series training data set comprises tracking to the nearest zero-crossing or midpoint-crossing, and all replacement points are set to zero or to the midpoint value as appropriate.

In some embodiments, identifying artifacts within the raw time series training data set comprises using an adaptive threshold criterion, such adaptive threshold criterion based on statistical measures complementary to a statistical measure used to set a preliminary threshold.

In some embodiments, identifying artifacts within the raw time series training data set comprises using characteristics of data shape that have been previously identified as artifactual.

In some embodiments, the data shape includes a rapid initial excursion followed by an approximately exponential decay with or without subsequent ringing.

In some embodiments, the machine learning model comprises approaches based on Artificial Neural Networks, Bayesian Networks, Random Forests, and Decision Tree Learning methods.

In some embodiments, each identified artifact includes unique characteristics comprising one or more of: an amplitude, a periodicity of variations, a frequency of variations, and a shape of an envelope.

In some embodiments, identifying the one or more artifacts, using the machine learning model, is based on one or more characteristics comprising: an amplitude, a periodicity of variations, a frequency of variations, a shape of an envelope, or a combination thereof.

In some embodiments, the artifact identified by the machine learning model comprises an artifact amplitude lower than an amplitude of surrounding rhythmic activity In some embodiments, the method further comprises positioning the electrode patch onto an abdominal region of a patient.

Another aspect of the present disclosure is directed to a system for non-invasive monitoring of gastrointestinal track activity. In some embodiments, the system includes: an electromyographic-sensing patch adapted for attachment to a skin surface of a midsection of a patient, the patch comprising an array of bipolar electrode pairs comprising two or more bipolar electrode pairs arranged orthogonally relative to each other; and a first processor communicatively coupled to the electromyographic sensing patch, and memory having instructions stored thereon, wherein execution of the instructions causes the first processor to perform a method.

In some embodiments, the method includes: obtaining data from the electromyographic-sensing patch configured to sense and acquire EMG voltage signals; identifying artifacts within a raw time series training data set derived from the EMG voltage signals, the identified artifacts comprising a set of data points nominally centered timewise on a point of largest excursion from an average value of zero-crossing and extending toward an average or zero-crossing; training a machine learning model on the identified artifacts in the raw time series training data set; and applying the machine learning model to a raw time series test data set.

In some embodiments, the machine learning model is configured to: identify the one or more artifacts in the raw time series test data set and classify each of the one or more artifacts based on one or more characteristics of the one or more artifacts, eliminate the one or more identified artifacts from the raw time series test data set by tracking them down to any of a zero-crossing or a midpoint-crossing point on either side of a high amplitude artifact, and replace the one or more identified artifacts with any of interpolated points or constant value points that span a gap across the eliminated artifacts to create a clean time series data set comprising the valid gastrointestinal tract EMG signals.

In some embodiments, the system further comprises a remote computing device or a networked computing device comprising the first processor.

In some embodiments, the electromyographic-sensing patch further comprises a circuit board having a battery and a second processor configured to receive the EMG voltage signals from the array of bipolar electrode pairs and transmit data to the first processor on the remote computing device or the networked computing device.

BRIEF DESCRIPTION OF THE DRAWINGS

Various embodiments of the invention are disclosed in the following detailed description and accompanying drawings.

Other features and advantages of the invention will become apparent from the following detailed description in conjunction with the drawings.

FIG. 3A provides a simplified bottom view of a patch, and FIG. 3B provides a simplified bottom view, of a wearable, disposable/recyclable unit 100 and an electrode patch EMG circuit 200 including array of nine bipolar electrodes 205 as an exemplary example of the invention.

FIG. 35 shows a spectrum in blue and derivative in red.

FIG. 57 shows examples of training data that include peak frequency activity in the 2 to 4 cpm range corresponding to the stomach for patient's recovering from the Whipple surgery.

FIG. 58 shows examples of training data that include peak stomach activity in the 2 to 4 cpm range around a meal for healthy control subjects on the left column and patients with gastroparesis on the right column.

Figure 1:
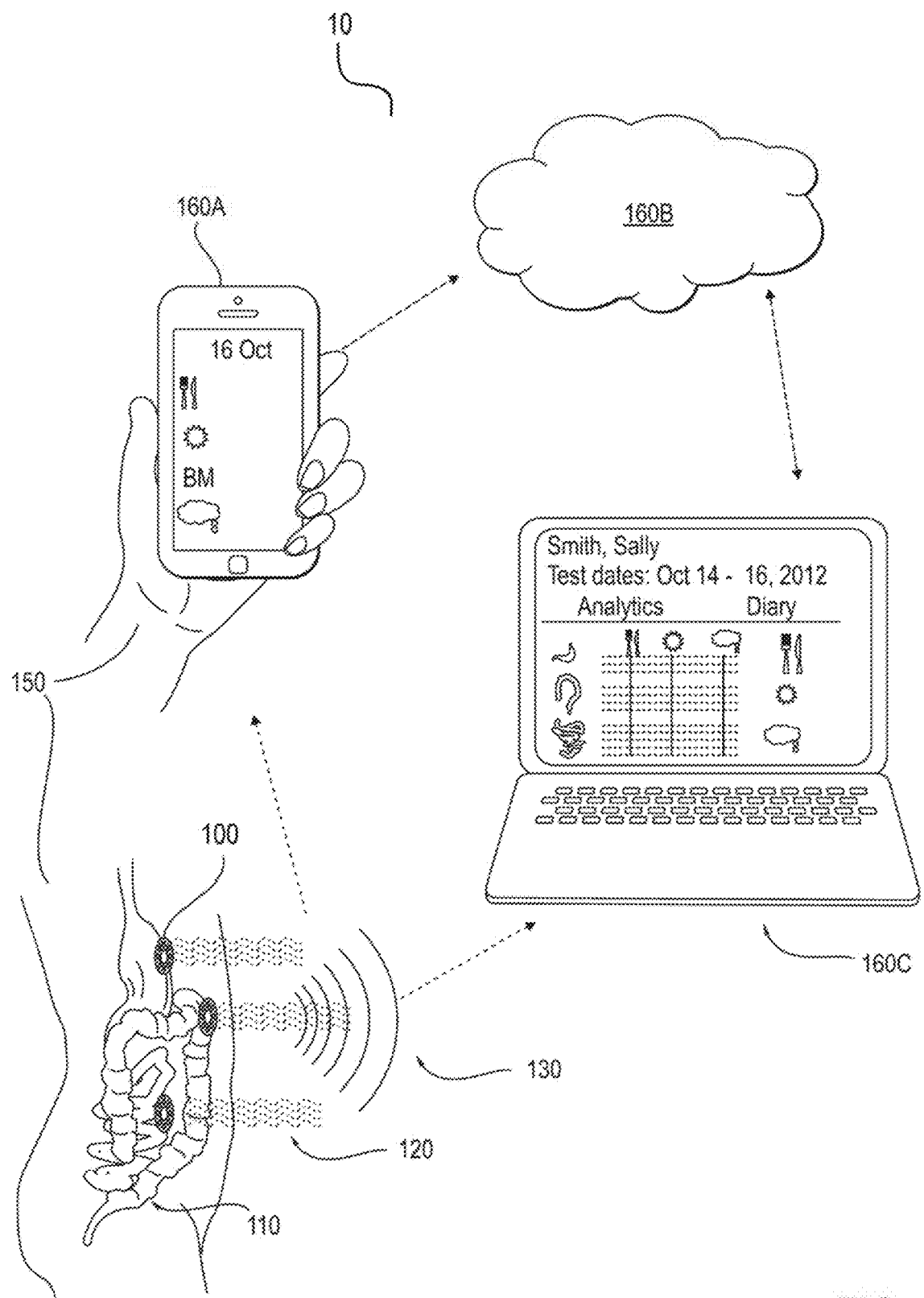
FIG. 1 schematically illustrates an embodiment of a wearable, wireless, GI electrodiagnostic data aggregating and diagnostic system.

The illustrated embodiments are merely examples and are not intended to limit the disclosure. The schematics are drawn to illustrate features and concepts and are not necessarily drawn to scale.

DETAILED DESCRIPTION OF THE PREFERRED EMBODIMENT

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

One aspect of the present disclosure is directed to a wearable non-invasive wireless electrodiagnostic patch system for profiling gastrointestinal tract muscular activity of a subject. The system comprises a set of electromyographic-sensing patches adapted for multi-day constant attachment to the skin surface of the midsection of a subject; each patch of said set comprising a particularly arranged array of bipolar electrode pairs; each patch enabled for collecting, storing, processing, and communicating a range of full to partial time segments of sensed spatiotemporal electromyographic signals from the subject to remote computing and display devices. Said computing devices are configured to mathematically and algorithmically process and analyze aggregated amounts of said spatiotemporal electromyographic signals to yield visually displayable, diagnostically valuable physiological parameters of gastrointestinal smooth muscle electrical activity of said subject In some embodiments of the particularly arranged array of bipolar electrode pairs, the distribution and orientation pattern allow for a maximum number of electrodes pairs to be arranged substantially orthogonally to each other in order to better sense signals originating from any orientation or location In some embodiments, said parameters comprise any of frequency, amplitude, power, or periodicity of electrical activity, as well as periodicity of larger time frame patterns of electrical activity, said parameters further assignable to a region of the gastrointestinal tract.

In some embodiments, the communicating of said patches EMG data to said remote computing devices occurs wirelessly, for example via Bluetooth, Wi-Fi, cellular, infrared, and the like.

In some embodiments, said patches are selected from the group: designed to be used as a larger number of smaller patches, to cover a large portion of the GI tract, so as to minimize lateral slippage and movement of electrodes; designed so each electrode pair is aligned radially; designed so each electrode pair is aligned along a circumferential line; designed so one electrode is a ground electrode and is configured to pair with a plurality of active electrodes, each pairing representing a bipolar electrode pair; and designed so the ground electrode is disposed centrally within a circumferential arrangement of the plurality of active electrodes.

In some embodiments, each of the EMG-sensing patches comprises a memory capacity sufficient to store accumulated signal for a period of up to at least one hour.

In some embodiments, the networked computing device comprises one or more data analysis applications, said applications configured to analyze data transmitted to it from the local electronic device, and said data analysis is selected from the group comprising: individuation of processed data according to unique identifiers with which data coming from each patch is tagged; desired signal isolation based on subtraction or relative weighting of patterns ascribable to sources other than gastrointestinal smooth muscle; comprises inclusion of data directly entered into the local electronic device by the patient; comprises inclusion of data entered directly into a computing device by a healthcare professional; and comprises recognition of each EMG-sensing patch according to a coordinate-mapped location on the body of the patient.

In some embodiments, the mathematical and algorithmic analysis of said aggregated large data sets is selected from the group including: time series analysis, time-dependent frequency analysis, and pattern matching analysis.

In some embodiments, the subject includes both humans and animals, and said diagnostically valuable physiological parameters are valuable for both diagnosing GI tract diseases, and diagnosing the effects of various foods, pharmaceutical drugs, and other substances on GI tract activity and health.

In some embodiments, said subject is enabled in a manner selected from the group: being able to go about their daily lives; being able to manually enter consumed food descriptions into their medical records via portable, desktop, and handheld computing devices; being able to manually enter qualitative or quantitative values of GI pain and its location, bloating, nausea and other disease symptoms experienced and their time experienced; being able to take pictures of meals to be consumed as additional data to be included in the analysis; being able to take pictures of meals to be consumed, with automated interpretation of nutritional content, as additional data to be included in the analysis; and being able to record still pictures, audio, and video messages that are entered into their medical records.

In some embodiments, the system further comprises additional sensors selected from the group consisting of: accelerometers, motion sensors, position sensors, heart rate sensor, image sensor, blood pressure meter, respiration rate, blood oxygen levels, body temperature, galvanic skin response, skin-electrode impedance, electrode-electrode impedance, accelerometers, audio microphones, photography, videography, ECG, and EEG.

Another aspect of the present disclosure is directed to a low-cost, non-invasive method of profiling gastrointestinal tract muscular activity of an ambulatory patient. The method comprises: placing at least one EMG-sensing patch on a skin surface of the patient proximate the gastrointestinal tract, said EMG-sensing patch comprising particularly selected arrays of bipolar electrode pairs; acquiring electrical signals from one to all regions of the gastrointestinal tract with at least some subset of said plurality of electrode pairs arranged as arrays on each individual patch; acquiring electrical signals from one or more regions of the gastrointestinal tract with at least some subset of said plurality of said EMG-sensing patches; acquiring electrical signals at intervals ranging from intermittently to continuously from ambulatory patients living and behaving normally over at least a substantial portion of one day; wirelessly transmitting said acquired electronic signal data to nearby networked computing devices; and collecting, transmitting, and mathematically processing the acquired aggregated signals on any of the said computing devices to yield and display physiological parameters of gastrointestinal electrical activity collected from patients.

Another aspect of the present disclosure is directed to a non-invasive, wearable, low-cost full GI tract electrodiagnostic device and method. The device and method comprises: a plurality of electromyographic-sensing wearable patches covering substantially all of the GI tract, said patches adapted for placement on the skin surface of the midsection region of a subject, said patches optionally available in a variety of sizes, shapes, and bipolar electrode densities and array distribution configurations. Each said patch comprises at least one bipolar electrode pair, and said patch is additionally enabled for intermittent to continuous, wireless communication of a signal indicative of a sensed, recorded, electromyographic signal. Said electrodes are linked to an electronic device, wherein said electronic device includes: amplifier circuits, band pass filter circuits, analog to digital converter circuits, memory circuits, wireless data transmission circuits and associated antenna, a light, ultra-compact power source, and a water-resistant housing. Said housing is made for multi-day adherence to said subject's body, and said electronic device is in wireless communication with networked computing devices. Said networked computing device is configured to utilize advanced mathematical and algorithmic processes to analyze aggregate signals received from the local electronic device in order to yield remotely viewable physiological parameters of gastrointestinal smooth muscle electrical activity for the purposes of diagnosis and treatment of GI disorders.

The networked computing device comprises one or more data analysis applications, said applications configured to analyze data transmitted to it from the local electronic device. Embodiments of the present invention include a system wherein data analysis comprises individuation of processed data according to unique identifiers with which data coming from each patch is tagged. Embodiments of the present invention also include the system wherein data analysis comprises desired signal isolation based on subtraction or relative weighting of patterns ascribable to sources other than gastrointestinal smooth muscle. In this and other embodiments, the patterns ascribable to sources other than gastrointestinal smooth muscle are identifiable through comparison of relative strength of signals from EMG-sensing patches, the patches identified per their location on the skin surface relative to an underlying gastrointestinal tract region.

In some embodiments, the one or more data analysis applications may employ artificial intelligence (AI) and/or machine learning (ML) techniques to find patterns and/or features in acquired and/or analyzed EMG voltage data. For example, the ML may be trained on raw EMG voltage data, normalized data, data having one or more artifacts removed, data having one or more peaks identified therein, or a combination thereof with various peaks, features, or patterns already identified in any of the data sets identified. For example, supervised or unsupervised models (e.g., Artificial Neural Networks, Bayesian Networks, Random Forests, Decision Tree Learning methods, etc.) may be used to detect one or more events leading up to and responses to specific events, such as meals, bowel movements, pain, and sleep in spectral data, peak data, and/or raw data, and classify the responses into different categories. Non-limiting examples of classified responses include a weak or strong stomach signal following a meal event; high activity in any organ associated with a pain event; colon or small intestine activity before or after a bowel movement event; and/or diurnal changes in activity in the colon or other organs. The categories could then be used with either further AI/ML or human interpretation to classify patients based on health and disease states. This technique will be further used to recognize responses in the data to allow for identification of an event not identified by the patient or identified before the event may occur (i.e., prognostic).

Figure 51:
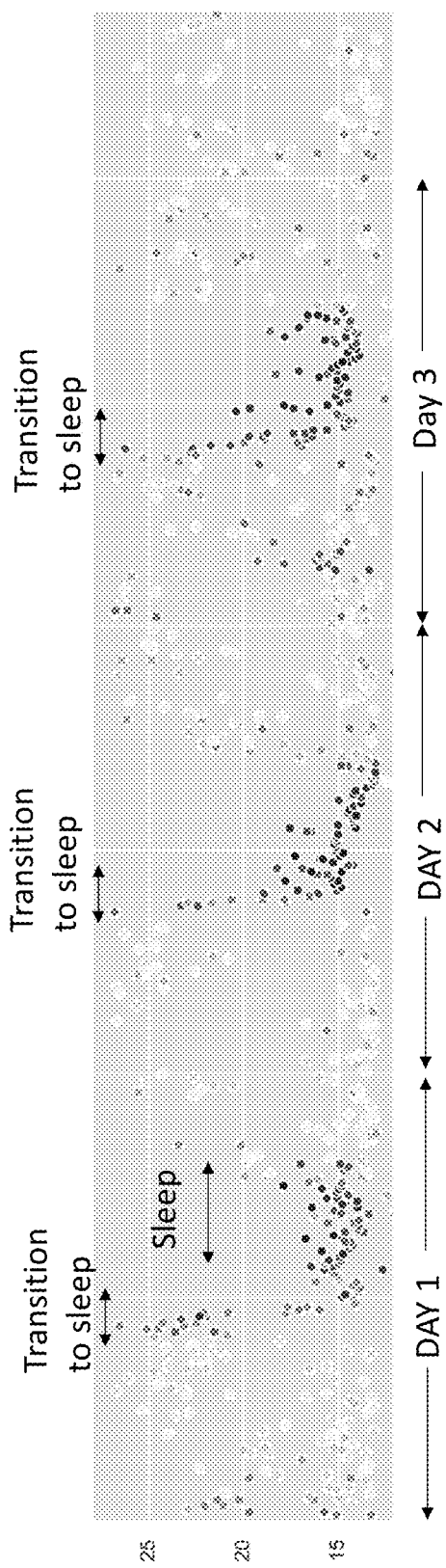
FIG. 51 shows examples of training data that include peak frequency plots over the course of several days across the 0 to 28 cpm range.

ML based data analysis applications may also be employed to detect patterns in the raw data to identify periods of sleep and/or rest. The ML model may be a classification model trained on known periods of sleep and/or rest and known periods of non-rest activity. An example of a known pattern that is uniquely observed in the raw and peak data is the presence of increased colon activity and shifting colon frequencies during sleep or night periods. FIG. 51 shows examples of training data that include peak frequency plots over the course of several days across the 0 to 28 cpm range. The color gradient represents amplitude of the observed peaks, with the darkest color reflecting a stronger peak and the lighter color a weaker peak. The peaks seen in the red represent colon activity for this particular individual. As labeled, a shift in the colon frequencies from the mid-twenties to the high teens are observed during the transition from awake to sleep, with this pattern repeating over the next few days. In addition to the observed transition, the sustained presence of colonic activity in the data by itself could be representative of sleep and used to train an ML model.

Further embodiments of the present invention include a system where the data analysis comprises identification of signal peaks related to each other, wherein related peaks may occur at either the same or at different frequencies. In this and other embodiments, the data analysis comprises subjecting data to a Fast Fourier Transformation algorithm at one or more sample lengths, said algorithm directed toward identification of peaks with optimal signal to noise ratio and optimal signal strength. Further embodiments of the present invention include data analysis comprising integral wavelet transform analysis. Still further embodiments of the present invention include data analysis comprising pattern analysis, wherein received data are compared against examples of known patterns. Additional embodiments of the present invention are systems where the data analysis comprises a search for non-sinusoidal patterns through a pattern-matching algorithm. For example, harmonics (e.g., sharp peaks at integer multiples of the primary frequency) may be identified. Once identified, the energy from these peaks is subtracted from the organ range (i.e., current frequency) in which they appear and added to the proper or correct frequency range based on the true organ that they represent. For example, when a 3 cpm stomach signal has a 6 cpm harmonic, the 6 cpm energy would normally indicate small intestine activity. If the 6 cpm energy is identified as a stomach signal based on a ratio of energy in the 3 cpm and 6 cpm peaks (over their recent history and taking into account their widths), the stomach energy can be subtracted from the 6 cpm frequency and added to the 3 cpm frequency.

Further, data analysis comprises inclusion of data directly entered into the local electronic device by the patient or a healthcare professional. Another embodiment of the present invention is a system wherein data analysis comprises inclusion of data entered directly into a computing device by a healthcare professional.

FIG. 1 schematically illustrates an embodiment of a wearable, wireless, GI electrodiagnostic data aggregating and diagnostic system, including computing devices 160a for easy patient 150 supplemental data entry, and remote computer display devices 160c for patch 300 wireless transmission 130. The remote computer servers 160b process for display the GI tract 110 physiological parameters 120 for doctor diagnostic assistance.

FIG. 1 presents a system wide view, with a set of multi-day-wearable patches 300/200 that sense, amplify and digitize myoelectric data 120 at the skin surface 150 originating in the smooth muscles of the stomach, small intestine, and colon, 110 and transfer the data wirelessly 130 to a computing device 160a. The patches have two or more bipolar pairs of electrodes 205 arranged substantially orthogonally, the patches further having onboard sensors that are capable of measuring any of acceleration, velocity, and/or position 402. The computing device is further configured to allow the patient to enter 420 information 160a relevant to their gastrointestinal (GI) tract such as meal contents, bowel movements, or abdominal pain and synchronize and combine this information with the time-stamped 416 raw data 120. The data are uploaded both to a cloud server 160b or other wireless host, such that the host serves as a repository for further processing or download to a processing device. The processing device uses time and frequency based algorithms to extract events and patterns of events that relate to the activity of the aforementioned GI organs 120, specifically slow waves that are associated with mixing and propulsion of their contents as part of digestion and elimination, with the purpose of providing diagnostic information on the activity of the organs as they relate to functional GI disorders (FGIDs) such as irritable bowel disorder (IBS). The computing device further has the ability to coordinate data transfer schedules with the patches to accommodate either regularly scheduled transfers 404 or reconnecting when temporarily out of range, and the further ability to identify patches individually.

Figure 2A:
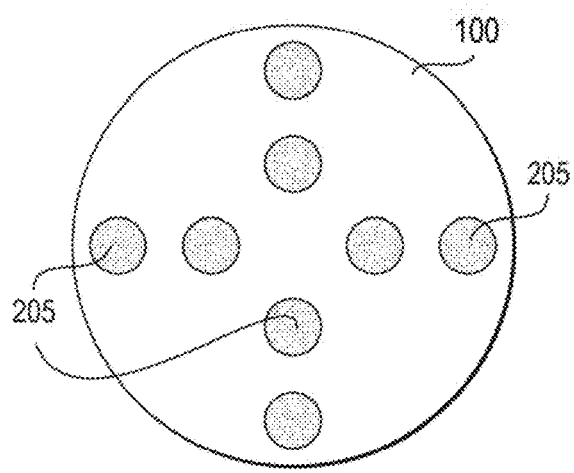
FIGS. 2A-2E show a bottom view of various embodiments of a multi-electrode configuration of the disposable unit 100, shown with its corresponding electronic controller detached and spaced from the disposable unit 100.
Figure 2B:
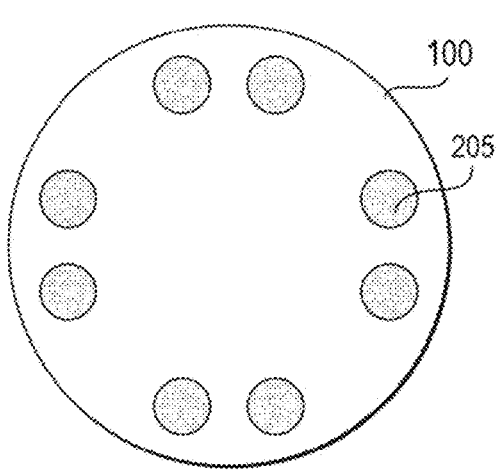
Figure 2C:
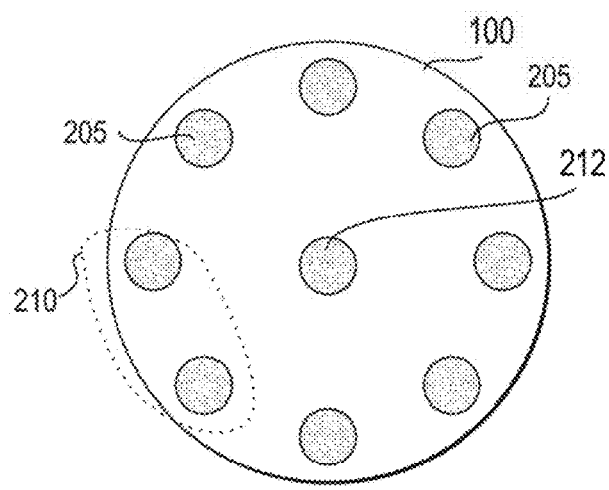
Figure 2D:
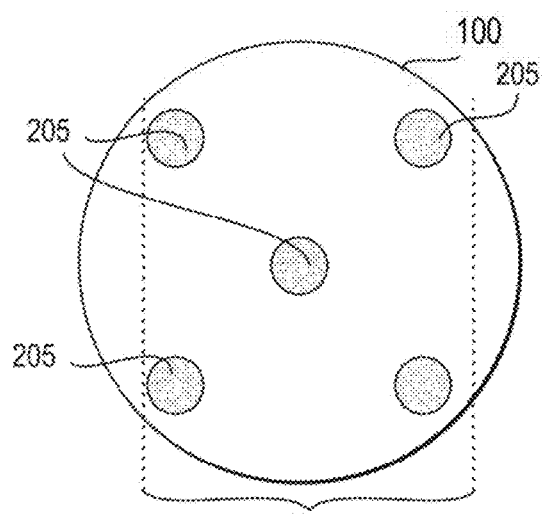
Figure 2E:
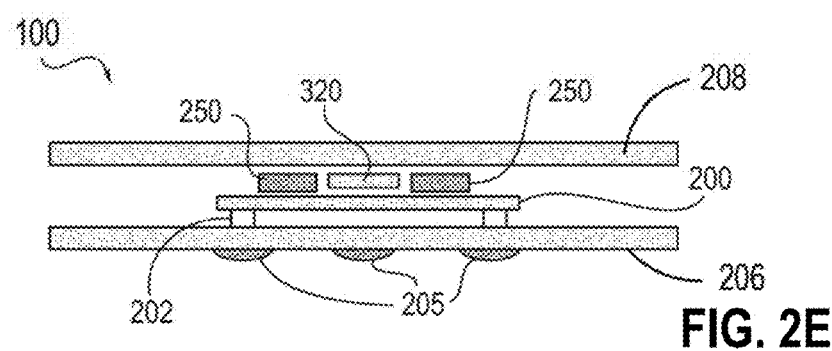

One embodiment of a patch design and several non-limiting examples of electrode configurations are provided in FIGS. 2A-2E. As shown in FIG. 2E, the patch 100 of some embodiments includes a bottom, skin-side layer 206 with two or more bipolar electrode pairs 210 positioned on a bottom surface of the bottom layer 206. A plurality of integrated circuit (IC) board adhesive pins 202 extend through the bottom layer 206 to connect each electrode 205 of the bipolar electrode pairs 210 to an integrated circuit board 200 positioned on a top surface of the bottom layer 206. In some embodiments, the electronics of the integrated circuit board 200 are protected from moisture and patient manipulation by being sandwiched between a waterproof top, air-side layer 208 and the bottom, skin-side layer 206. The integrated circuit board 200 includes one or more integrated circuits 250 and a battery 320. The integrated circuit board 200 may also include signal processing components. For example, the integrated circuit board 200 may include one or more of: a filter (e.g., low pass filter, high pass filter, or band pass filter), an amplifier, an analog-to-digital converter (ADC), and a processor (e.g., Arduino® or other microcontroller) to process and analyze signals received from the electrodes 205. The patch 100 may further include a transmitter or a transceiver antenna to transmit signals from the patch 100 to the cloud-based server 160B or the mobile device 160A, as shown in FIG. 1.

Figure 3A:
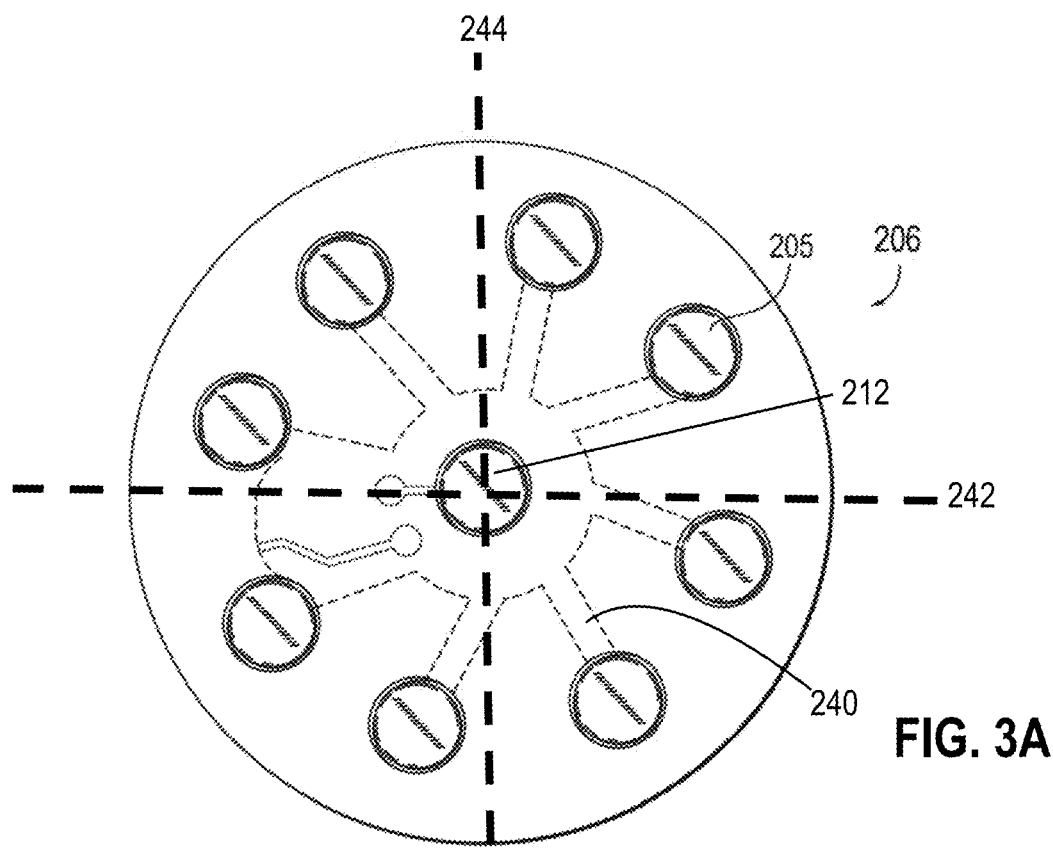
FIGS. 3A-3B show one embodiment of a patch.
Figure 3B:
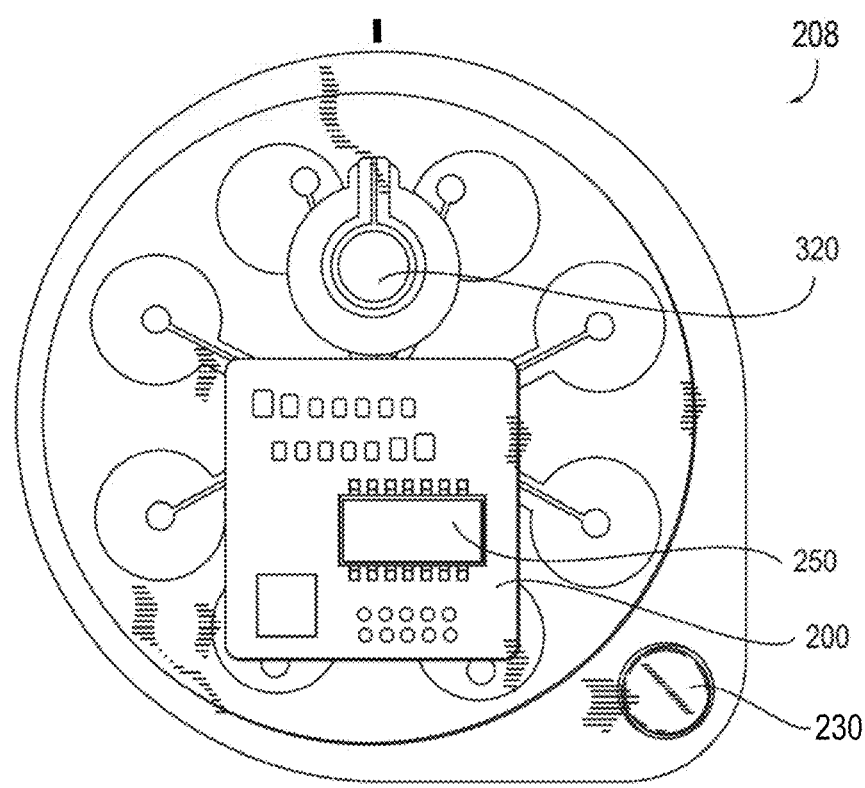

In some embodiments, as shown in FIGS. 2A-2D, each patch 100 includes two, three, four, five, six, seven, eight, nine, ten, or more electrodes 205. In one embodiment, the patch 100 includes four bipolar electrode pairs 210, for example as shown in FIGS. 2A-2C. In some such embodiments, the patch 100 also includes a grounding electrode 212, as shown in FIGS. 2C, for a total of nine electrodes 205. The ground electrode 212 may be disposed substantially in a center region of patch 100, such that electrodes 205 are disposed circumferentially around ground electrode 205. In other embodiments, ground electrode 212 may be positioned anywhere on patch 100. The electrodes 205 may be electrically coupled via arms 240. Arms 240 are arranged such that patch 206 conforms and bends or flexes in two dimensions along two perpendicular axes 242, 244. Further, in some embodiments, a plurality of interchangeably paired electrodes 205 may form an electrode array 220, as shown in FIG. 2D. In some such embodiments in which the electrodes 205 are configured to change the pairings of electrodes during signal acquisition, fewer electrodes may be needed to determine directionality, strength, and/or breadth of the signal. While a few example electrode arrangements are shown in FIGS. 2A-2D, those skilled in the art will appreciate that any suitable electrode arrangement may be used and is contemplated herein. Moreover, while a circular patch is shown, it is also contemplated that the patch may be rectangular, star shaped, oval, or any other suitable regular or irregular shape. Further, as shown in FIG. 3A, the patch 100 includes pairs of bipolar electrodes 205 on the bottom surface 206. The top surface 208, as shown in FIG. 3B, includes a printed circuit board 200 and a power source 320. The printed circuit board 200 and power source 320 may be protected from moisture or user movement by an additional layer that couples to the bottom surface 206 and sandwiches the printed circuit board 200 and power source 320 between the bottom layer 206 and a top layer 208, as shown in FIG. 2E. The patch further includes switch 230 that, when removed from a perimeter of the patch and positioned on a flex circuit of power source 320, completes the circuit and the power source 320 is activated. Switch 230 comprises a conductive, pressure-sensitive adhesive. Such embodiment provides an easy, thin switch while minimizing accidentally powering off the device.

Further, in the embodiment of FIGS. 3A-3B, using pairs of bipolar electrodes on one or more patches, it is possible to dynamically alter which electrodes form bipolar pairs based on incoming data optimization algorithms and/or alter which patch is used for data analysis. For example, the raw data coming from each patch may be analyzed for signal strength. If a signal strength for a particular patch is above a certain threshold, that patch may be selected for further data processing, as described elsewhere herein. Additionally, all channels coming from all patches may be analyzed for signal strength and/or quality, such that a particular channel on a particular patch is selected for further data processing, as described elsewhere herein.

FIG. 2 schematically illustrates the electrode array circuit board 200. The disposable unit 200 has at least two, but preferably eight embedded bipolar pair electrodes 205 arranged in an array 220. Preferably, the inter-electrode distance is between 1 and 2 inches. The electrodes 205 are embedded inside the printed circuit board patch unit 200, with an ideally slight extension for greater skin contact. The circuit board 200 will likely be entombed in waterproof resin for greater water resistance, and the patch housing itself 300 will ideally have water resistant properties.

FIGS. 3A-3B show a bottom and top view, respectively, of an exemplary patch 300 and electrode array circuit board 200. An inexpensive, light, water resistant and disposable skin-adhesive unit 100 is provided for long-term non-invasive GI tract monitoring. Because the unit is disposable, it can be easily replaced with another disposable unit after its usage for a few days. The bottom of the disposable unit 100 has an adhesive surface 110 that can be affixed to the patient's skin for at least 7 days. One exemplary type of such adhesive material is the pressure-sensitive adhesive which forms a bond when pressure is applied to stick the adhesive to the adherent (e.g., the patient's skin).

Figure 4:
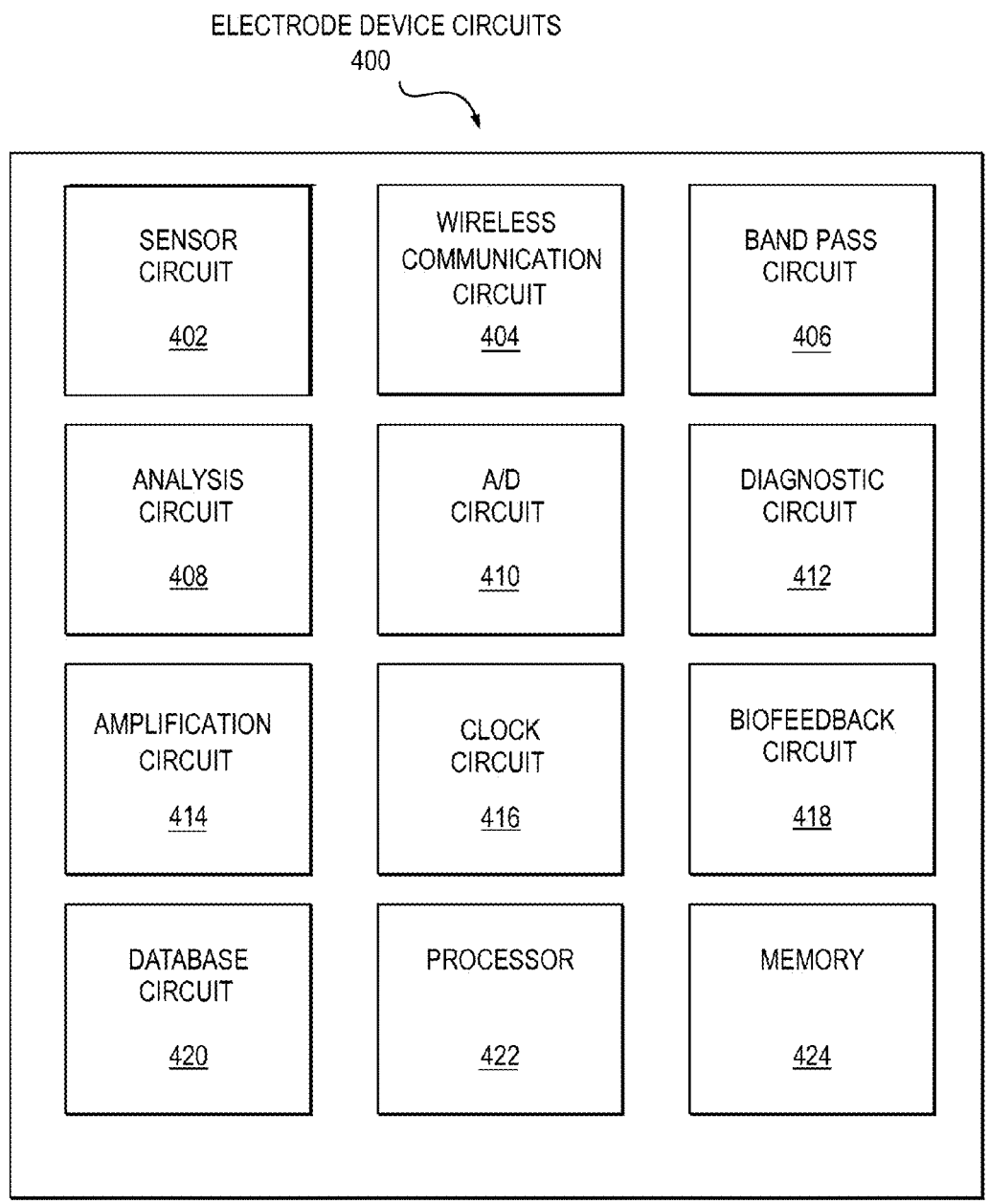
FIG. 4 illustrates a functional view of a system 200 with various circuit modules including a processor and memory to run the software.
Figure 5:
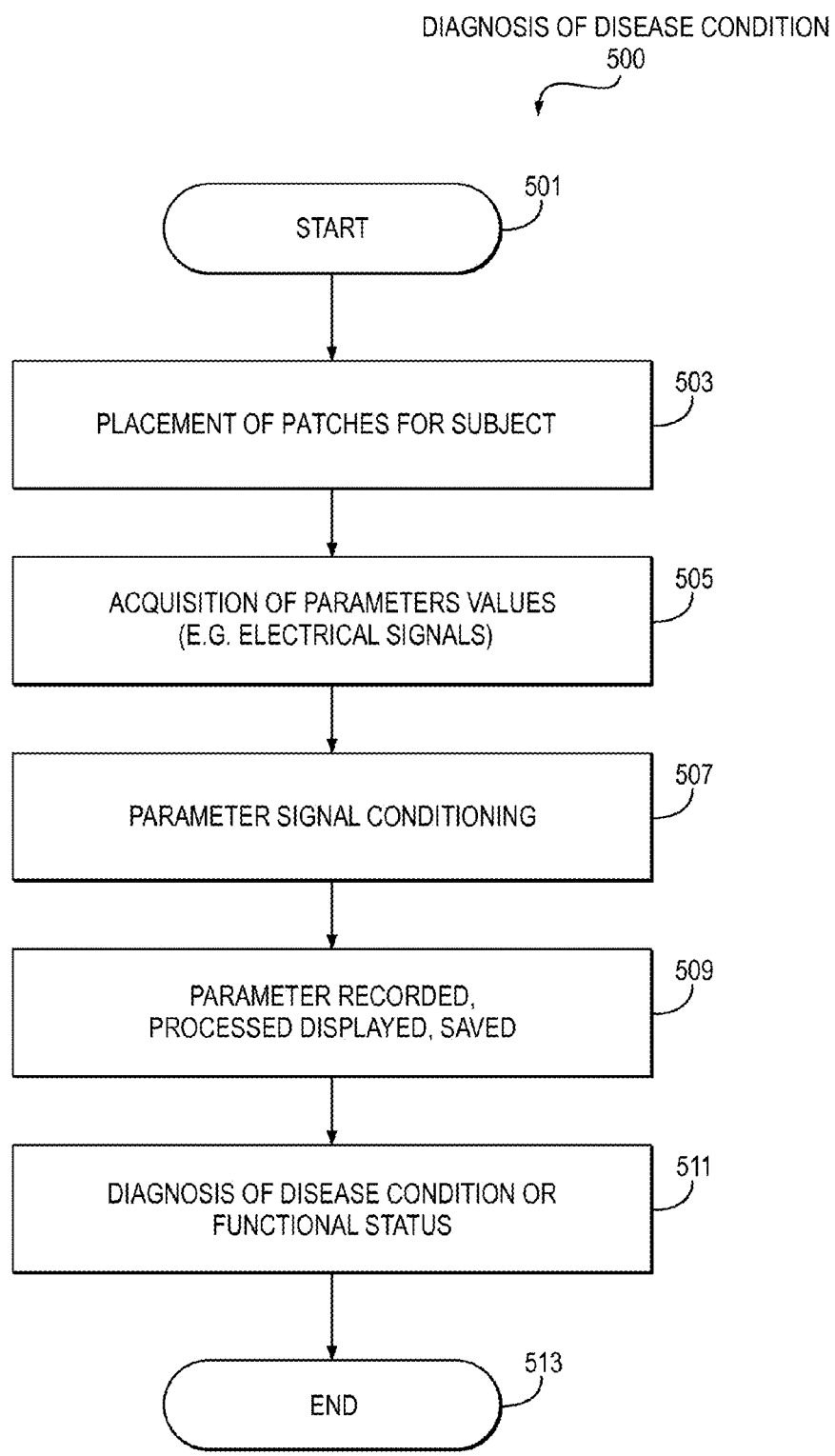
FIG. 5 is a flow chart of the diagnosis process of typical GI disease condition 500.

FIGS. 4 and 5 illustrates flow charts and functional views of the system when in use. For example, an electrode device circuit 400, as shown in FIG. 4, may include a sensor circuit 402, an analysis circuit 408, an amplification circuit 414, a database circuit 420, a wireless communication circuit 404, an analog/digital circuit 410, a clock circuit, 416, a processor 422, a band pass circuit 406, a diagnostic circuit 412, a biofeedback circuit 418, and/or a memory 424.

Further, for example, a method 500 of diagnosing a disease includes: placement of one or more patches on a subject 503; acquisition of one or more parameter values (e.g., electrical signals) 505; parameter signal conditioning 507; one or more parameters recorded, processed, displayed, saved 509; and diagnosis of disease condition or functional status 511.

Figure 6:
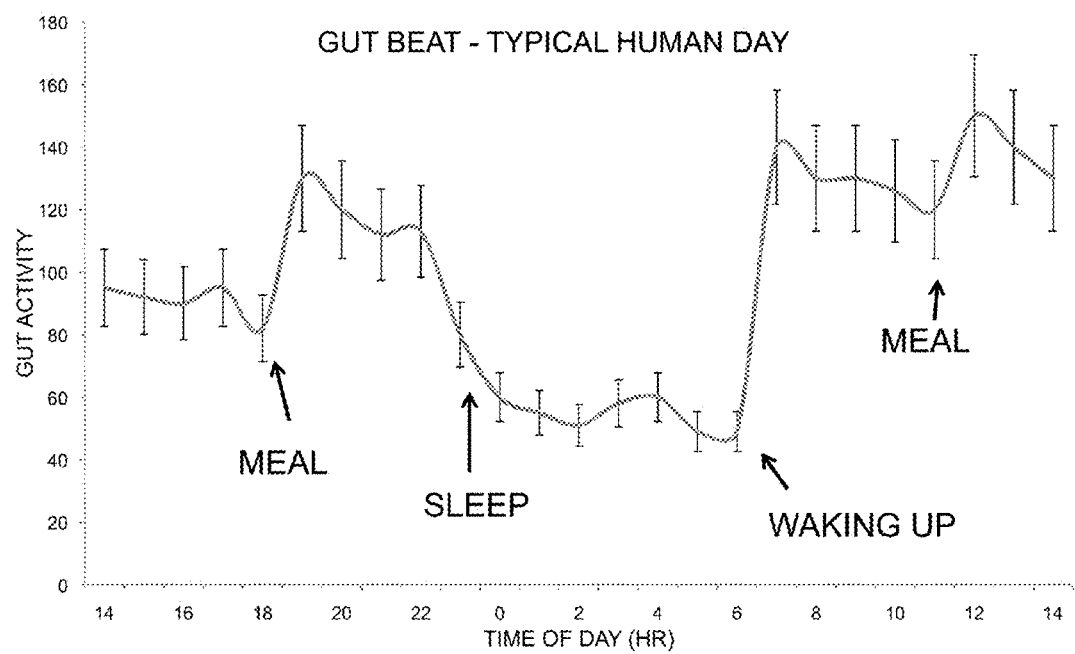
FIG. 6 is a data chart of the typical human daily "Gut Beat", or GI tract activity of a normally behaving person, which is the ideal minimum sample period for maximum GI disorder diagnostic functionality of the presently disclosed invention.

FIG. 6 is a data chart of the typical human daily "Gut Beat," or GI tract activity of a normally behaving person, which is the ideal minimum sample period for maximum GI disorder diagnostic functionality of the presently disclosed invention.

Typical embodiments of a local computing device are sized to be handheld or generally portable. This physical aspect of the device is appropriate for the operation of the system simply because the patient needs to have this local device with himself or herself, or very close at hand, at least substantially throughout the duration of the monitoring period. Typical examples of a local computing device, per currently available technology, include mobile telephones, personal digital assistants, and tablet devices.

Embodiments of a local computing device can communicate through wireless networks by way of cell phone frequencies, satellite communication frequencies, Wi-Fi® networks, or any network that can form a communication route to a networked computing device. Wireless transmission of data to a networked computing device may occur by way of an intervening remote data storage server, such server often referred to generically as "the cloud."

Electromyography is a general term for acquiring or monitoring signals as emanated from physiological sources. Electromyography as applied particularly to the smooth muscle of the gastrointestinal tract from the GI tract can also be termed electrogastrography or electroenterography.

Embodiments of the disclosed system and methods may be applied toward monitoring the electrical activity of the gastrointestinal tract of human subjects of any age, including infants, children, adolescents, and adults. Embodiments may also be applied to monitoring the electrical activity of the gastrointestinal tract of non-human animals, non-human mammals in particular.

Bluetooth LE is a current example of a low energy transmission capability appropriate for operation of the disclosed technology. Other low energy electronic communication protocols that may be developed in the future are included as embodiments. The low energy aspect of communication that the EMG-sensing patches contributes to the ability of a battery to sustain operation of the patches for sustained periods of operation, such as 24 hours or more of continuous monitoring.

An intermittent schedule of signal transmission or transmitting in response to a query is a feature that conserves battery power and contributes to the ability of a battery to sustain operation of the patches for sustained periods of operation, such as 24 hours or more of continuous monitoring. However, intermittent transmission may result in more energy consumed since the wireless connection between the patch and a computing device needs to be reestablished each time data needs to be transmitted therebetween. Therefore, in some embodiments, the data is compressed before transmission to conserve battery power. For example, each raw data file or a subset of data is compressed into a predetermined number of bits. A maximum number of uncompressed bits is typically 24 but may be reduced to 16 or some other number of bits that have been determined to encompass the entire range of values. For example, if values never exceed a particular absolute value threshold, the higher-order data bits that encode for larger values can be dropped from the transmission. Similarly, if very low values are determined to be inconsequential, those lower-order bits can be dropped. This is the equivalent of dividing all values by the lower value limit based on two raised to the number of bits to be dropped, replacing values below one with zeroes and then truncating to the new upper limit.

Alternatively or additionally, transmitted data may only include differences in the data set as compared to one or more previous data files.

Additionally, each Bluetooth enabled patch possesses a unique identifier, so that the EMG sensing patches are able to transmit a unique identifier to the local computing device. This will allow identification of individual patches-both those located on one patient, or those located on different patients or subjects in the same general vicinity.

The unique identifier term, as used herein, generally refers to a serial number, an arbitrary number, or an accession number that is applied to it by the system or by a human operator. This identifier does not necessarily include any location information per se, although location information could be associated with the identifier by a human operator or by an aspect of the system.

It is also advantageous for the operation of the patch that the battery has a high charge capacity. Additionally, embodiments of the technology include any future technological advancements that may be made regarding recharging of batteries, particularly by way of induction or solar power.

The patches, as shown in FIGS. 1-3, acquire myoelectrical data in the form of voltage readings that represent electrical activity of the digestive organs. Inevitably, the electrode patches also sense and record electrical activity from other biological sources, such as the heart and skeletal muscles. Due to the sensitivity required to measure the microvolt level signals from the digestive organs, artifacts can be induced by interactions between electrodes and skin surface, for example by way of transverse slippage or partial separation. At least some of these artifacts can be much larger in amplitude than the signals of interest. Further, these recordings, taken over a period of many hours or even days at frequencies of several Hz or more, and on multiple channels, result in very large data sets, with tens to hundreds of millions of individual readings. Interpreting these data and providing a clinically valuable summary is a significant challenge, which is addressed by the presently disclosed systems using one or more of the methods described herein.

The presence of such artifacts, particularly ones with high amplitude, negatively affects subsequent processing intended to reveal valid physiological data. For example, even a small number of large artifacts can have a profound effect on a frequency spectrum of the data, and makes it difficult to identify rhythmic peaks that relate to the gastrointestinal motor activity of primary interest. Accordingly, a method for identifying and eliminating such artifacts with minimal disturbance of underlying valid gastrointestinal signals in data sets acquired from electrode patches is now provided.

Figure 7:
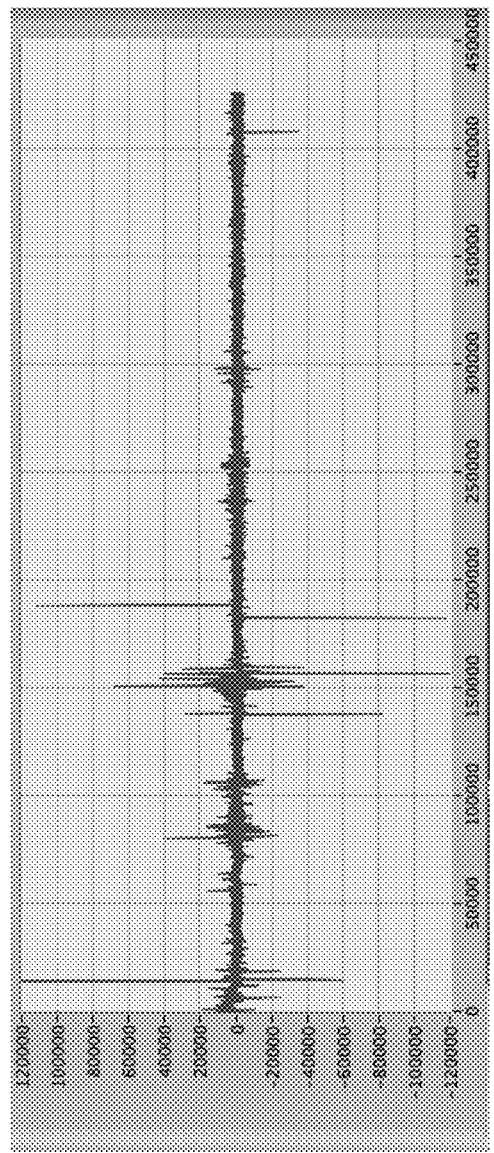
FIG. 7 shows a raw, un-cleaned electrode data set, showing both artifacts and periods of clean data.
Figure 8:
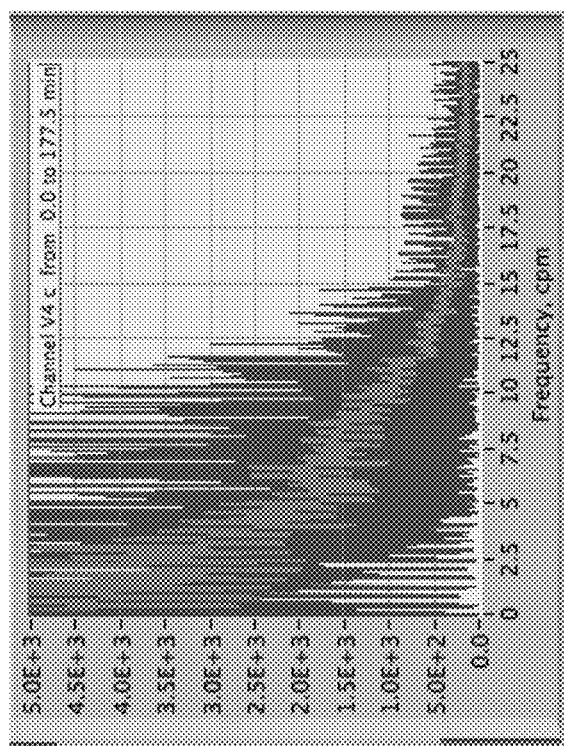
FIG. 8 shows power spectrum of the data set in FIG. 7; the red trace represents a moving average of the blue data series.
Figure 9:
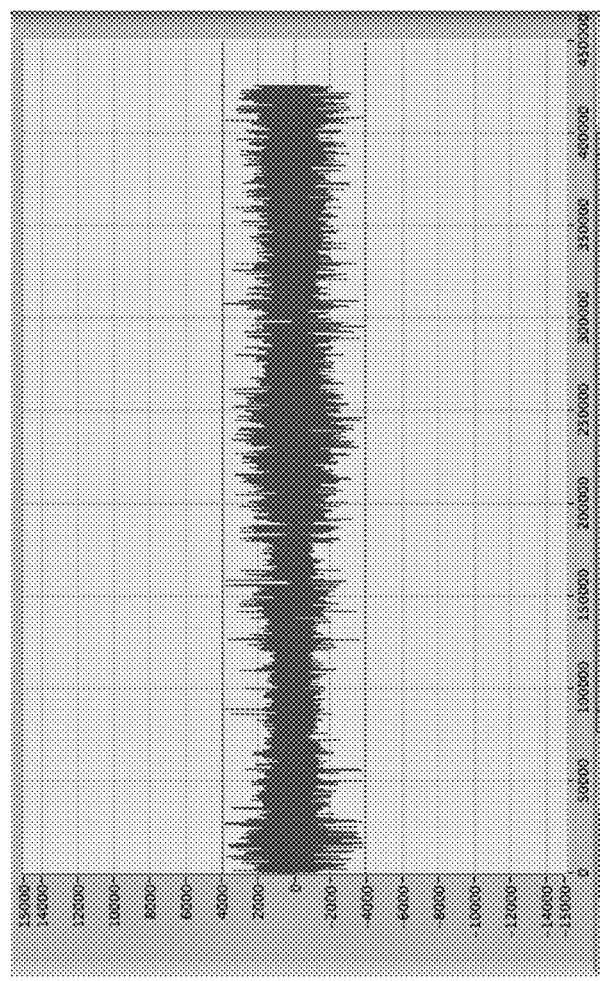
FIG. 9 shows data of FIG. 7 after artifacts have been removed using the methods described herein. Note scale change from FIG. 7.

A representative sample data set is shown in FIG. 7, representing 3 hours acquired at 40 Hz. The vertical axis is amplitude in ADC counts while the horizontal axis is point number representing time. The large amplitude spikes or peaks are artifacts. The data of interest are all contained in the much lower amplitude areas. Note that the number of data points over 400,000 are far more than can be individually discerned due to print or screen resolution; this tends to visually exaggerate the time extent of the artifacts. Nevertheless, the effect of artifacts on the analysis is profound. One of the most useful approaches to interpreting the data is to create a power spectrum by fast Fourier transform (FFT). FIG. 8 shows the power spectrum of the data in FIG. 7. It is lacking in useful information due to the artifacts. By contrast, FIG. 9 shows the data set from FIG. 7 after artifact cleanup (note scale change) and the spectrum in FIG. 10. The cleaned spectrum is substantially different, and it is possible to see structures that are ultimately useful for the purposes of the measurement, for example understanding the motor activity of the gastrointestinal (GI) tract.

Figure 11:
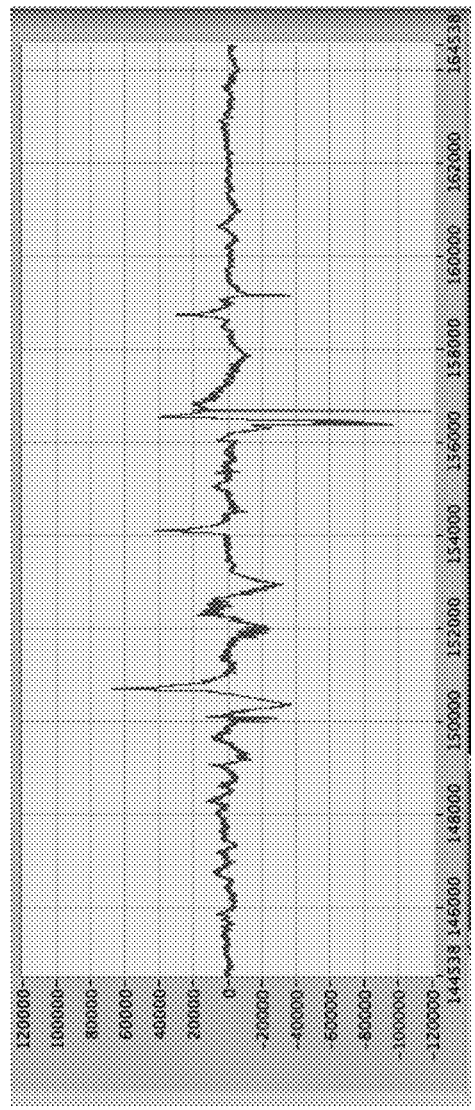
FIG. 11 shows 50 seconds of data showing structure of the artifacts.

By displaying a shorter section of the data one can better see the structure of artifacts and the fact that they come in several different flavors or patterns. FIG. 11 is an example of 50 seconds of data from the same data set. There are approximately five artifacts shown, depending on how the artifact and its extent in time are defined. While some of the large amplitude peaks are easy to identify as artificial, others are less clearly so. The field of gastrointestinal tract diagnosis from surface electrical measurements, in particular, is so new that there is still no clear definition of what is an artifact and what may be an interesting signal. This underscores the importance of maintaining a flexible system for artifact removal.

Figure 10:
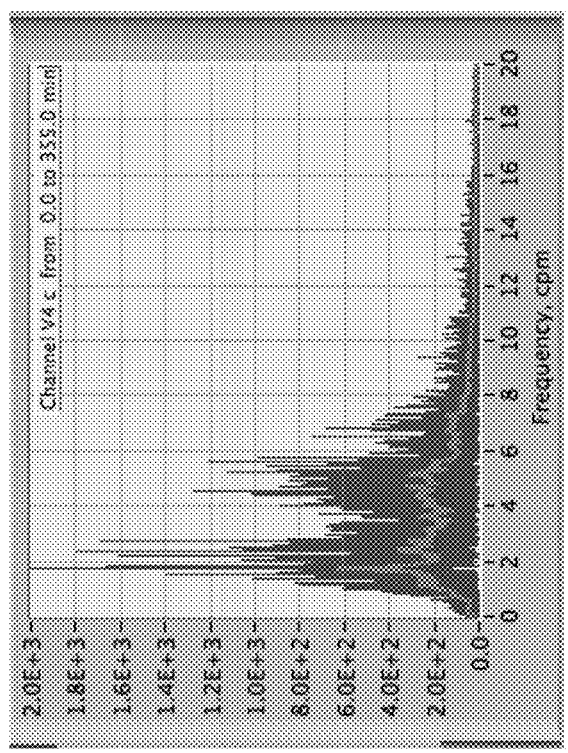
FIG. 10 shows spectrum of cleaned data in FIG. 9. Structures are now evident. Red trace represents a moving average of the raw spectrum shown by the blue data series.

However, while there are many sources and resulting forms of artifacts, there are also some shapes that repeat. FIGS. 9 and 10 show examples of shapes that are often seen, in both cases with inversion of the second relative to the first. Thus, while identification of artifacts is ultimately based largely on amplitude as the primary characteristic, it can also involve shapes of patterns of the event. Not shown in the figures, but occurring occasionally, is a type of simple artifact such as those known to arise from errors in the digitization circuitry of the analog-to-digital (ADC) conversion, which involves a single point of very large positive or negative amplitudes. These artifacts are easy to identify by their amplitude and narrowness and can be eliminated by setting the value to the average of the points on either side. In the case of two or more consecutive points that meet the description, the same identification and resolution may follow.

Measurements of electrical signals from human subjects and other mammals are dependent on many factors, including the quality of the skin, skin preparation, amount of adipose tissue, distance from the source to the measurement point, and so forth. These dependencies lead to significant differences in the amplitude of the signals of interest. Thus, it is impossible to select a single absolute value as threshold for identifying an artifact. Rather, one must use the data itself as a means of determining the threshold. The well-practiced human eye-mind system is quite good at this; one can look at the clean sections of the data and say here is where you should set the threshold, but an automated computer system needs an algorithm with some sophistication to deal with variation between subjects as well as variability during a single test, either between electrodes or as a function of time.

One approach is to use the standard deviation (sigma) of the data, for example setting a threshold such that anything beyond approximately 5-sigma indicates the presence of an artifact. Note that the full extent of the artifact is not specified at the point in the process; depending on one's definition and interest in subsequent processing, only a portion of it may be above the threshold. For data sets with few artifacts, the simple one-pass threshold based on a set sigma value is an effective approach. However, for many data sets seen in practice, the sigma value is strongly influenced by the values carried by artifacts themselves, and the results one obtains after removal among multiple sets will be inconsistent depending upon the number and size of artifacts in each set. A solution to this issue is to remove the artifacts in a first pass, and then repeatedly apply the same criteria as defined in terms of the number of sigmas. As artifacts are removed in each pass, the calculated value of sigma is reduced, and the thresholds approach a value that would be obtained if there were no artifacts at all. For appropriate choice of number of sigma n (but not all), the process converges, that is, after some number of iterations of artifact removal and recalculation of sigma, no points lie outside the n sigma threshold.

That this situation should obtain with data sets of the type under consideration here can be understood by considering limiting cases. For n=2 for example, in a normal distribution, 5% of all points will lie outside this threshold and as the largest values are removed, the sigma calculation will continue to drop with the data values, until no points are left. On the other hand, for an n such that only the very largest amplitude point is included, only a single iteration may be necessary. Not wishing to be bound by theory, in principle, there exists a range of n for which convergence will be achievable. This all depends on the data set having artifacts with much larger amplitude than the data of primary interest, and to some extent the value of n that is chosen will depend on details of the data, including the number of points in the set.

Figure 14:
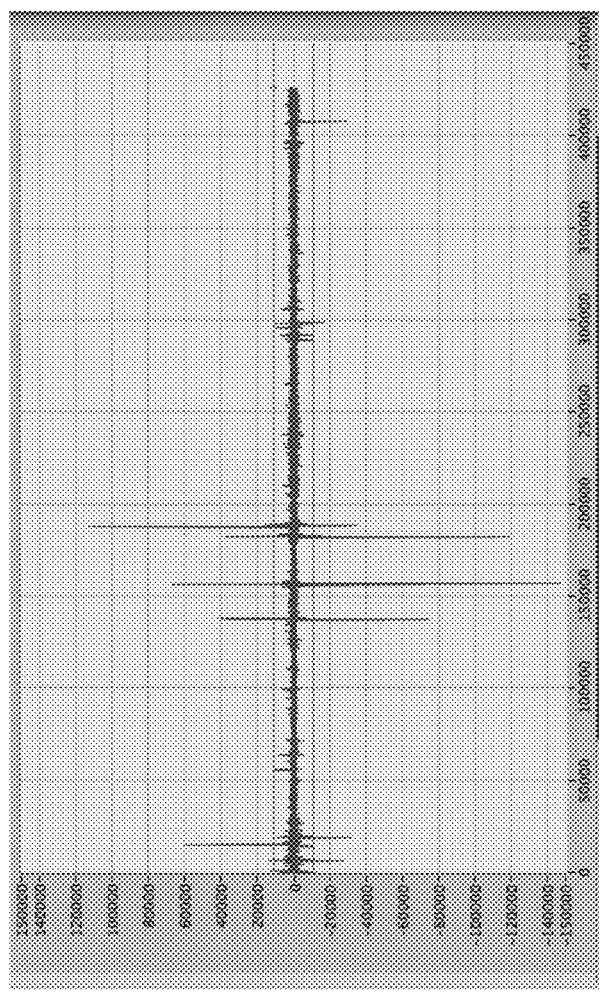
FIG. 14 shows a data set with artifacts; the horizontal cursors indicate 5-sigma thresholds.
Figure 15:
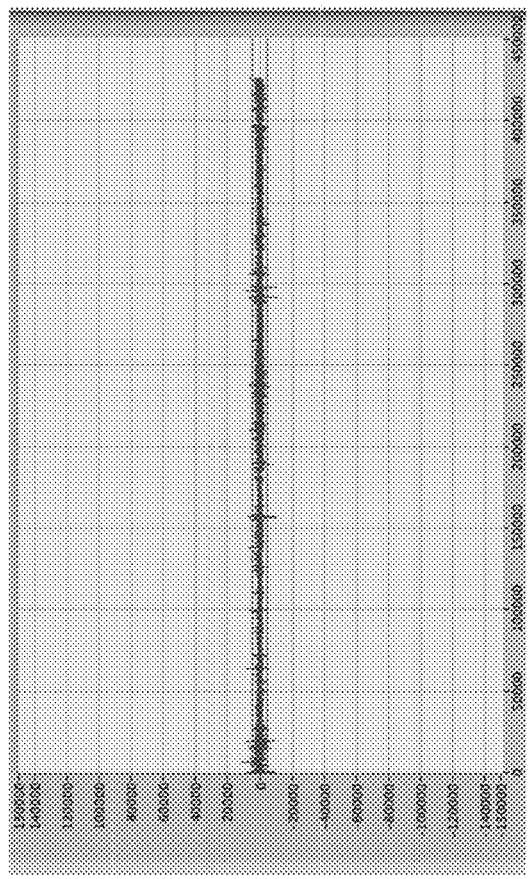
FIG. 15 shows the same data set as FIG. 14 after artifacts have been removed; cursors now show 5-sigma of the new data set.
Figure 16:
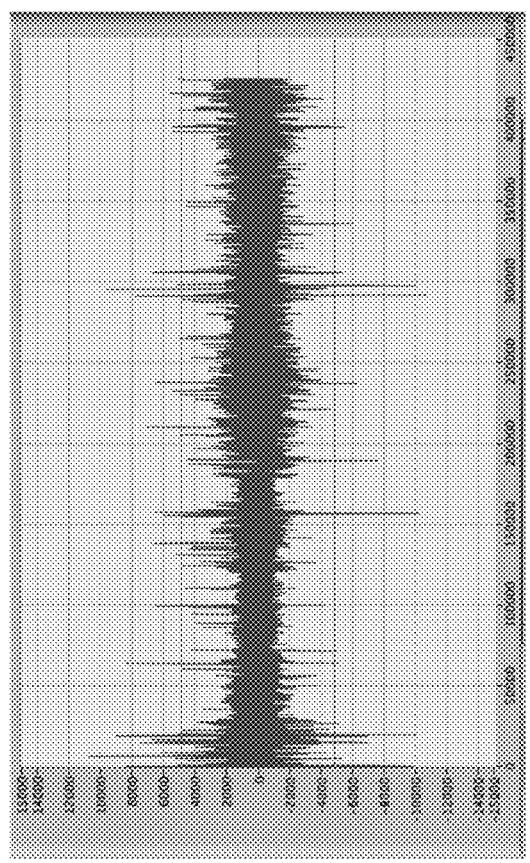
FIG. 16 shows the same data as in FIG. 15, zoomed in to show that artifacts remain, and how the 5-sigma threshold has shifted after first pass artifact removal.
Figure 17:
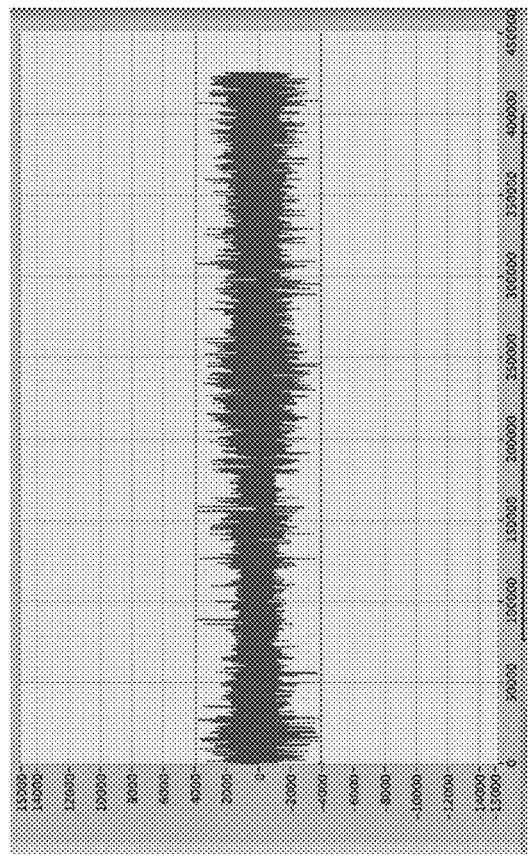
FIG. 17 shows the same original data set as in previous figures, after 6 iterations of artifact removal. Convergence has been achieved; there is no longer any point outside the 5-sigma threshold.

FIG. 14 shows an example of a time series data set where there are several very large amplitude events that are likely artifacts. The red horizontal cursors are set at the level of 5-sigma. The largest artifacts extend well outside the 5-sigma threshold. FIG. 15 shows the result after the artifacts identified by the 5-sigma threshold have been removed, with cursors set at the new 5-sigma level, which has been considerably reduced by the removal of the artifacts. FIG. 16 is the same as the previous FIG. 15, but the vertical scale zoomed in by a factor of 10-fold. Numerous points are now outside the new threshold. After these artifacts are removed, the results are shown in FIG. 17.

It is important to note that although the final threshold value can be arrived at without iteration, for example, by selecting an initial threshold n sigma less than 5, the exact value is not knowable in advance. Each data set has its own characteristics, with the number, width and amplitude of artifacts, level of desirable signal, and so forth. The technique of iteratively removing artifacts using a fixed n allows the process to be used across a wide range of data sets yet lead to consistent results, as for instance measured by the ratio of largest to most probable absolute value.

An alternative approach to setting the threshold that similarly takes into account the values of the data is to use a percentile ranking, for example (negative-going) points that are below 2nd percentile and (positive-going) points above the 98th percentile. Other implementations of this approach include using the absolute value to make all values positive and then identifying artifacts by selecting those points above a given percentile.

Figure 12:
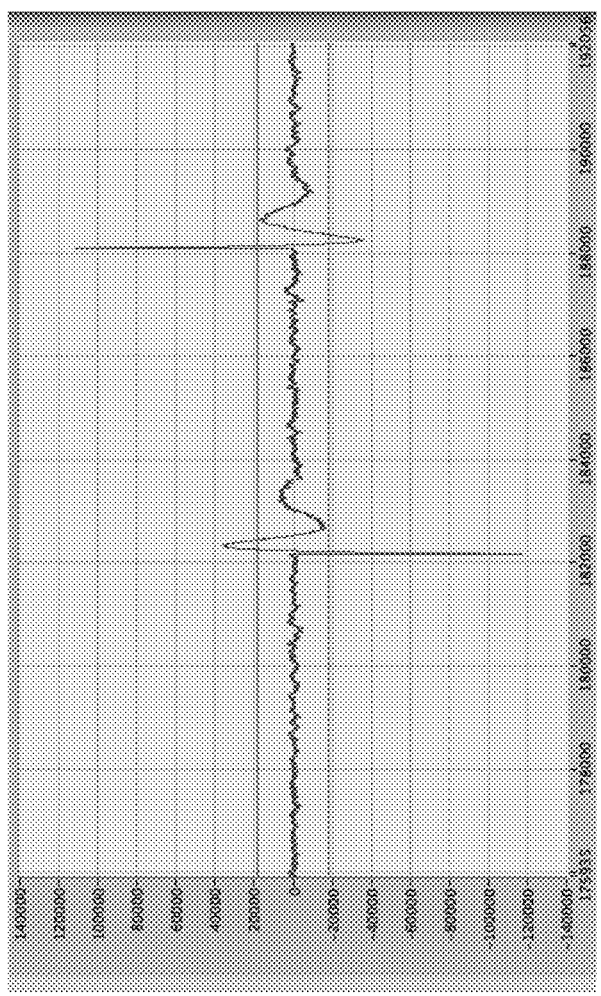
FIG. 12 shows artifacts with a particular shape.
Figure 13:
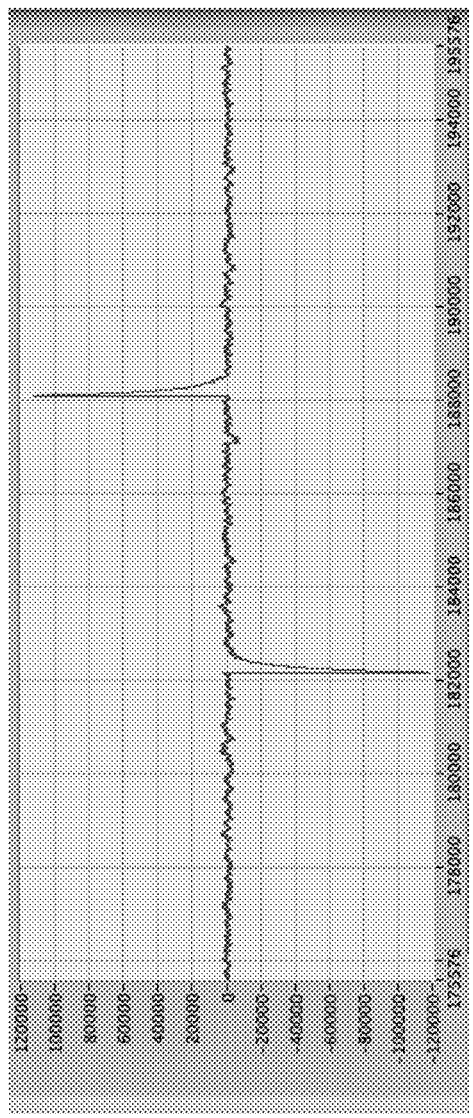
FIG. 13 shows artifacts with another particular shape.

Having identified the existence and location of a (potential) artifact by its amplitude relative to a threshold, it is possible to perform further analysis to shed further light on whether a time series event is indeed an artifact or is actually interesting physiologic data that one would preferably not remove. This is more likely with artifacts that are not much greater than the threshold than those that are, for instance, two or more times larger. One approach is to examine the pattern itself, comparing it to a known database of shapes of artifacts and real physiologic signals. FIG. 12 and FIG. 13 show examples of time series events that are known to be artifacts. It should be apparent that one can devise an algorithm that will establish the likelihood that a shape in question is from a set of artifacts or not, or from a set of known physiologic events or not, and make an automated judgment of whether to classify the event as an artifact or not. In case it is determined to most likely not be an artifact, one can have the algorithm not remove it even though part of it is larger than the amplitude threshold.

An additional source of information on whether a particular event is an artifact or interesting physiologic data is the distribution of its signal across multiple electrodes. Artifacts due to sudden motion, breathing, and skeletal muscle contractions can be distributed across multiple spatially separated electrodes in a recognizably different pattern from physiological signals. For example, if a signal has similar strength across well separated electrodes, it is less likely to be from a gastrointestinal organ than a surface muscle or from shifting of electrodes. Physiological signals typically have a peak channel where the strength is at maximum, and drop off in a gradual manner that has some dependence on the patient and some on the signal itself.

Figure 18:
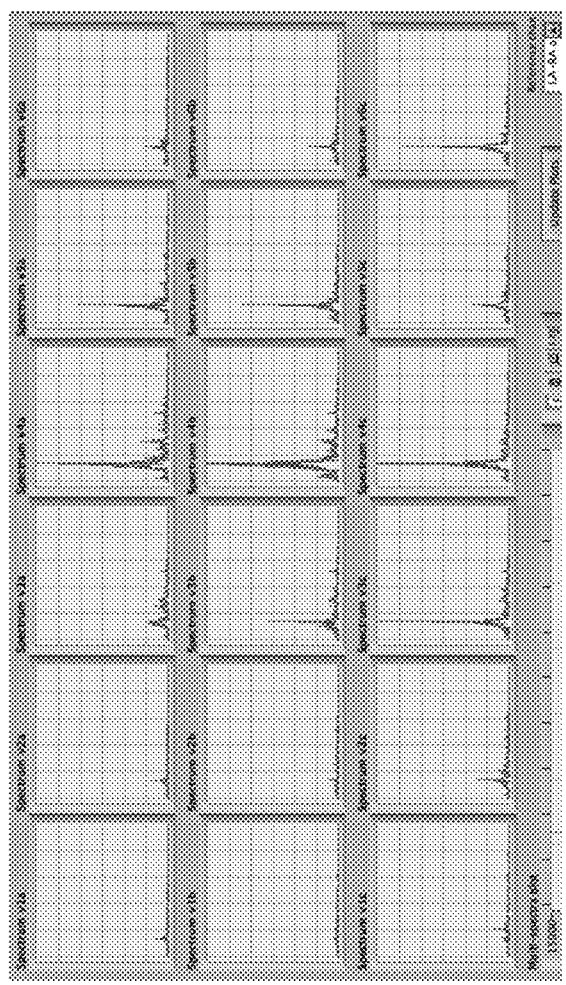
FIG. 18 shows individual Fourier power spectra from 18 electrodes spaced approximately 2 inches apart on subject's abdomen in three rows. The peak at 3 cycles per minute is from the subject's stomach, post meal.
Figure 19:
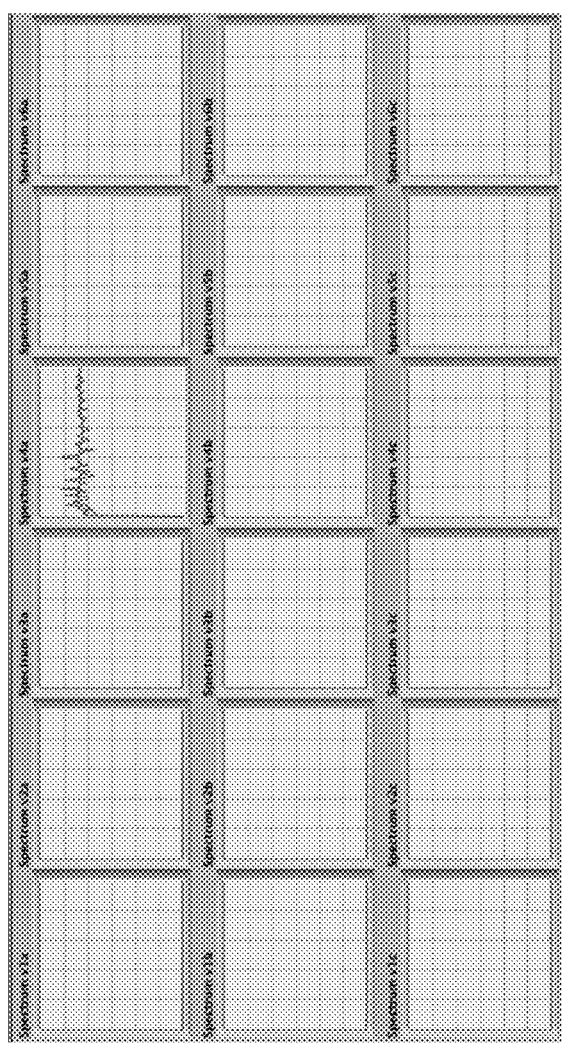
FIG. 19 shows individual Fourier power spectra from 18 electrodes spaced approximately 2 inches apart on subject's abdomen in three rows. Example of an artifact that shows up on only one channel.
Figure 20:
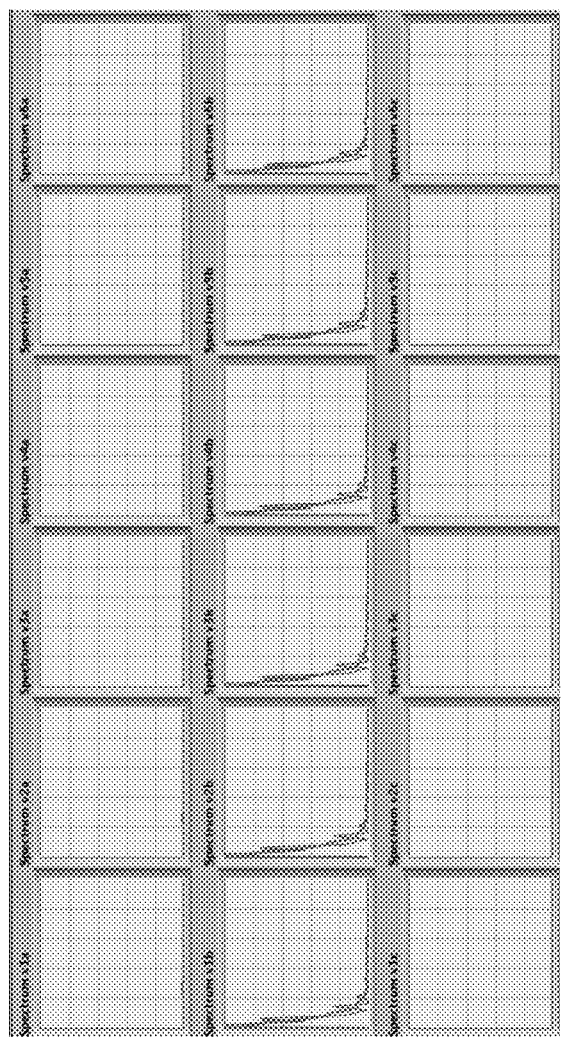
FIG. 20 shows individual Fourier power spectra from 18 electrodes spaced approximately 2 inches apart on subject's abdomen in three rows. Example of an artifact that shows up across a related group of channels.
Figure 21:
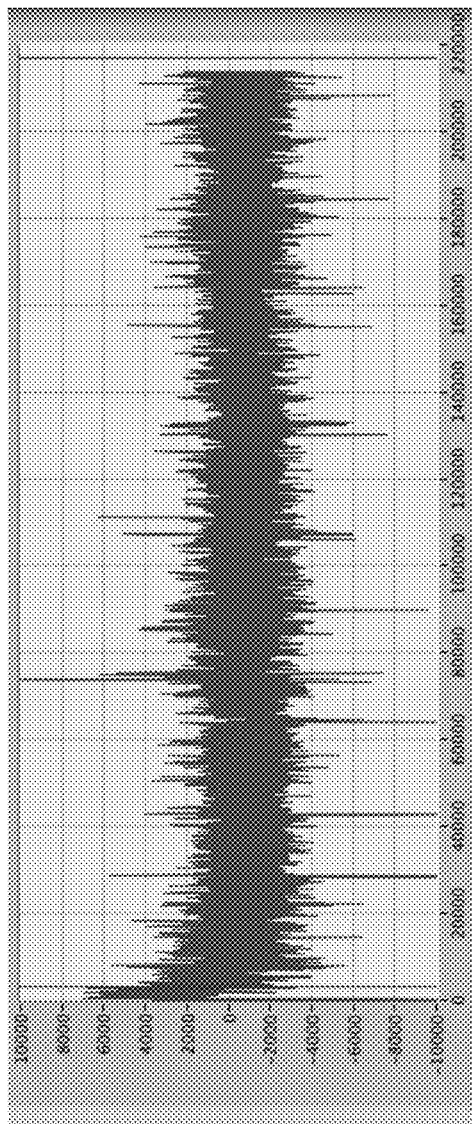
FIG. 21 shows a data set showing drift at the beginning of the test.

FIG. 18 shows power spectra for 18 electrodes placed on a subject's abdomen, in 3 rows of 6 electrodes, spaced approximately 2 inches apart. The peak that is visible at 3 cycles per minute is from the subject's stomach after a meal. While this is not a time series event, it is a real physiologic signal, and shows how such signals may be distributed spatially, with a maximum on one channel and gradually diminishing outwardly. An event that appears on only one channel, or on many channels with similar magnitude, is less likely to be of physiological origin. By contrast, FIGS. 19 and 20 show signals that are the result of artifacts, on only one channel, in FIG. 19, and on a group of related channels, in FIG. 20. It should be apparent from these examples that there are ways to examine and automatically process the distribution of data on multiple channels, whatever the physical arrangement of the channels, which provide independent information on the likelihood that an event is an artifact rather than interesting physiological data.

Once an artifact is identified by having one or more points beyond the chosen threshold, the task remains to remove it. To do so, the extent of its presence beyond the threshold must be determined. At its simplest, the signal can be "clipped," which replaces all the points above threshold by the threshold value. However, this leads to a further set of problems in the spectrum, leaving sharp edges to create high frequency issues and a large low frequency component from the "flat top" clipped section. A somewhat better approach is to set all the values to zero, to avoid the lowest frequency component, but this worsens the edge issues, essentially turning them from sharp corners into knife edges and adding false energy into the high frequency spectrum. What is needed is a way to remove the artifact at its "roots" and replace it with values that are neutral or nearly so in the spectrum.

In this approach, the extent of the artifact is determined by tracking the points on both sides to their roots. For the sake of simplicity, we will assume a positive going artifact, with a data set midpoint of zero. It will be understood that the concept applies equally to negatively pointing artifacts and to data sets that have an average value with a non-zero offset. In this case, the roots are at or near zero. Since the data are in discrete points, not a continuous function, it is highly unlikely that there will be a point with a value of exactly zero, but it will always be possible to find two points where a zero-crossing location can be interpolated between them. In this way, the extent of the artifact can be defined by the last (on the time axis) zero crossing before the artifact crosses threshold, and the first zero-crossing after it.

However, inasmuch as there is a great deal of noise in some signals, the zero crossing as recorded may not be in the same location as in a noise free system, and this will give rise to inaccuracies in removing the artifact, either too little or too much being removed. To minimize the effect of noise, a filter can be applied to a copy of the data, for example a double sided moving average filter, or any other type of filter that removes high frequencies with little or no phase shift. This filtered copy is used to determine the location of the zero crossing, and the original data set is then processed using the location so determined. Typically, one would use the point closest in time to the zero-crossing location, but one could also intentionally introduce an offset in either direction to define either narrower or wider removal zones according to what one hopes to accomplish subsequently.

Once the extent of the artifact is determined, the next task is to replace it or simply remove it. Removal is inherently simple but introduces complexities in tracking the timing of later events, and if multiple channels of data are involved, either ruins the synchronization between them or forces the removal of all time periods that have an artifact on any channel, which may eliminate an unnecessary and excessive amount of data. It is desirable therefore to replace the artifact with values that have a neutral effect on the spectrum. In one approach, all values are set to zero (or the mid-point if the average of the data set is non-zero) from the closest point to the zero-crossing on either side of the artifact. In another approach, the values in between the remaining edge points are linearly interpolated, leaving a slight slope. In a slightly more complex implementation, some number of points on either side of the artifact are smoothed and joined to the central section of all zeroes.

Figure 23:
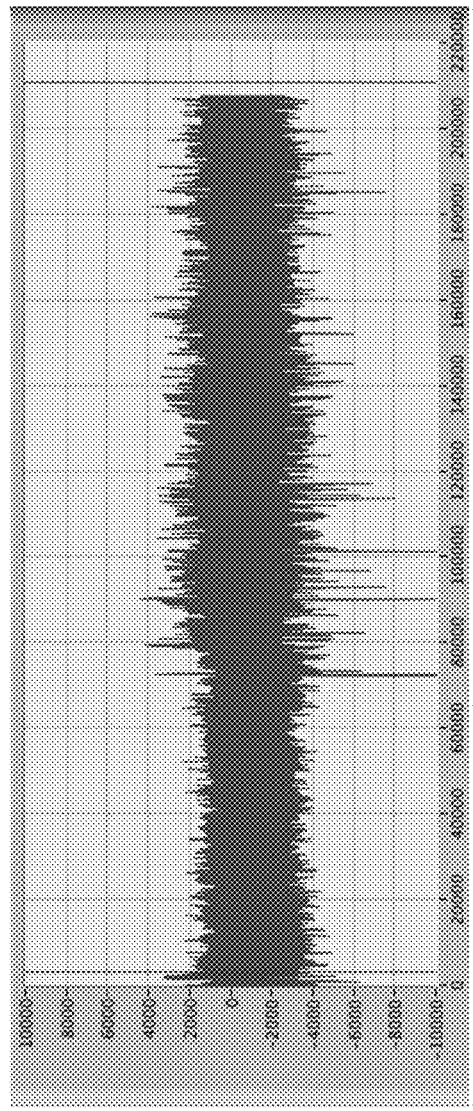
FIG. 23 shows a data set showing bias toward negative numbers due to high frequency repetitive signals.

Data sets that have very low frequency drift, whether only at the beginning or on a continuous basis, can present challenges to setting thresholds if the amplitude of the drift is not negligible compared to the amplitude of the signals of interest. In such cases, it is advantageous to apply a digital high pass filter at a very low frequency. Preferably, the filter cutoff frequency will be well below the frequencies of interest, for example at 0.5 cpm, and with a low order (steepness) to minimize the inevitable phase shifts that are the result of filtering. Artifacts that are of the single data point, large amplitude type discussed earlier are best eliminated prior to such high-pass filtering as they will otherwise lead to a smearing of the artifact onto subsequent data points that are otherwise uncorrupted. Similarly, it can be advantageous to apply a digital low-pass filter to the data prior to the artifact removal step, to eliminate relatively high frequency signals such as those from heartbeats, which tend to bias the positive-negative symmetry and complicate the application of threshold determining schemes such as those based on a given number of standard deviations. FIGS. 18 and 19 show an unfiltered data set and the same set filtered, respectively, with a high pass first order filter at 0.5 cpm. FIG. 23 shows a data set with bias toward negative values, in this case from heartbeat signals, while in FIG. 24, a 4th order low-pass filter at 120 cpm has eliminated the bias. In both examples the unfiltered data set would compromise the effectiveness of the artifact threshold setting and ultimately set a lower limit on the amplitude of artifacts that could be eliminated.

Another method of artifact removal may comprise using one or more machine learning models (e.g., decision tree model) to identify and/or remove artifacts. Currently available methods struggle to remove low amplitude artifacts that remain embedded in the raw data, even after other artifact removal methods, and masquerade as rhythmic gastrointestinal peaks in the spectral analysis. Further, currently available methods fail to establish the ground truth of the amplitude of an observed rhythmic signal. The present approach includes an optimization method which allows for estimation of the amplitude of the signal by observing the spectral peak height at different amplitude cuts.

For example, artifact removal methods described elsewhere herein are used to train and develop ML based decision tree models configured to recognize and classify artifacts based on characteristics and features that may include, but are not limited to, amplitude, periodicity or frequency of rapid variations, and overall shape of the envelope. Training may include testing on multiple copies of the base data set created by applying different amounts and/or types of filtering to show what the same artifact looks like under different filtering scenarios. The ML model may then be used to identify artifacts in subsequent data sets, particularly in data sets where the amplitude requirement is relaxed but while retaining other features to allow detection of lower amplitude artifacts without eliminating good or useful data. These methods may be used independently and/or to augment existing artifact removal methods described elsewhere herein.

For example, one or more machine learning models may be trained on various types of artifacts that are routinely observed in the raw data (e.g., signals coming from heartbeat, local sensor movement, body movement, other body sounds, respiration, etc.), such artifacts being more difficult to parameterize analytically. As a basis, the one or more machine learning models may be trained to recognize and classify artifacts based on characteristics and features that may include amplitudes, periodicity or frequency of rapid variations, and/or overall shape of the envelope. Then, over time, the one or more machine learning models will learn to not only identify the high amplitude artifacts but also those of lower amplitude. The artifacts may then be classified, for example, as occurring in a certain frequency range, occurring with a certain pattern, occurring at a particular time of day, observed when certain other peaks are occurring, etc. The classification of the artifacts may lead to better understanding of the artifacts that are occurring, their distribution, etc. and allow parameterization of the artifacts or other analytical methods to be developed for artifact detection.

Figure 52:
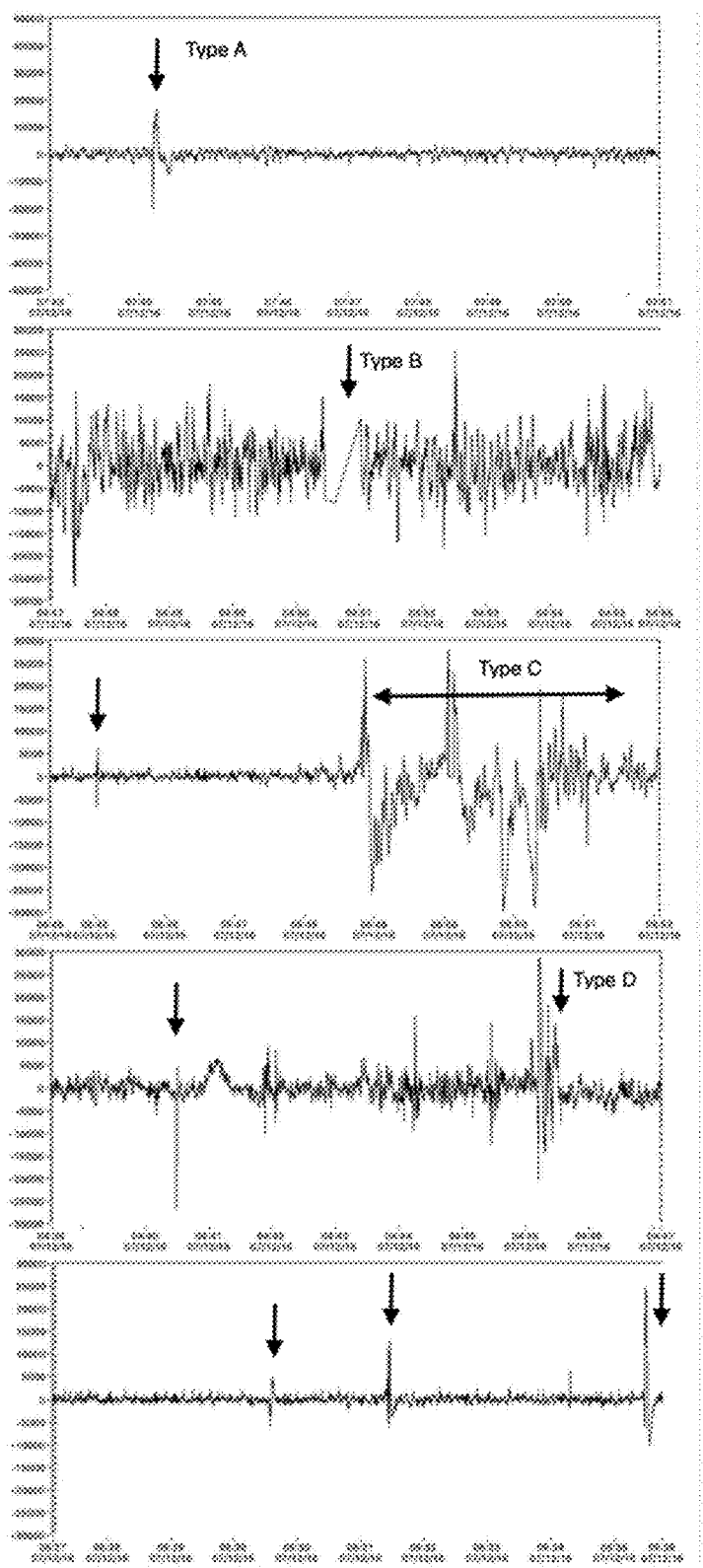
FIG. 52 shows non-limiting examples of training data that include types of artifacts commonly observed in the gastrointestinal myoelectrical time series raw data.

In some embodiments, the one or more machine learning models may comprise a deep neural network model trained on a data set having known artifacts to perform "feature recognition" to classify artifacts and non-artifacts within the raw data. Training may include testing on multiple copies of the base data set created by applying different amounts and types of filtering to show what the same artifact looks like under different filtering scenarios. The machine learning model may then be used to identify artifacts in subsequent data sets, particularly in relaxing the amplitude requirement but retaining other features to allow detection of lower amplitude artifacts without eliminating good or useful data. FIG. 52 shows non-limiting examples of training data that include types of artifacts commonly observed in the gastrointestinal myoelectrical time series raw data, labeled as Type A, Type B etc. The training data may include multiple examples of each type with varying parameters such as rise time, artifact height, and duration. The artifacts may also be provided as filtered and unfiltered under different filtering scenarios (e.g., high pass filtered at 10 cpm). Similarly, the training data may include the corresponding spectral peaks across the different artifact types.

Figure 46:
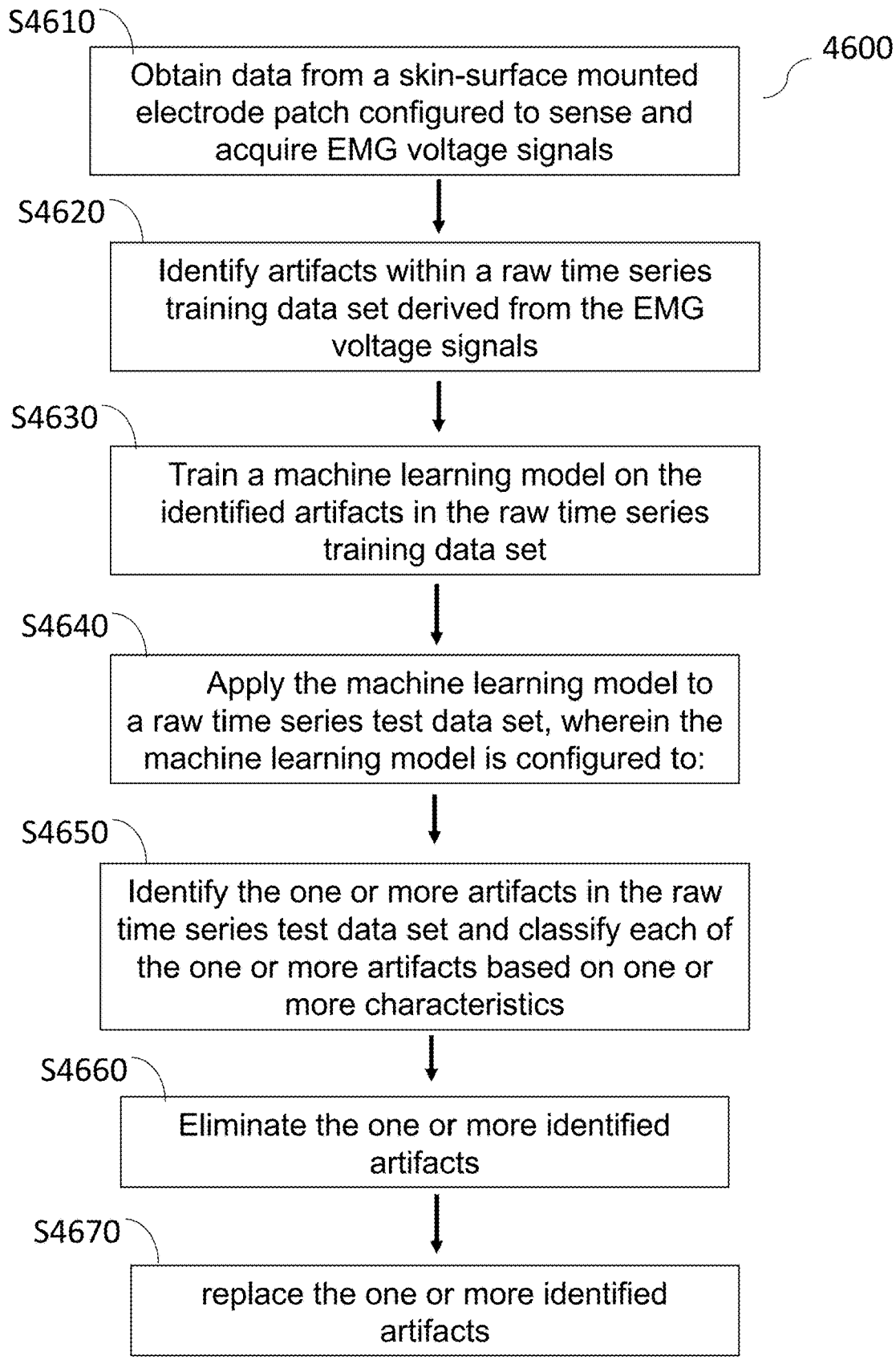
FIG. 46 shows a flow diagram of a method of extracting valid gastrointestinal tract EMG data from a raw time series data set using a machine learning model trained to identify artifacts.
Figure 48:
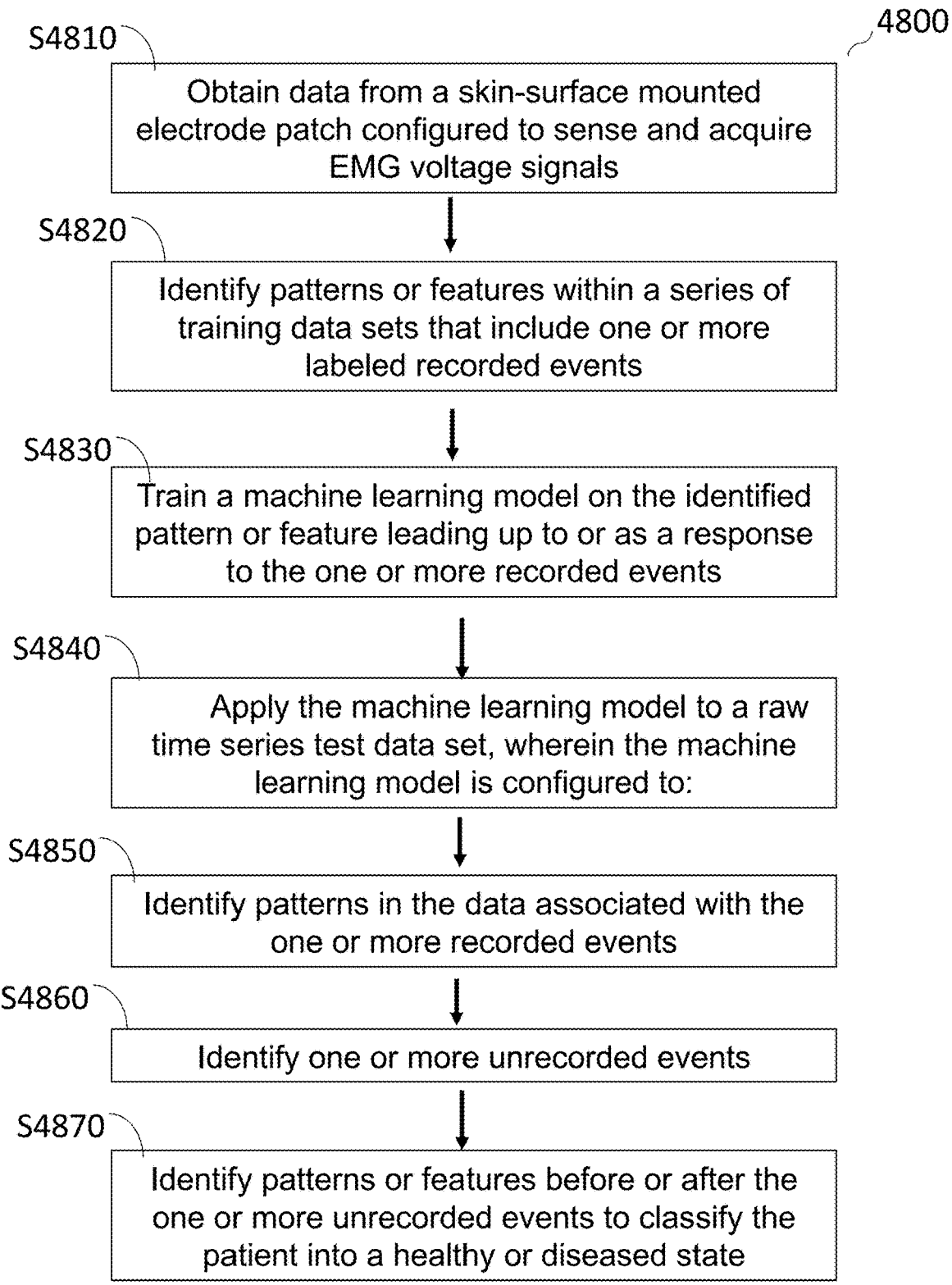
FIG. 48 shows a flow diagram of a method of extracting valid gastrointestinal tract EMG data from a raw time series data set using a machine learning model trained to, at least in part, identify patterns associated with one or more recorded events.

Various solutions for the above-mentioned problems are shown in FIGS. 46 and 48. For example, as shown in FIG. 46, a method 4600 of extracting valid gastrointestinal tract EMG data from a raw time series data set acquired from a skin-surface mounted electrode patch includes: obtaining data from a skin-surface mounted electrode patch configured to sense and acquire EMG voltage signals at block S4610; identifying one or more artifacts within a raw time series training data set derived from the EMG voltage signals at block S4620; training a machine learning model on the identified artifacts in the raw time series training data set at block S4630; and applying the machine learning model to a raw time series test data set at block S4640. The machine learning model is configured to: identify the one or more artifacts in the raw time series test data set and classify each of the one or more artifacts based on one or more characteristics of the one or more artifacts, for example an amplitude, a periodicity of variations, a frequency of variations, a shape of the envelope, or a combination thereof at block S4650; eliminate the one or more identified artifacts from the raw time series test data set at block S4660; and replace the one or more identified artifacts at block S4670.

In some embodiments, the identified artifacts comprise a set of data points nominally centered timewise on a point of largest excursion from an average value of zero-crossing and extending toward an average or zero-crossing.

In some embodiments, each identified artifact includes one or more characteristics comprising one or more of: an amplitude, a periodicity of variations, a frequency of variations, and a shape of an envelope. In some embodiments, these characteristics are unique to each identified artifact.

In some embodiments, eliminating comprises tracking the one or more identified artifacts down to any of a zero-crossing or a midpoint-crossing point on either side of a high amplitude artifact.

In some embodiments, replacing includes replacing the one or more identified artifacts with any of interpolated points or constant value points that span a gap across the eliminated artifacts to create a clean time series data set comprising the valid gastrointestinal tract EMG signals.

Further, as shown in FIG. 48, a method 4800 of extracting valid gastrointestinal tract EMG data from a raw time series data set acquired from a skin-surface mounted electrode patch includes: obtaining data from a skin-surface mounted electrode patch configured to sense and acquire EMG voltage signals at block S4810; identifying patterns or features within a series of training data sets that include one or more labeled recorded events (e.g., meals, bowel movements, sleep, pain, etc.) at block S4820; training a machine learning model (e.g., supervised learning) on the identified pattern or feature leading up to or as a response to the one or more labeled recorded events at block S4830; and applying the machine learning model to raw time series data, frequency spectrums, peak data, or a combination thereof at block S4840. The machine learning model is configured to: identify patterns in the data (e.g., raw, spectrum, peak, etc.) associated with the one or more recorded events (e.g., as meals, BM, sleep, pain, etc.) at block S4850; identify the one or more recorded events (even in event that it is not identified by the patient) at block S4860; and identify patterns or features before and/or after the one or more recorded events to classify a patient into a healthy or diseased state at block S4870.

In some embodiments, the training data set comprises either a series of raw EMG voltage signals or a series of sequentially computed frequency spectrums or sequentially computed frequency peaks leading up to and/or in response to one or more recorded events.

In some embodiments, each of the recorded events may include unique patterns comprising one or more of: a peak frequency or a combination of peak frequencies and/or amplitudes leading up to and/or in response to the events across healthy or disease conditions. Non-limiting examples of patterns include: weak or strong stomach signal following a meal event, high activity in any organ associated with a pain event, colon or small intestine activity before or after a bowel movement event, diurnal changes in activity in the colon or other organs, etc.

For any of the artifact removal methods described above, multiple input data files may be used such that different levels or different types of artifact removal are performed on each raw data input file. Artifacts are removed from each channel in each file and thus peaks are revealed that may be attributed to any of the GI organs. For example, a first file may be cleaned up to 40,000 and thus reveal a first set of GI peaks, a second file may be cleaned up to 20,000, which may remove a subset of the first set of GI peaks detected in the first file, but a second set of GI peaks may become evident in the second file. As such, all the files or a subset of the files may be compared to find the best peaks representative of each GI organ for a particular time period.

Alternatively or additionally, multiple data input files may be used to identify additional information of interest, for example peak width compared to the expected width for a particular organ and/or frequency, a scaled amplitude (i.e., ratio of peak to background), and/or a noisiness (i.e., high frequency variability) of the peak and/or nearby background. One or more machine learning models (e.g. random forest) may be deployed to operate by constructing a multitude of decision trees with varied combination of these parameters and test them against a hand-curated set of peak data to determine the rank for each of these parameters in order to determine the best peak or indicative peaks(s) in subsequent data sets.

Figure 50:
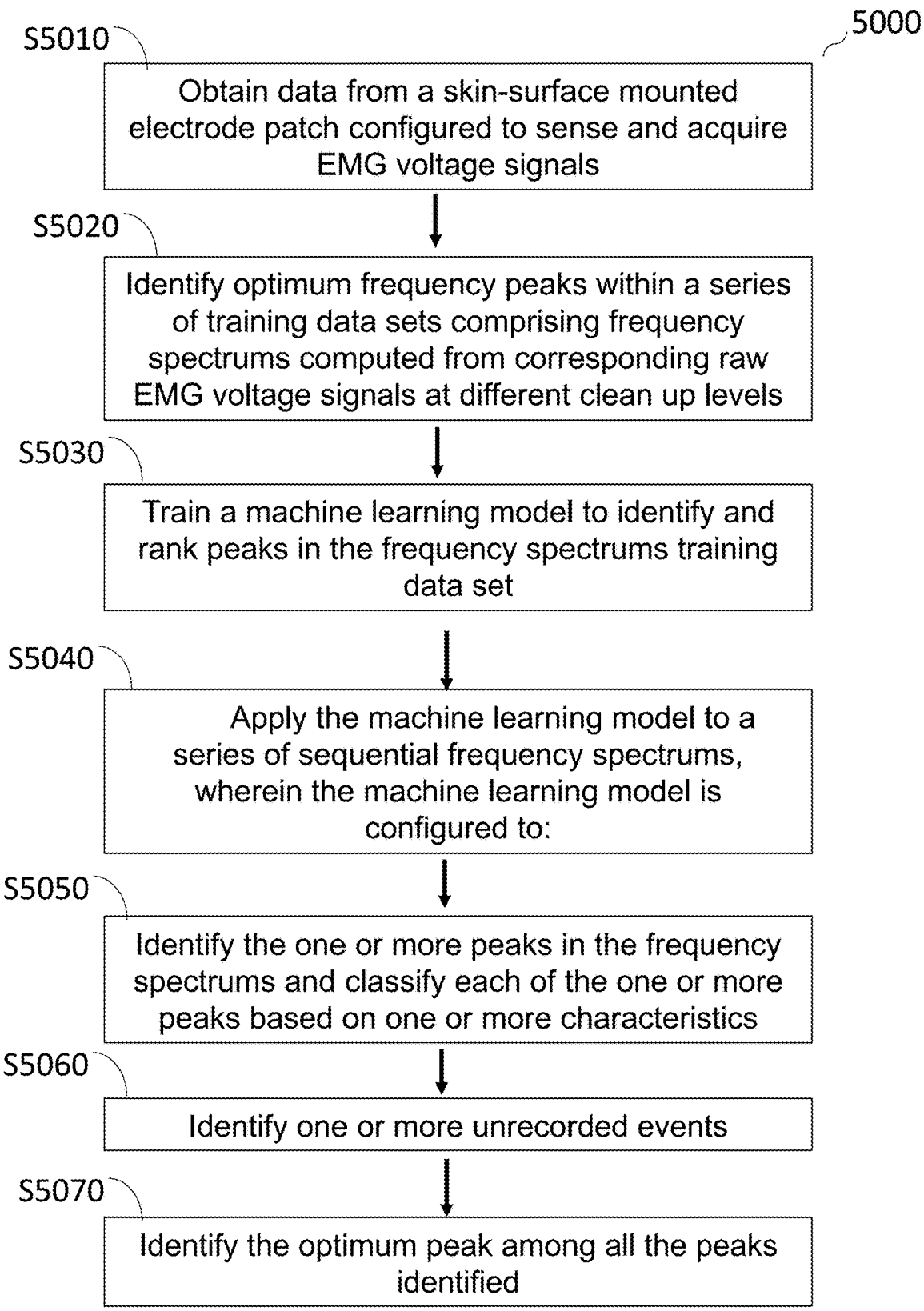
FIG. 50 shows a flow diagram of a method of extracting valid gastrointestinal tract EMG data from a raw time series data set using a machine learning model trained to, at least in part, identify and classify one or more peaks in an EMG frequency spectrum.

As shown in FIG. 50, a method 5000 of extracting valid gastrointestinal tract EMG data from a raw time series data set acquired from a skin-surface mounted electrode patch includes obtaining data from a skin-surface mounted electrode patch configured to sense and acquire EMG voltage signals at block S5010; identifying optimum frequency peaks within a series of training data sets comprising frequency spectrums computed from corresponding raw EMG voltage signals at different clean up levels at block S5020; training a machine learning model to identify and rank peaks in the frequency spectrums training data set at block S5030; and applying the machine learning model to a series of sequential frequency spectrums at block S5040.

Figure 53:
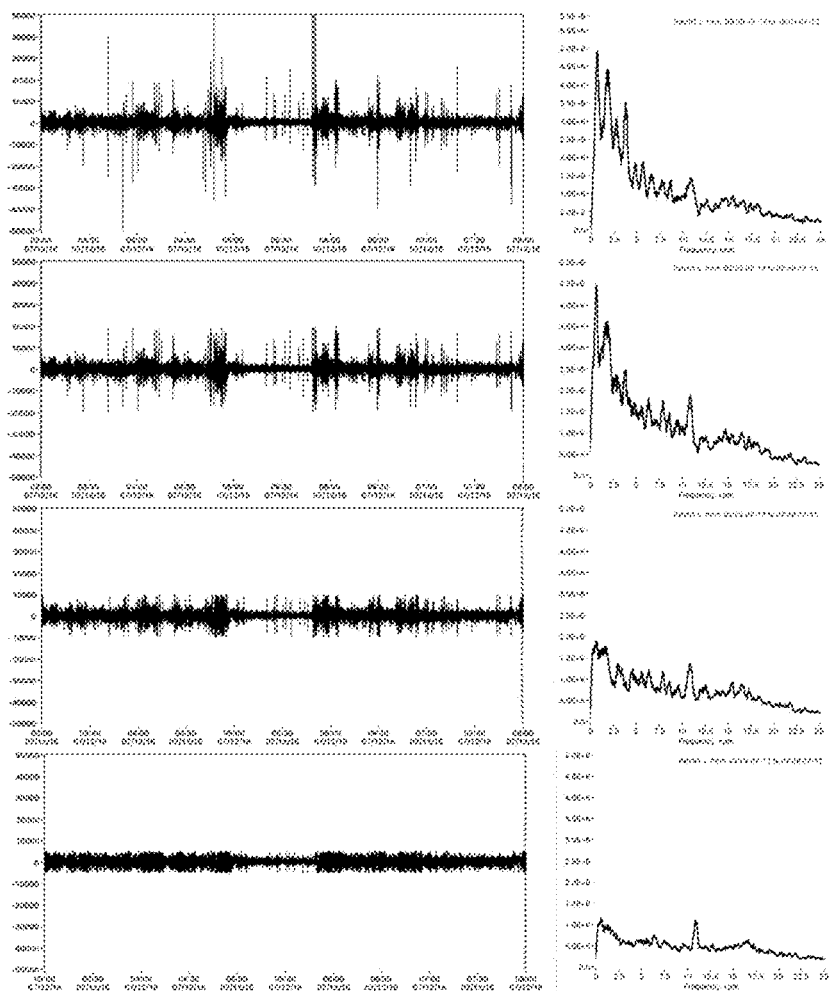
FIG. 53 shows examples of labeled training data that include differing height of frequency peaks achieved by performing signal clean-up across levels.
Figure 54:
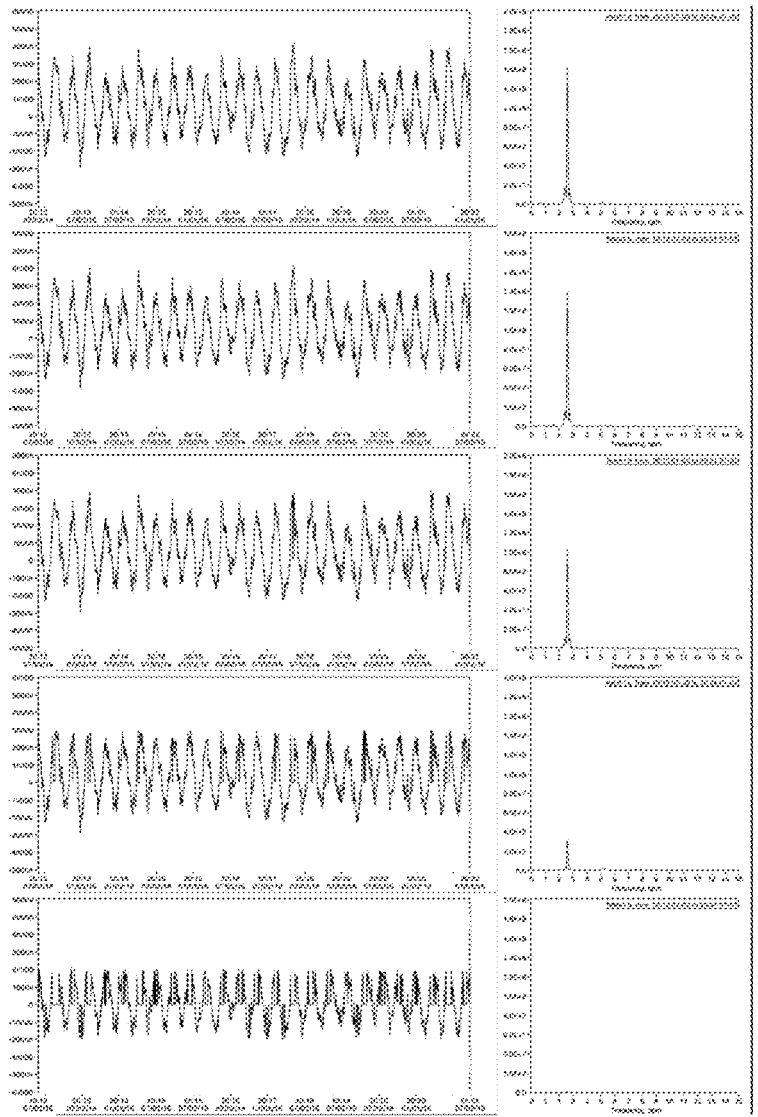
FIG. 54 shows examples of labeled training data that include differing height of frequency peaks achieved by performing signal clean-up across levels.

FIGS. 53-54 show examples of labeled training data that include differing height of frequency peaks achieved by performing signal clean-up across levels. In one non-limiting example, an optimum peak could be defined as the peak at a particular clean-up level that achieves the highest ratio of peak height to baseline. In FIG. 54, for example, an optimum peak may be achieved in the first figure itself but as the signal gets cut, the peak starts to diminish.

The machine learning model is configured to: identify the one or more peaks in the frequency spectrums and classify each of the one or more peaks based on one or more characteristics at block S5050; identify one or more unrecorded events at block S5060; and identify the optimum peak among all the peaks identified at block S5070.

In some embodiments, the identified peaks include a set of data points nominally centered timewise on a point of largest excursion above the background value and extending back.

In some embodiments, each identified peak includes unique characteristics comprising one or more of: a peak width compared to an expected width for that organ and/or frequency, a scaled amplitude (e.g., ratio of peak to background), a noisiness (e.g., high frequency variability) of the peak and/or nearby background, and a combination thereof.

The machine learning model may include a random decision forest that may operate by constructing a multitude of decision trees with varied combinations of these parameters and testing them against a hand-curated set of peak data to determine the rank for each of these parameters in order to pick out the best peak in subsequent data sets. A non-limiting example of a best peak would be a peak with the highest ratio of peak to background while achieving the expected width specific to the organ of interest. For example, a stomach peak would be expected to have a narrow peak in contrast to a peak in the colon range which may be broad in nature.

The overall strength of the signals obtained from the organs of the body through the layers of tissue and skin surface depends not only on the signal source itself, but also on details of the layers in between electrodes and source. The thickness and quality of tissue layers, the quality of skin and its preparation, and the coupling of the electrode to the skin all can have significant impact on the signal strength.

In order to make meaningful comparisons of signals obtained from a given subject against a standard or set of other subjects, it is necessary to take into account the individual sources of overall signal strength variability, and eliminate patient-to-patient variability as much as possible, and allow a clear comparison between any given patient and a well characterized normal population. Accordingly, a method for normalizing the recordings so that the effects of tissue layers and skin quality from patient-to-patient are mitigated is provided herein.

Figure 22:
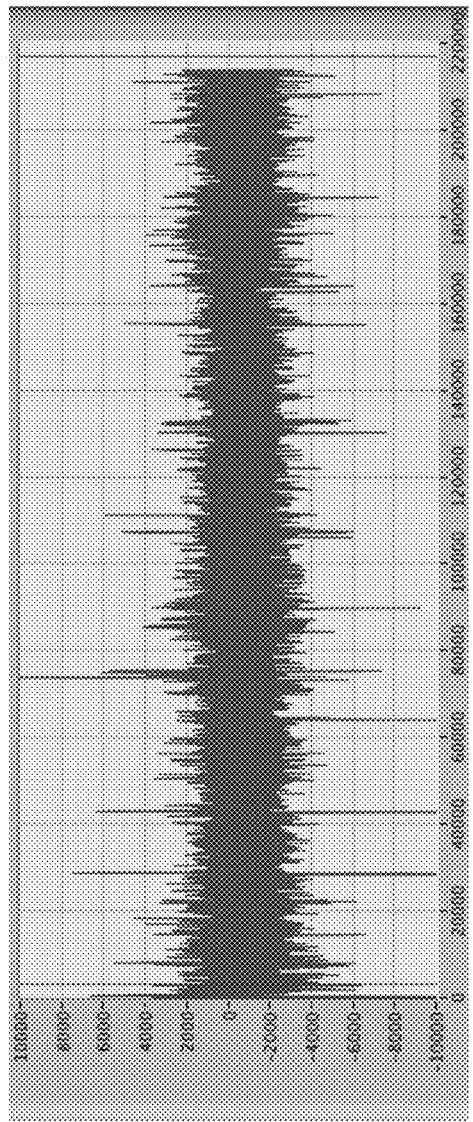
FIG. 22 shows the same data set as in FIG. 21 but with high-pass filter applied to remove drift.
Figure 24:
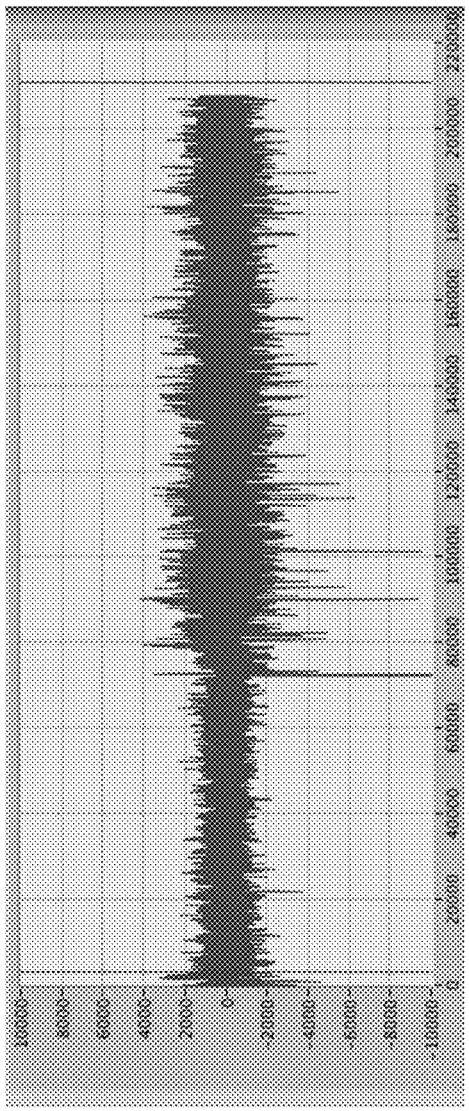
FIG. 24 shows the same data set as in FIG. 23 but with low-pass filter applied to remove negative bias.
Figure 25:
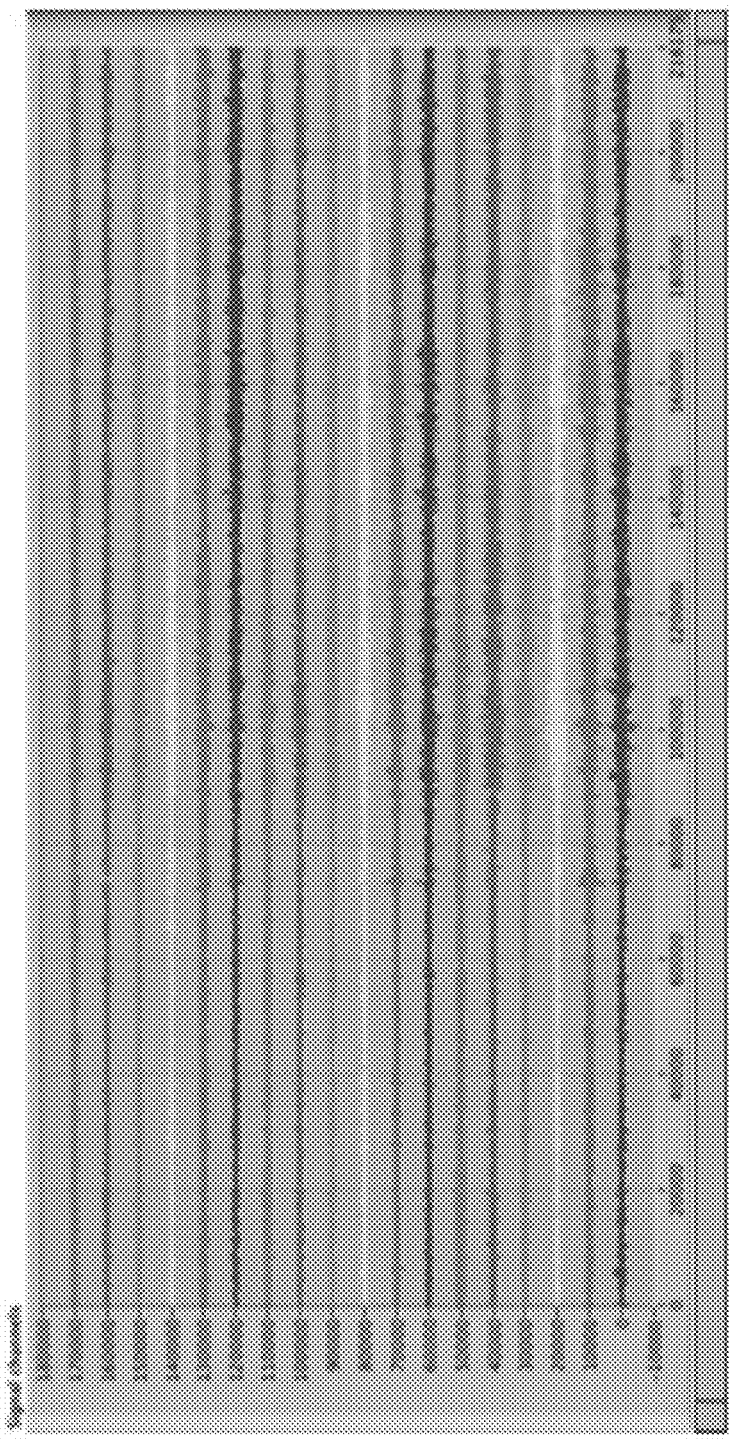
FIG. 25 shows a data set from Subject 027 before data normalization.
Figure 26:
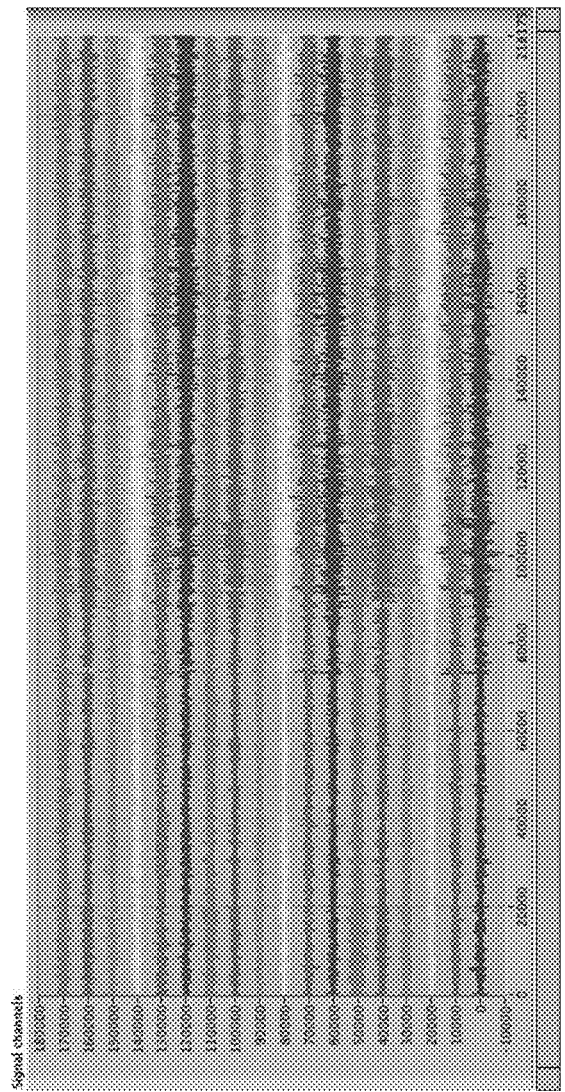
FIG. 26 shows a data set from Subject 027 after data normalization.
Figure 27:
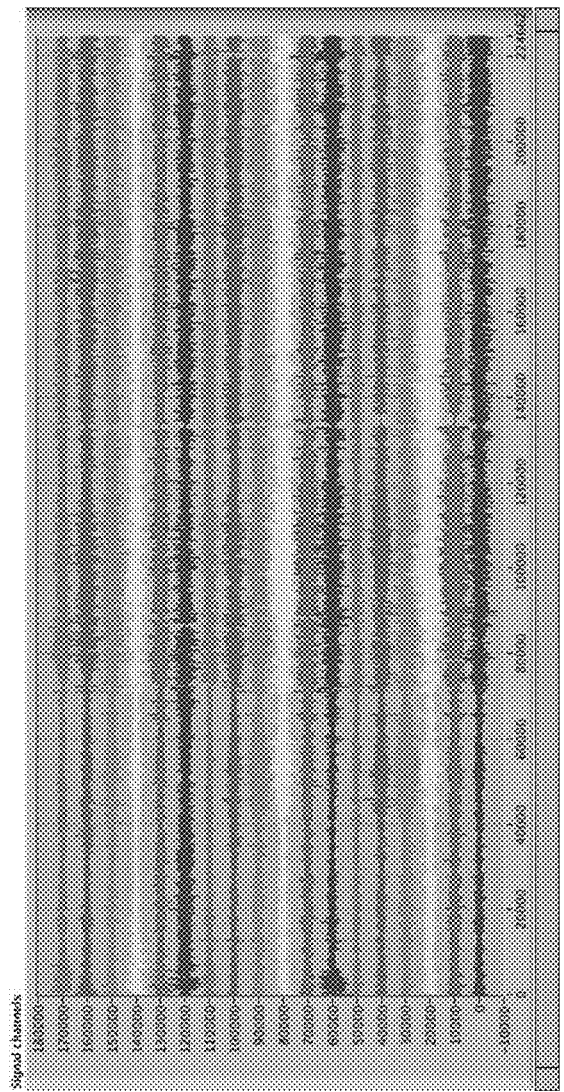
FIG. 27 shows a data set from Subject 013 before data normalization.
Figure 28:
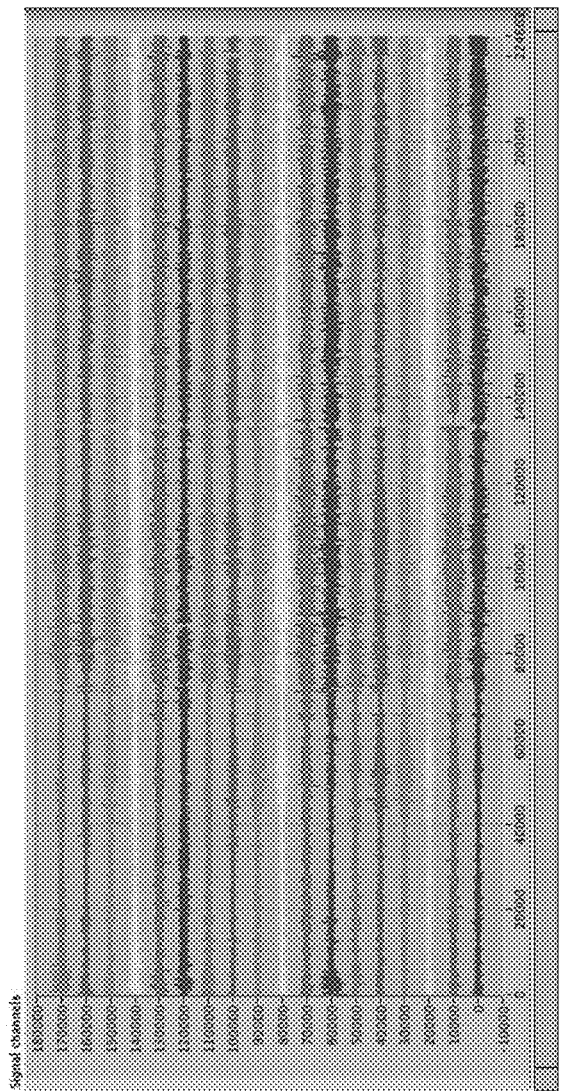
FIG. 28 shows a data set from Subject 013 after data normalization.

FIGS. 22-27 show time series data on 18 channels from electrodes placed in a matrix on the abdomen of three subjects, representing 3 hours of data at 20 Hz. The data, as shown, are filtered outside of the range 0.5 to 25 cpm (cycles per minute). FIGS. 22, 24 and 26, show data from the 3 subjects before normalization; FIGS. 23, 25 and 27 show the same data from each of the subjects, respectively, after normalization, using the range from 25 to 45 cpm to determine the normalization factor. Although the amplitudes of the signals in FIGS. 22, 24 and 26, are quite different from one another, after normalization, the data in FIGS. 23, 25 and 27 are much more similar to each other. Spectral quantities based on the data sets, such as the height of peaks and the baselines between peaks, are much more consistent after normalization. The values of the multiplicative normalization factors in these examples are 2.10, 1.45 and 0.53, respectively.

Figure 31:
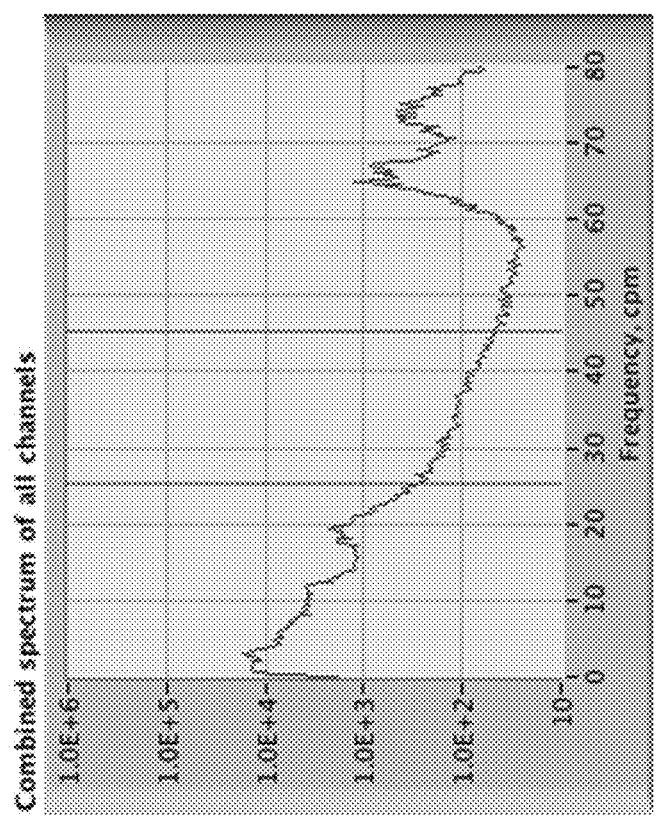
FIG. 31 shows spectra of all channels showing quiet region from 25 to 45 cycles/min (cpm) flanked by structures on either side.
Figure 32:
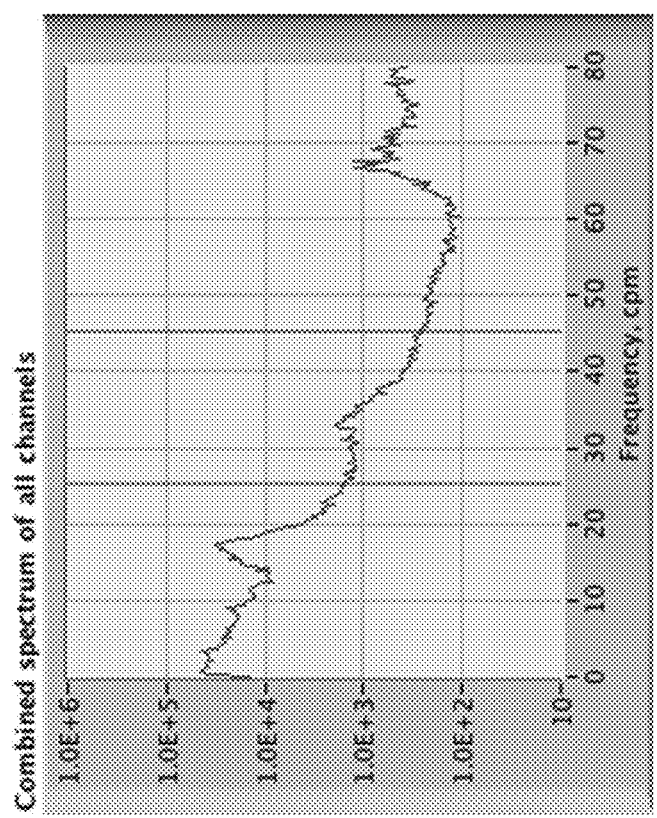
FIG. 32 shows a spectrum with a peak in the 25 to 45 cpm region from harmonics of the 16 cpm primary peak.
Figure 33:
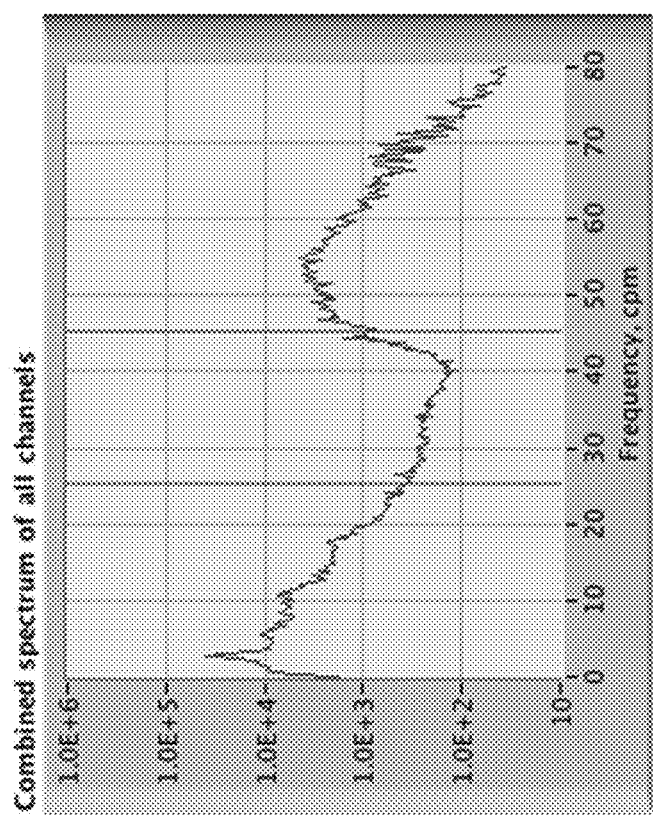
FIG. 33 shows a spectrum with energy in the 25 to 45 cpm region from the lower edge of the heartbeat peak.

In the examples shown in FIGS. 22-27, the normalization factor was determined by integration of the spectrum of each channel of data over the range 25 to 45 cpm, divided by a standard value that was the mean of a set of such measurements, followed by a square root operation. The range chosen for this example has a generally uneventful spectrum, carrying a certain amount of random noise, but above the signals of interest from the gastrointestinal tract and below those typically seen from the heartbeat. A spectrum example is shown in FIG. 31 where the red cursors indicate the region of interest (ROI). Without such signals confounding the data, this region is appropriate for determining the degree of electrical coupling of the electrodes through the skin and tissues to the internal organs.

Figure 29:
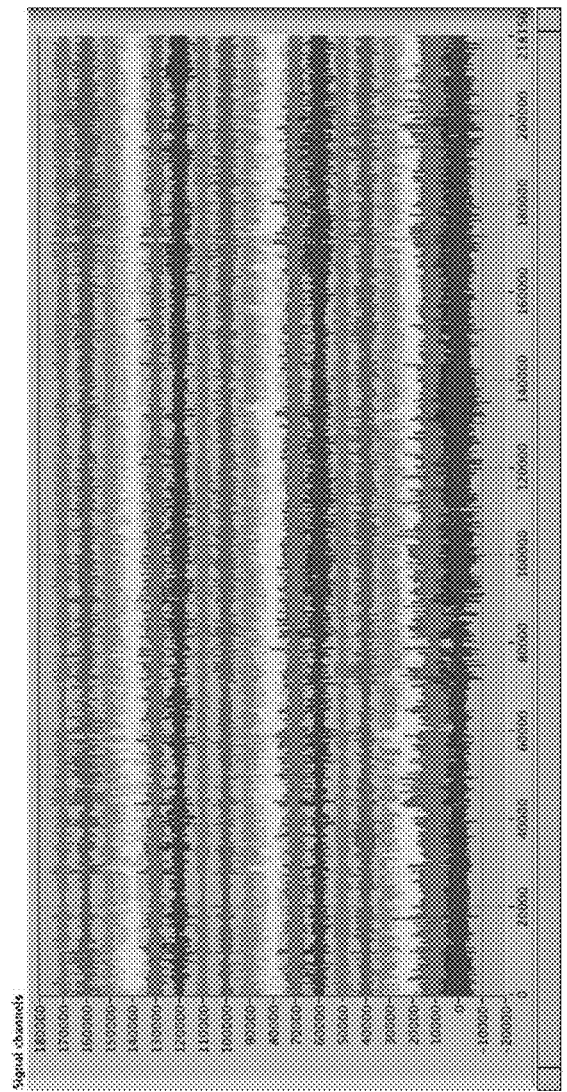
FIG. 29 shows a data set from Subject 012 before data normalization.
Figure 30:
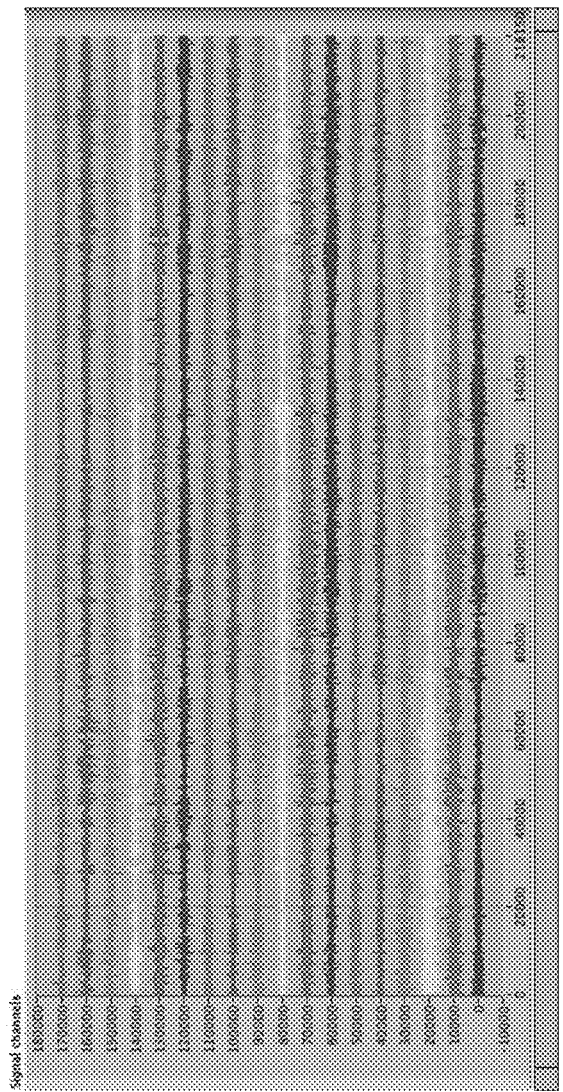
FIG. 30 shows a data set from Subject 012 after data normalization.

However, it is not always the case that the aforementioned or any other predetermined range will be free of these subject-dependent structures. FIGS. 29 and 30 show an example where a harmonic of the 16 cpm peak adds energy to the region, and where the patient's heartbeat is unusually low for part of the test and does the same. Since these structures are specifically dependent on the patient and add energy to the spectrum, they bias the normalization factor and introduce inaccuracies in any parameter derived from a comparison between this patient's results and that of others, such as a percentile ranking of activity.

In order to determine the most accurate normalization factors it would be valuable (advantageous to) to avoid the types of structures shown in FIGS. 29 and 30 when identifying a region of data as a quiet data region. While the eye and brain together provide a powerful tool for achieving this result, it is desirable to have the process automated by a computer algorithm. One such approach involves determining a local slope parameter, essentially a derivative but filtered to remove high frequency components. Note that in FIG. 31 the spectrum in the sample's region of interest, or portion thereof, has a simple and well-defined behavior, in this case a downward slope with some gentle upward curvature.

It is possible to define a range of slope values that represent "quiet" behavior over a region of interest, and to use this range to specify the limits of a region of interest for use in normalization. Further, it is possible to additionally use the curvature as determined by the second derivative as additional criteria. One method of doing so involves specifying a range of derivative and second derivative values and selecting a contiguous region that meets the criteria, the region being chosen from a larger region that is known to be a good candidate region, i.e. avoiding the frequencies where peaks of interest are known to appear, for example the larger region might be the 25 to 45 cpm shown in the examples, but could also be a larger or smaller region, or one entirely different.

A more sophisticated method for selecting the region of interest involves using a range of acceptable slope and second derivative values defined on a local basis that would be narrower. For example, the ranges could be defined for each cycles/minute (cpm) value based on expected behavior calculated from a set of measurements that were visually identified as being acceptable and appropriate. This approach has the benefit of being more precise and is easily performed by a computer algorithm.

Figure 34:
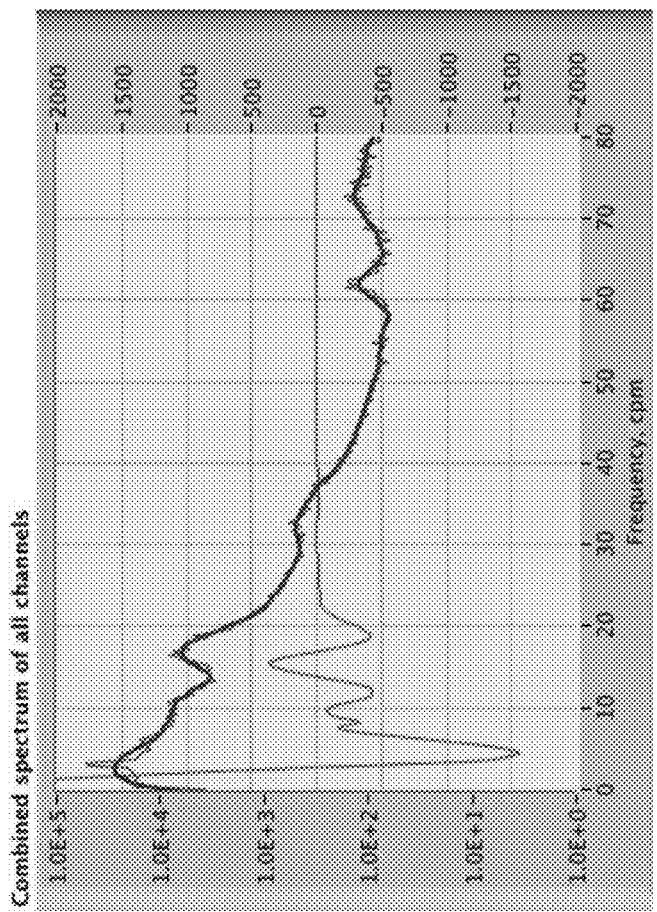
FIG. 34 shows a spectrum in blue and derivative in red.
Figure 25:
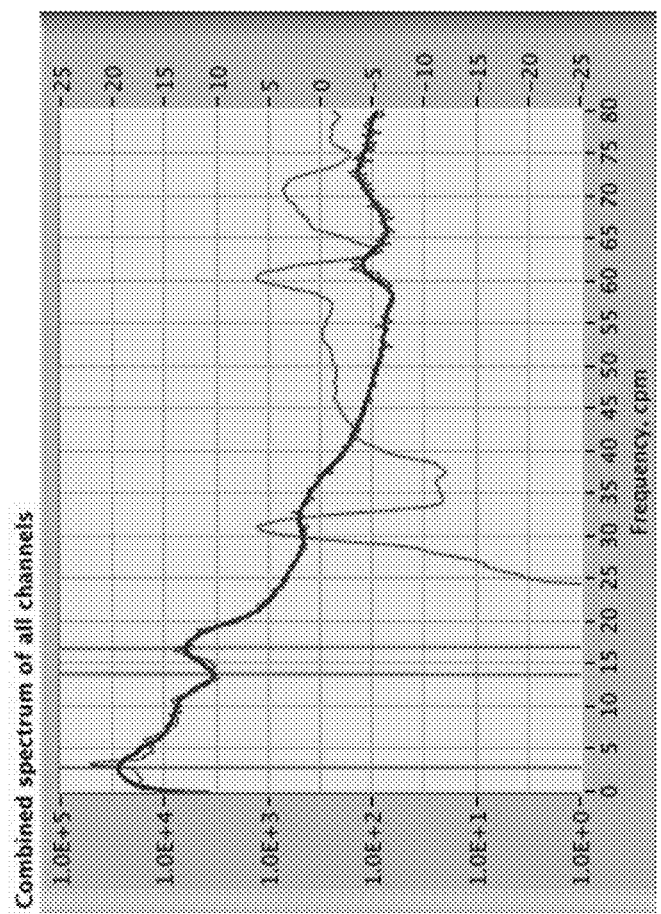

FIG. 34 shows a spectrum with a smoothed version superimposed thereon, and the derivative of the smoothed version. The spectrum is linked to the logarithmic scale on the left while the derivative uses the linear scale on the right. In this example, there is a small bump in the spectrum centered about 33 cpm that is not desirable for inclusion. The derivative in this plot is close to zero in the region 25 to 45 cpm, but only because the scale was chosen to show the entire extent. In FIG. 35, the vertical range is zoomed in and one can see that there is significant structure in the derivative in that region. In particular, the aforementioned bump produces a substantial positive and then negative going excursion in the derivative from 30 to 40 cpm. Conversely, the region from 40 to 55 cpm that is quiet in the spectrum has a derivative that is within −5 to 0. Thus, it can be seen that the derivative is a useful means of determining a region of interest that has the quietness characteristics desired in a normalization region.

Figure 36:
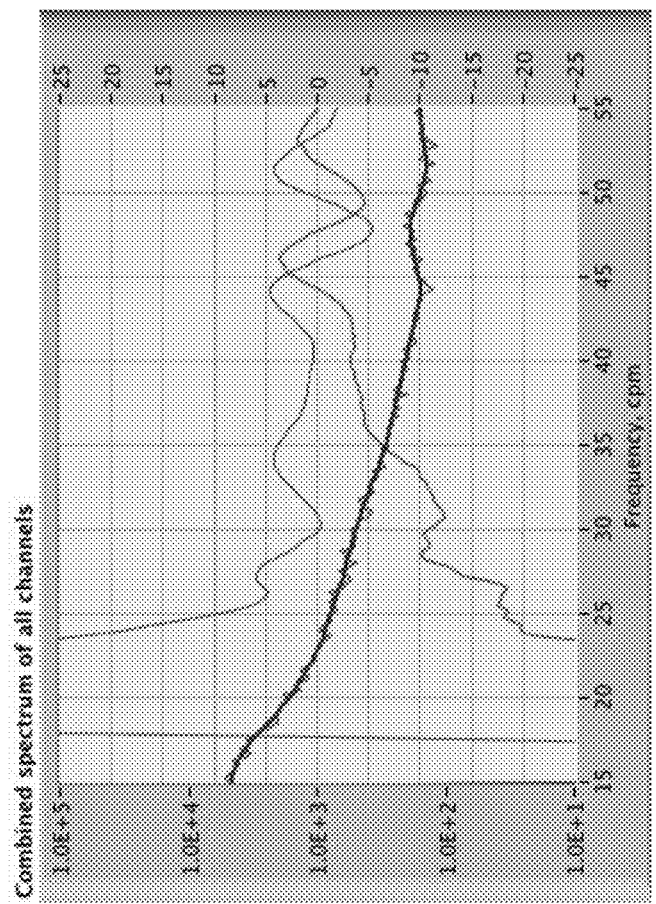
FIG. 36 shows a spectrum in blue, derivative in red, and second derivative ×10 in green.

FIG. 36 shows a data set that has the desired quietness characteristics in the region of interest from 25 to 45 cpm and which is representative of many other sets in terms of the general shape of the spectrum in the region. The derivative shown in red is within the range −20 to +2, while the second derivative shown in green is within the range 0 to 10. In the region of interest 35 to 45, the derivative is similar to the previous set of figures in that it is within −5 to 0, but from 25 to 35 cpm, the range is wider. This illustrates the value of creating a set of acceptable ranges that are local in the sense specified earlier, that is, apply only to a specific subset of the region of interest, based on known characteristics of data that is identified as acceptable. The algorithm effectively uses the information gleaned by human insight on a relatively small set of samples to apply in a uniform, automated way to large numbers of data sets.

In some embodiments, a normalization range or quiet section or region is automatically identified based on analysis of the raw data file or processed data file. For example, if a peak occurs at 31 cpm, an identified quiet section should be greater than 31 cpm, for example 35-50 cpm (as opposed to 25-45 cpm or 30-50 cpm). To compensate for different lengths and locations of quiet sections or normalization ranges, a similarly lengthened and located quiet section (e.g., 35-50 cpm) could be used in a reference data set for comparison and/or normalization. Alternatively or additionally, a quiet section or normalization range may be automatically identified, for example, based on a highest cpm known peak in the data, the quiet section or normalization range selected to automatically start thereafter, and then automatically compensating or normalizing the dataset based on this automatically identified quiet section or normalization range.

In some embodiments, a ratio of energy between an experimental or test dataset (e.g., from a patient) and a reference dataset for an exact cpm range may be used as a normalization factor. However, this may be skewed if the test or experimental data set has, in general, higher frequency events.

Another technique is to use raw data to determine a normalization value by determining a baseline signal level in the raw data (e.g., $95^{th}$ percentile) and comparing the baseline level to a reference baseline level and either normalizing based on a ratio of the experimental baseline level and the reference baseline level or by subtracting out the experimental baseline level from the raw dataset. However, this may also remove small peaks that may be obscured in the baseline level.

Alternatively or additionally, a band pass filter that encompasses the expected peak frequency ranges may be used to filter the transformed data after artifact removal.

The technique outlined allows a computer algorithm to select a region of interest that is appropriate for use in normalization of the data set the spectrum comes from. However, as can easily be seen in the figures, if one selects a region of interest at lower frequencies the integrated value will necessarily be higher than if the region of interest is predominantly at higher frequencies, and it will be less if the region is small than if the region is large. Thus, the normalization factor must take into account both the width of the region of interest selected, and the specific frequencies. This can be accomplished by mathematically modeling the expected or nominal spectrum and calculating the normalization factor in comparison only to the same section of the nominal spectrum.

Alternatively or additionally, normalization may be accomplished by training one or more machine learning models (e.g., deep neural network) with data from people categorized based on weight, body mass index, percent fat, or other parameter based on a loss function that minimizes the difference between the average signal levels after normalization between the two or more groups.

For example, a method may include: obtaining data from a skin-surface mounted electrode patch configured to sense and acquire EMG voltage signals; identifying one or more characteristics and/or patterns within a raw time series training data set derived from the EMG voltage signals from one or more groups of low body mass index (BMI) and high BMI individuals; training an ML model, for example a deep neural network, on the raw time series training data set, wherein the ML model may be developed based on a loss function that minimizes a difference between the average signal levels after normalization between the one or more groups; applying the machine learning model to a raw time series test data set, wherein the machine learning model is configured to: identify and apply the characteristics to normalize the raw time series data, and/or the spectrum data for test groups of low BMI and high BMI individuals. In some embodiments, the machine learning model may be trained to automatically identify a quiet range or normalization range, as described elsewhere herein, for a data set to normalize one or more groups.

A traditional approach when dealing with such large datasets with characteristics that contain repetitive or rhythmic signals is to summarize it in terms of its frequency parameters, through Fourier transforms and specifically a power series spectrum. Time is not necessarily eliminated from the analysis, nor is it desirable to do so, by use of the spectral approach as the spectra can be calculated in blocks over time.

There is a great deal of clinically useful information in the time dependent spectra, but extracting this information is challenging due to a number of factors, including (1) its vastness, (2) the presence of substantial noise relative to steady state levels and signal peaks, (3) the fact that the natural frequencies are very low and in many cases do not last for a large number of cycles, (4) the presence of multiple channels of data rather than just one, and (5) the interpretation of the levels and peak data patterns or structures as physiological markers.

This disclosure provides a novel approach to identifying the spectral peaks that occur due to rhythmic muscle activity in and around the gastrointestinal tract, determining the key characteristics of peak frequency, height, width, and duration, and assigning the discovered peaks to specific sources. Some of the challenges facing peak detection and quantification will now be enumerated.

Peak detection by an automated approach is of interest in many fields, each with their own set of challenges depending on the nature of the input data and the desired output. When the data have a high signal-to-noise ratio with a steady baseline and large peaks relative to the baseline, it can be easy to identify the location of peaks by simply setting a threshold value, and assuming that any data points above the threshold represent a peak or a portion thereof. However, even in this simplest of cases one must then identify the contiguous points that make up each peak, determine whether the peak center is the central point, the highest point, or some combination determined by, for example, applying filtering to the data. If one also wishes to determine the intrinsic height of the peak, and/or its width at half max, more work needs to be done and more choices are faced, for example with the type of filter to be applied to the data and the filter settings. If one also needs the area of the peak then the background level must be estimated, and the beginning and end points of the peak at its base, again leading to more algorithmic complexity and more choices.

When the data are very noisy and the peaks, when present, are not significantly higher than the background, detecting a peak becomes very challenging. If the background level varies substantially within a data set or even between data sets, more complexity is introduced. Measuring the parameters of the peaks becomes yet more challenging, and algorithms that attempt to do so must deal with many confounding situations. The frequency spectra of surface detected gastrointestinal myoelectric data are an example of a difficult situation for detecting and characterizing peaks.

When one is interested in the evolution over time of spectral peaks, for example to determine the start time and duration, and where the time scales are short relative to the frequencies involved such that there may be only tens of cycles or fewer of the rhythmic behavior that is under scrutiny, yet more complexity is involved and more choices arise. The obvious way of dealing with transient peaks is to break the data into time segments (with or without windowing and/or overlap). When the time segments are short, one has the best time resolution on determining the start time and duration, but if a large number of cycles is not contained in the time segment, the resolution suffers, and the signal-to-noise ratio is lower than it would be for a longer time segment with more cycles.

Figure 37:
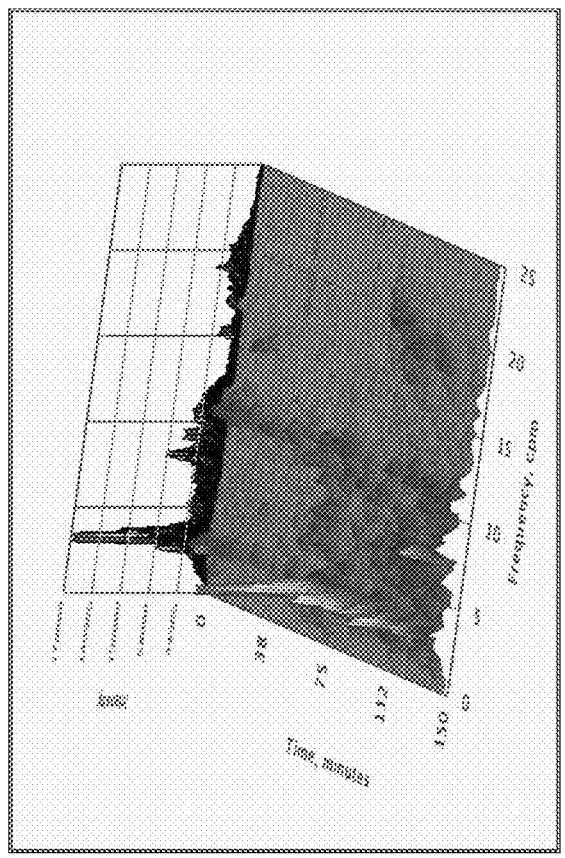
FIG. 37 shows a pseudo-3D "waterfall plot" of spectra taken from a 2.5 hour long data set, with time segments of 4 minutes.
Figure 38:
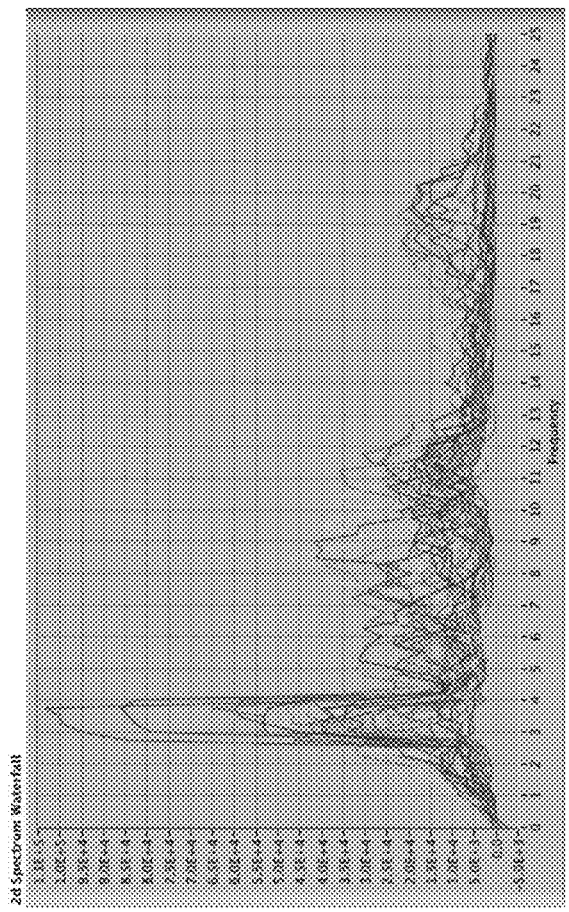
FIG. 38 shows the same data as those shown in FIG. 7 as a series of line plots rather than a pseudo-3D plot.

FIG. 37 shows a pseudo-3D "waterfall plot" of spectra taken from a 2.5 hour long data set, with time segments of 4 minutes. Time runs from rear to front in minutes while frequency runs from left to right in cycles per minute (cpm). Rhythmic behavior, representing periodic contractions of the smooth muscles in the walls of the digestive organs leads to peaks in the spectra. Peaks in FIG. 37 are quite clear to the eye for extended times at 3 and 10 cpm, and intermittently at several other frequencies. The peaks at 3 cpm are quite narrow and tall while those at the other frequencies are mostly broader and of lower amplitude on this scale. Any algorithm for peak detection based on a fixed threshold would either detect only the tallest peaks, or else would be subject to a great deal of noise if the thresholds were low enough to detect all of the peaks. This should be clear from FIG. 38, which shows the same data as a series of line plots rather than a pseudo-3D plot.

An improvement over the single value threshold, which is effective when there are multiple sets of data involved whether from multiple channels or multiple patients, is to use a threshold value that adapts to the data itself. One approach is to set a threshold based on a percentile ranking of all points in the set, for example at the 90th percentile. Other approaches in the same spirit can be employed as well, for example using a value set at 90% of the largest data point. This approach can be further improved by breaking the frequency range into several sub-ranges, and treating each sub-range separately, so that peaks that are larger in one sub-range do not eliminate the possibility of detecting peaks in other sub-ranges. One way of choosing sub-ranges is to select ones that represent the expected ranges for stomach, small intestine, and colon, approximately 2 to 4, 5 to 12, and 12 to 25 cpm, respectively. Alternatively, one can choose sub-ranges that individually surround each of the peaks previously observed. Since peaks can show up at different places for different patients, the sub-ranges can be allowed to overlap. Depending on the subsequent processing of the detected peaks, such overlap will need to be taken into account, say to avoid double counting of a peak on the border between two sub-ranges.

Figure 39:
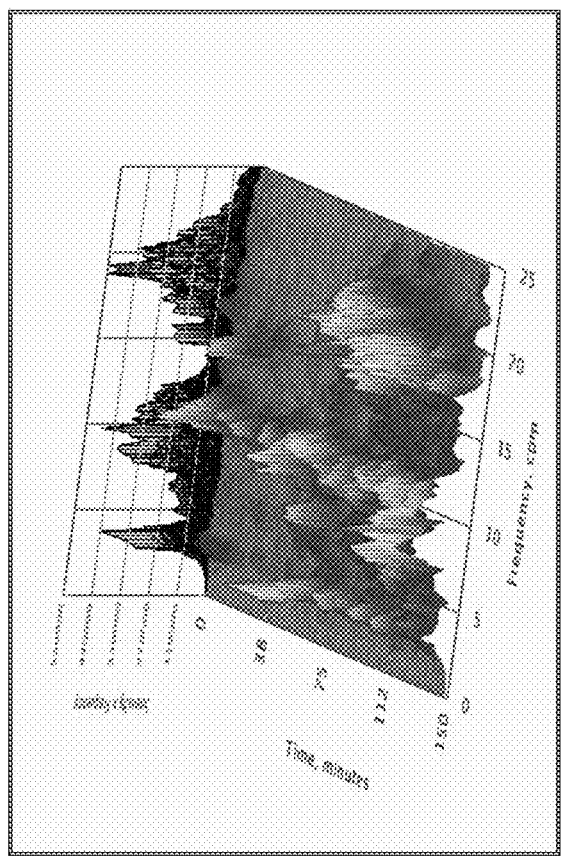
FIG. 39 shows the same data as in FIG. 7 but with frequency weighting applied.

Another way of adjusting to the fact that there can be peaks at different heights even in a sub-range, takes account of the fact that the amplitude of signals (peaks and background) in general tends to drop with frequency. To compensate for this, one can weigh the spectrum by the frequency. FIG. 39 shows the same data as in FIG. 37 but with frequency weighting applied. It can be seen that the peaks in this case are now all of similar amplitude, which can ease the task of determining a peak threshold.

In determining the height and area of a peak, it is necessary to account for the level of background, i.e., the amplitude that would obtain if the peak were not present. If this is not taken into account, and the peak is considered to start at an amplitude of zero, a bias will be introduced when comparing peaks. By way of an example, consider a first peak with amplitude 1 unit, and a second peak with amplitude 2 units, both on a background of 1 unit. The actual ratio of peak 2 to peak 1 is 2, but if the background is not taken into account the calculated ratio will be 3/2.

Given the example above, in some embodiments, a background shape is determined either from measurement at a location on the patient away from the GI tract, from measurement using an adjacent patch with no apparent peaks, from measurement using another channel on the same patch with no apparent peaks, or by fitting a general background shape (e.g., based on time when no peaks are present or on an adjacent channel), and then the background shape is subtracted from a particular patch spectrum to improve signal to noise ratio on the resulting peaks that represent gastrointestinal organ peaks. This method could be used as an alternative to other peak detection methods described elsewhere herein or used to enhance any of the peak detection methods described elsewhere herein. However, artifacts that appear as "real" gastrointestinal peaks may also be enhanced by this process. As such, in some embodiments, artifact removal is performed on the dataset before the background shape is subtracted from the dataset.

As with detecting peaks, determining the background level is something that is easy to do by eye, but much more challenging to do well by way of an automated algorithm. If the peaks are isolated, with large gaps between them, there are a number of approaches that can be employed such as averaging a set of points from the middle area between peaks, on either side of every peak, and using the average of the two sides. When the peaks are less clearly delineated, or when the background information is needed as part of the peak identification algorithm, a different approach is required. In the method provided herein, the background is estimated a priori by a mechanism analogous to that used in setting the peak threshold. A percentile rank value or percentage of range value is used as the background, the value being informed by analysis of previous data sets, and set on a sub-range specific basis, and depending on whether the spectrum is frequency weighted or not.

Having set peak detection thresholds, one can begin to identify valid peaks simply by noting what points exceed the threshold. One can also employ standard algorithms that provide additional discriminatory value such as those included in software packages such as LabVIEW or Matlab. If using such algorithms, it is necessary to provide setpoints that control the discriminants, and these can be incorporated into the full set of sub-range setpoints.

With the type of data found in myoelectric measurements of gastrointestinal motor activity, the peaks when present are often not much higher than background and not much greater than the typical noise level, yet it is desirable to identify and characterize all peaks. As a result of the low signal-to-noise ratio, the standard algorithms often return results that are driven by noise rather than by real peaks, and additional discrimination is needed to separate the valid signals from the noise. One can apply filtering to reduce the noise, but this tends to smear peaks and reduce their height, and therefore must be done in moderation, and to be optimal should be done on a sub-range specific basis as well.

Figure 40:
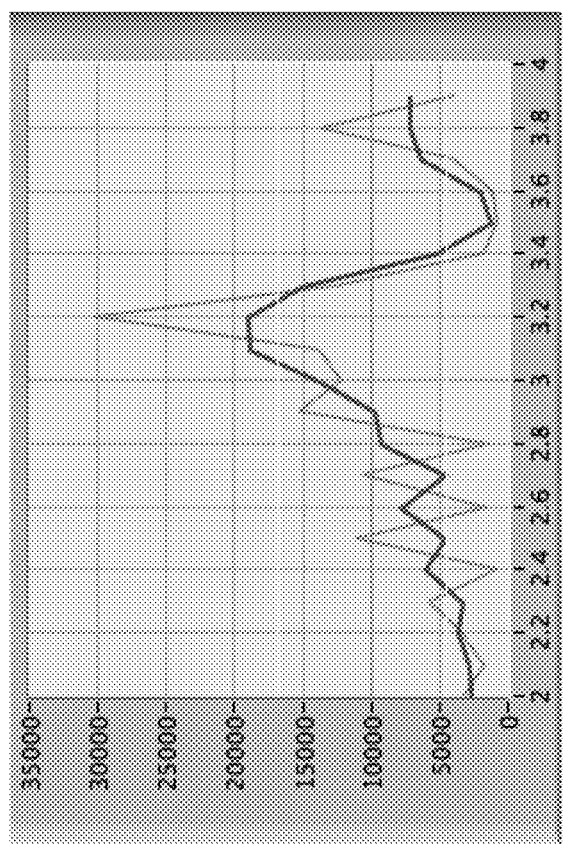
FIG. 40 shows a spectrum containing a single peak (in red) over a sub-range from 2 to 4 cpm, with filtered version in blue and cursors showing background level and peak threshold.

FIG. 40 shows a spectrum from a 4-minute time segment from the sub-range 2 to 4 cycles/min (cpm) with a relatively clear peak. From our empirical observations, in this frequency range, one peak from physiological sources can be expected, at most. The calculated spectrum is in red and a filtered version in blue. Horizontal yellow lines indicate the background level at about 5,000 units and the peak threshold at 17,000, both calculated based on the filtered values. This example shows that even when there are clear peaks, the analysis benefits from filtering and a threshold that reflects the data itself rather than a pre-determined absolute value.

Figure 41:
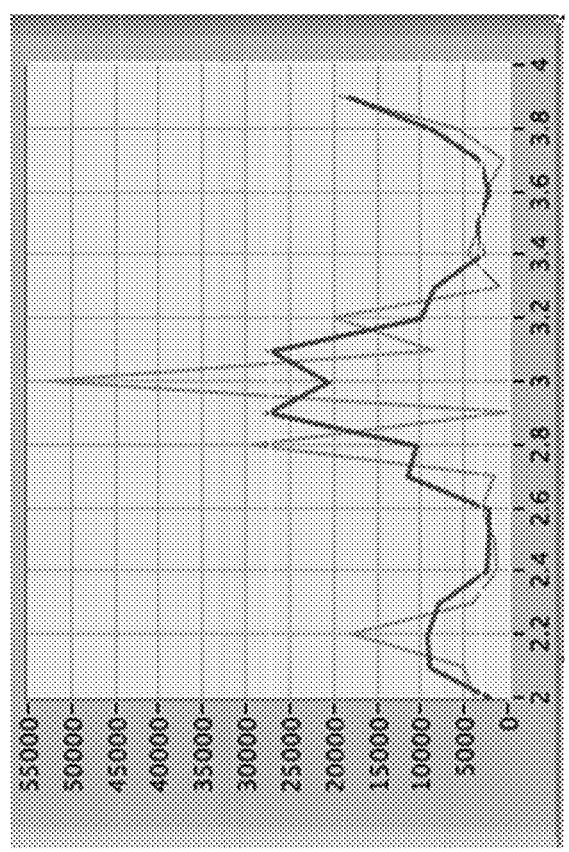
FIG. 41 shows a noisy spectrum leading to identification of 3 peaks.
Figure 42:
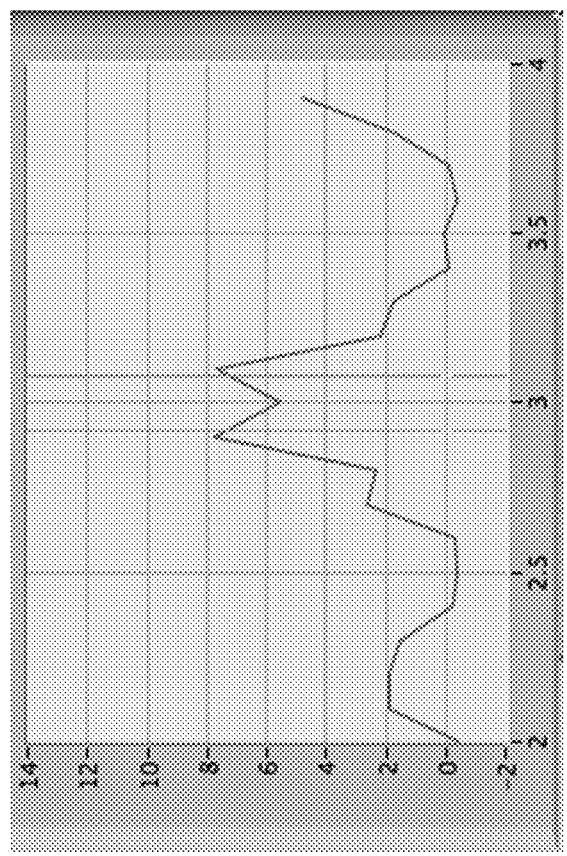
FIG. 42 shows the location of peaks identified in first phase of processing from FIG. 12 in net scaled amplitude data.

FIG. 41 is more complicated application of the described method; the data are very noisy, and although filtering reduces the variation, there are still multiple peaks above the threshold, in this case at 25,000 units. The identified peaks are shown in FIG. 42. A slightly higher threshold would lead to a single peak in this case, but in a large dataset such data complexity is common, and so the automated algorithm must have a mechanism to deal with it.

Therefore, as provided herein, a second phase of processing sets criteria for what is a valid peak and what is not, based on an approach that imposes "cuts" based on both numeric and logical values. Imposing cuts is intended as a general post-peak-identification process, not to be limited to the examples that follow. Use of cuts follows a straightforward process that makes it inherently extensible. Starting with the broad set of all candidate peaks initially identified, the cuts are imposed one by one, eliminating those candidates that do not meet the chosen criteria. The cut criteria can be either quantitative or logical (yes/no).

To illustrate the concept of cuts, FIG. 42 shows two candidate peaks identified by the first part of the automated algorithm that appear quite close together and can be reasonably assumed to be a single peak. The cut used to eliminate this behavior tests the separation between peaks against a setpoint value. If the peaks are further apart than the setpoint, they both are passed to the next test; but if they are closer than the setpoint, they are combined into a single peak, at a frequency determined either by a simple average or with an average weighted by the amplitude of each.

A second example of a cut concerns the degree to which the peak is isolated and requires the amplitude on either side to drop to a fraction of the peak height, typically one half but not necessarily so. Typically, but not exclusively, the values examined would be net values, that is, with the background subtracted.

A further example of a cut concerns the amplitude of the candidate peak. This can be applied in multiple ways, ensuring that there is a minimum value of absolute amplitude, net amplitude and/or scaled amplitude, where scaled amplitude is net amplitude divided by background thereby representing multiples of the background level.

A yet further example concerns peaks near the edge of the sub-range, where it can be required that the peak center, or half-max location, or similar parameter be at least a minimum distance from the edge.

Additional cuts can easily be imagined depending on the specific goal of the analysis, for example demanding there be only one peak, or that it be within a particular frequency range or amplitude range, or have a slope on either side within a specified range, and so forth.

The total amount of energy in a peak emanating from motor activity in a gastrointestinal organ over its duration is of interest in understanding the operation of the digestive system as it relates to motility events in the organ. To measure this total energy the total volume of the peak, height times width times duration, is calculated. Duration is thus an additional parameter that needs to be extracted from the spectrum. The inherent challenge in doing so for gastrointestinal myoelectric data concerns the fact that the waves are slow, as slow as 2 cycles per minute. When calculating a spectrum, the peak width depends on the number of cycles of activity included in the time series data. The fewer the cycles, the broader and shorter the peak, resulting in poorer resolution.

Figure 43:
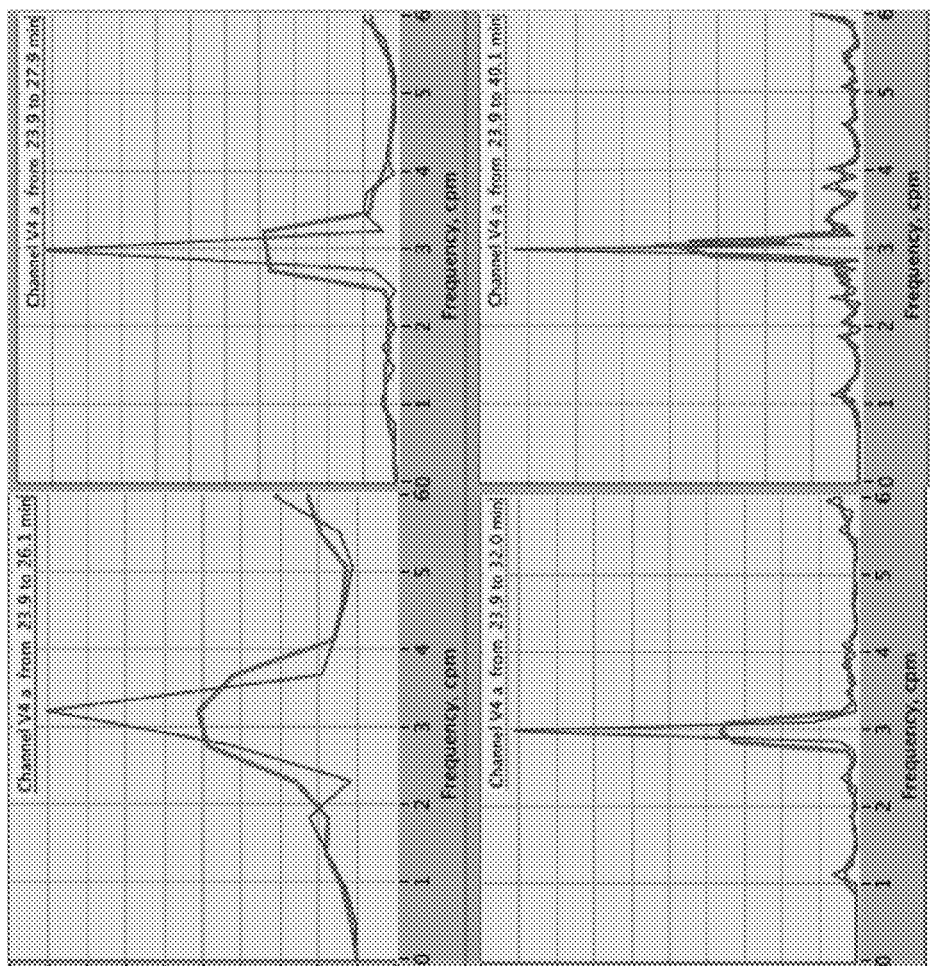
FIG. 43 shows spectral peaks from stomach motor activity at 3 cycles/min (cpm), using time segment lengths of 2, 4, 8 and 16 minutes, illustrating the increased resolution obtained with longer time periods. The blue line represents the raw spectrum; the red line is a version with Savitsky-Golay smoothing of rank 1 applied.

FIG. 43 is an example of a spectral peak using 2, 4, 8, and 16 minutes of data, illustrating how the resolution improves with longer time periods of data collection. Therefore, it is desirable to use longer time segments in the spectral analysis to obtain narrow tall peaks that can easily be identified. Unfortunately, the use of longer time segments to improve frequency resolution lowers the resolution in the time dimension. Longer time segments can also lead to a broader measured peak if the actual peak frequency is changing during the time period, as is known to occur with some of the gastrointestinal signals. It is thus advantageous to use an optimum time segment in trading off resolution in frequency vs. resolution in time.

To determine the peak start and end times, and thereby duration, one needs to identify the edges of the peak in the time dimension, analogously to what is done in the frequency dimension, for example, by finding the point at half-max above background at the leading and falling edges of the peak. An alternative approach, if what one is interested in is the total volume of the peak, is to ignore the rise and fall points and simply calculate the volume from beginning to end of the time segment using the height, full width and half maximum, and segment duration. The process of calculating the spectrum integrates over the length of the time segment, so a brief peak will simply show up as a smaller peak, and as long as it is detected, there will be no bias introduced by using the time segment length as the peak's duration.

As an approach to improving the ability to detect and measure the parameters of frequency peaks, an aspect of the current disclosure involves setting the time segment lengths adaptively. This can be accomplished by processing the data multiple times with different time segments, say 1, 2, 4, 8, and 16 minutes long, and then examining the peaks found to narrow down the likely start and end times, and further performing an analysis using a set of time segments that are based on the determined start and end times. Peaks can first be identified in any time segment, but the longer ones, in particular, have better signal-to-noise ratio for longer lasting peaks, and then the shorter time segments can be examined at the frequency of the found peak to determine when they begin and end. If the peak location is known, the selection criteria can be relaxed in the shorter time segments, using the rationale that it is easier to find something if you know that it is present.

Another approach is to use sliding time segments. The use and value of this can be understood by way of the following example. If there is a peak of duration 4 minutes and the chosen time segment length is 4 minutes, a high signal-to-noise ratio can be achieved if the time segment is synchronized with the peak's existence. However, in general, this will not be the case. Using a 4-minute segment and shifting so that it re-starts every minute allows for the algorithm to find the best setting with highest signal-to-noise ratio. This approach can be combined with the approach (previously noted) that identifies the start and end times of each peak, and then sets time segments exactly around those times, to obtain optimum signal-to-noise ratio.

Having identified a set of peaks and determined their parameters of frequency, height, width, and duration, one can calculate the volume of each peak which can then be used as a measure of motor activity in the relevant organ. As there will be multiple peaks coming and going over time, and at different frequencies, as well as over multiple channels of data, it is desirable to combine the volumes in some way to summarize the results in a smaller number of metrics. Further it is desirable to combine them in a way that reflects the frequency of the activity, as this is of physiological interest. The challenge of doing so is that the measured frequencies are not always tightly grouped and widely separated.

Figure 44:
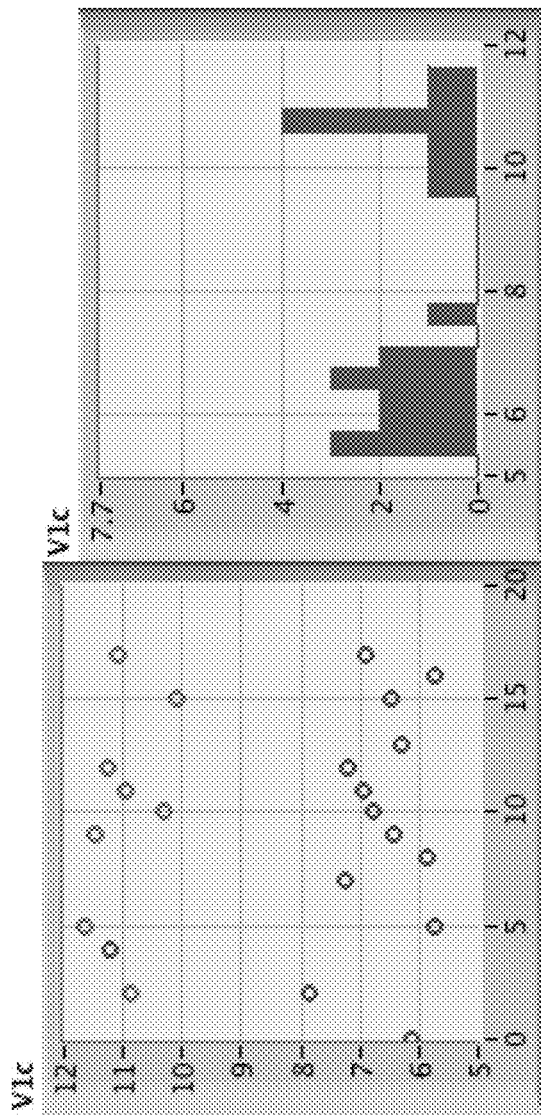
FIG. 44A shows data from time segments of 10 minutes and peak frequencies detected over time in 10 minutes.
FIG. 44B shows data from time segments of 10 minutes

FIG. 44A shows the frequencies detected per time segment and FIG. 44B shows their distribution in histogram form. In FIG. 44A, blue circles show the first peak detected while red indicates that a second peak has been detected in that time segment. The identified peak frequencies can be seen to form groups at around 6 and 11 cpm. Just as peak detection was used to determine the location and frequency of peaks in the spectra, peak detection can be used to find the location of significant groupings when the frequencies of detected peaks are made into a histogram. By so doing, peak groups can be identified, and individual peaks can be assigned to one group or another based on criteria such as which value they are closest to. Once groupings are assigned, total peak volumes can be calculated by adding all the volumes from each peak in the group.

Figure 55:
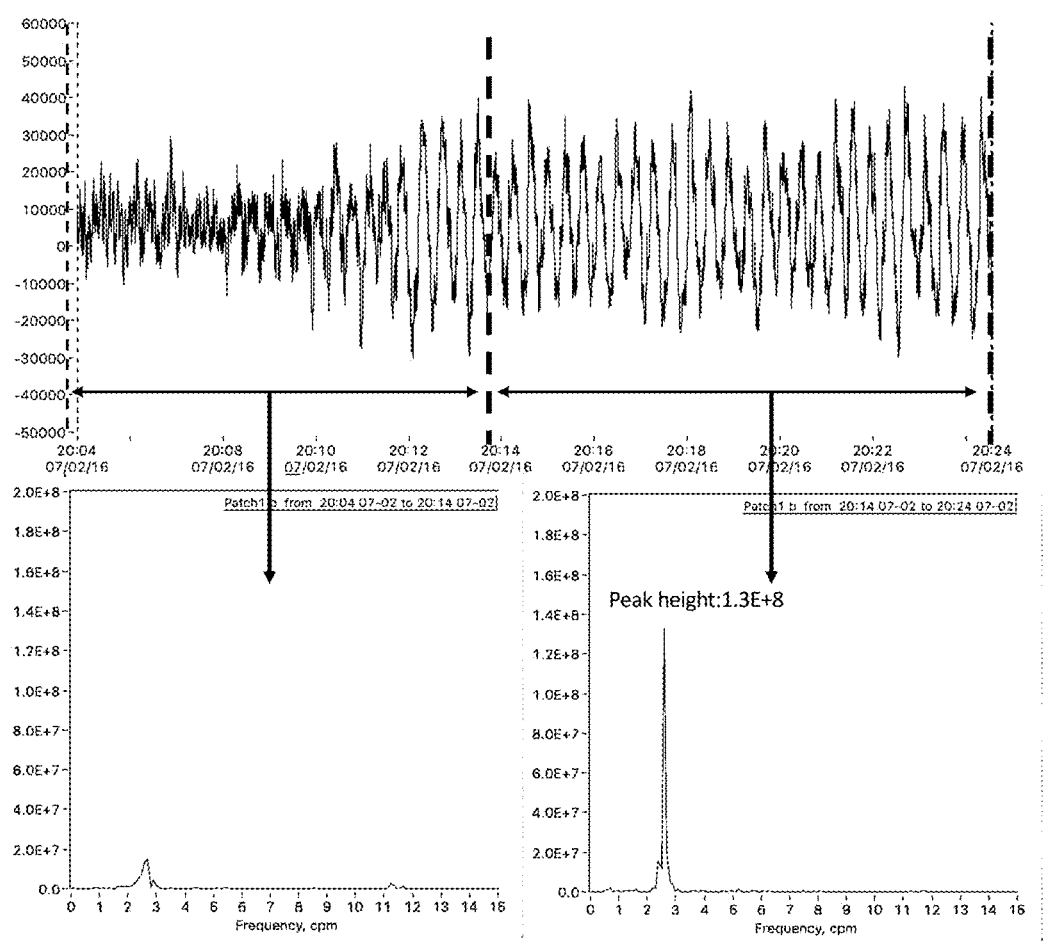
FIG. 55 shows examples of training data that include the raw time series gastrointestinal myoelectric data and the corresponding frequency spectrum computed for the first ten minutes and the subsequent ten minutes.
Figure 56:
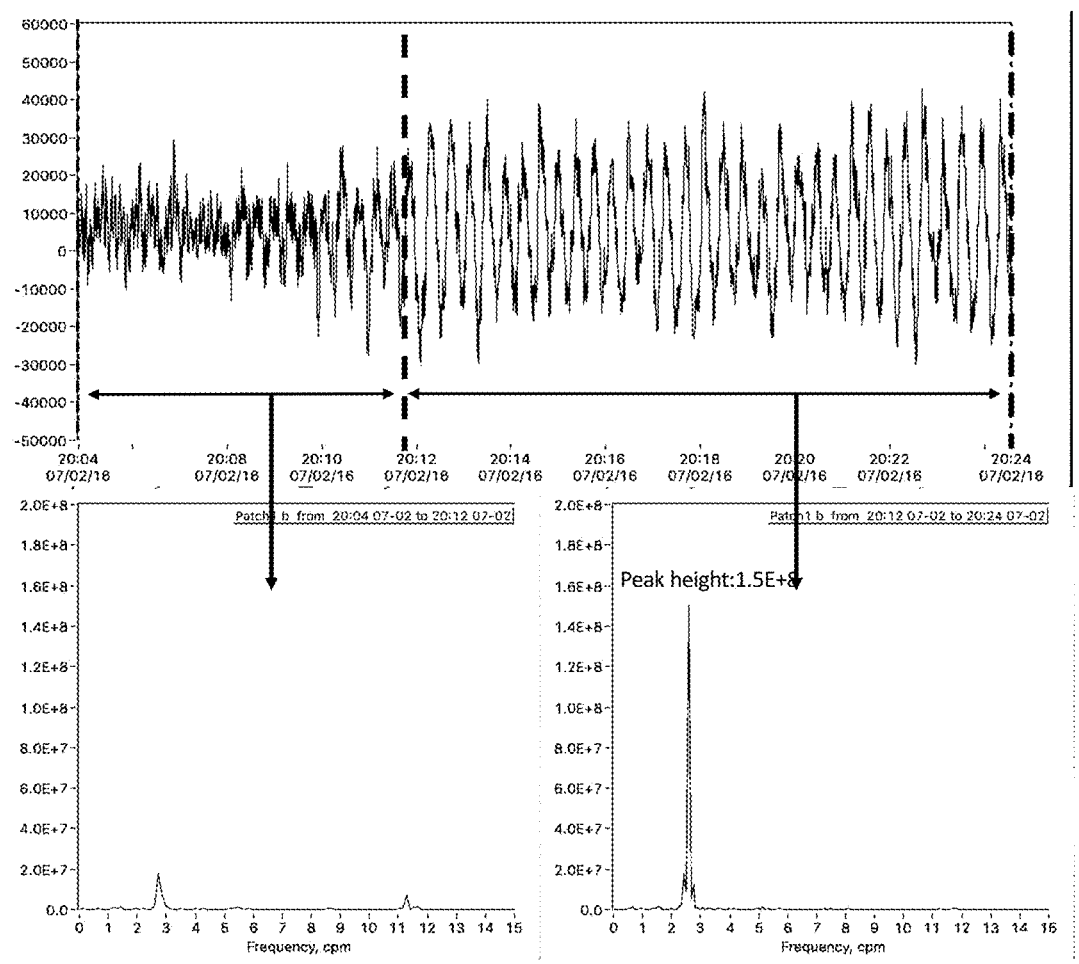
FIG. 56 shows the same raw time series gastrointestinal myoelectric data of FIG. 55 but using a time window for the second spectrum on the right includes time from the beginning of the rhythmic activity.

In some embodiments, after a peak is detected, one or more machine learning models may be trained to identify where each peak begins and ends to achieve a better overall reading on the strength and/or duration of the activity. The one or more machine learning models may be trained on a set of identified peaks derived from one or more analyses on one or more data sets described elsewhere herein. For example, the one or more machine learning models may be trained to identify what is in the raw data that creates a peak at higher amplitudes so it can see it when it first begins (at low amplitudes) and then when it ends. FIG. 55 shows examples of training data that include the raw time series gastrointestinal myoelectric data and the corresponding frequency spectrum computed for the first ten minutes and the subsequent ten minutes. FIG. 56 shows the same raw time series gastrointestinal myoelectric data; however the time windows chosen for calculation for the frequency spectrum are different. In this case, the time window for the second spectrum on the right includes time from the beginning of the rhythmic activity thus contributing to a higher peak amplitude.

Further, one or more machine learning models may be trained to recognize organ of origin for one or more signals or peaks based on one or more of: peak frequency, peak width, temporal behavior, other peaks nearby in time, and/or patterns seen across the entire spectrum such as a nocturnal shift in colon frequency.

In some embodiments, a series of bandpass filters may be used to sweep through the frequency range to create a data set to train one or more machine learning models on various peaks detected during each sweep with one of the series of bandpass filters. For example, the one or more machine learning models may be trained to determine which high amplitude sections comprise real peaks that can be attributed to an organ.

Figure 47:
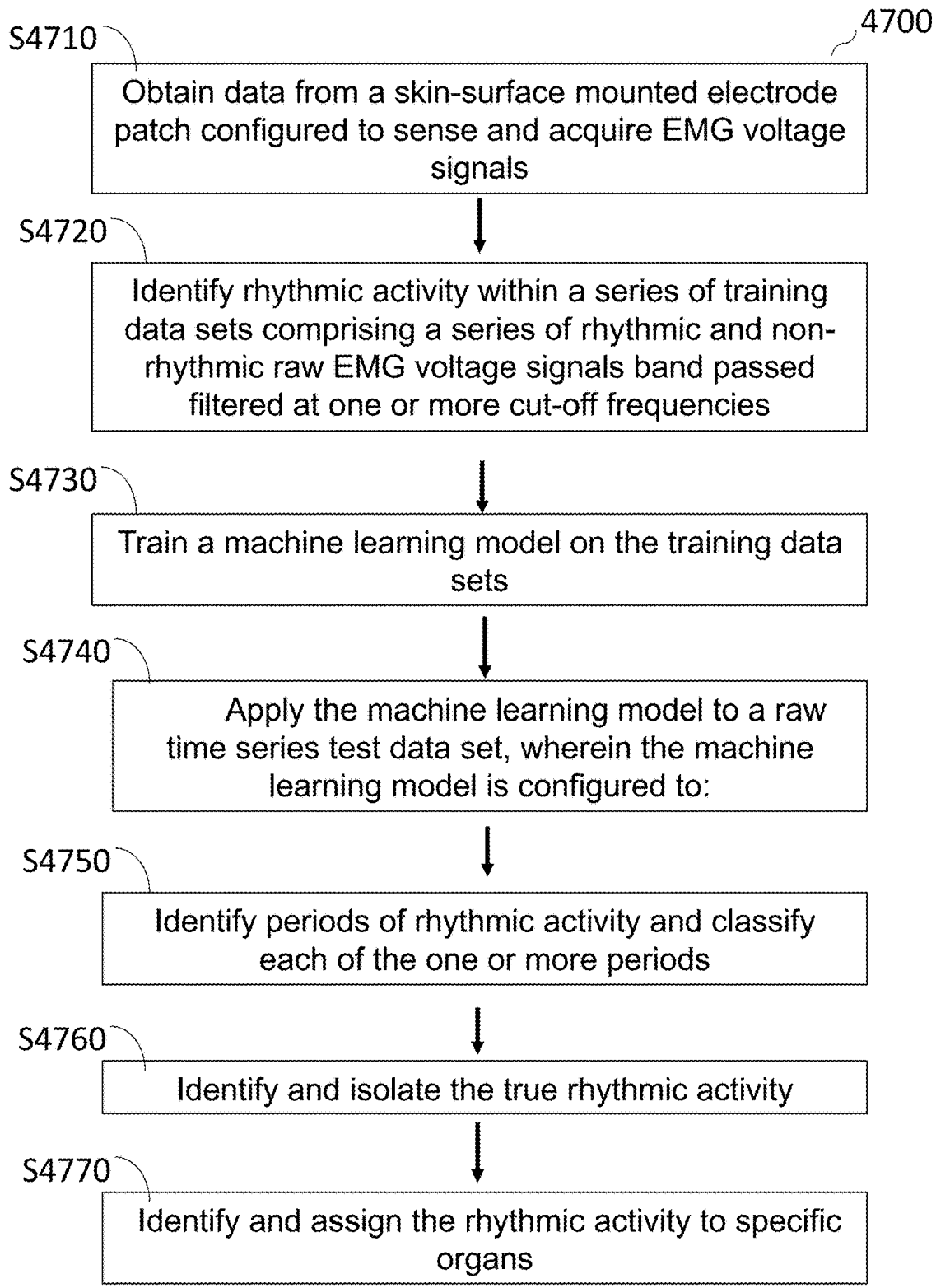
FIG. 47 shows a flow diagram of a method of extracting valid gastrointestinal tract EMG data from a raw time series data set using a machine learning model trained to, at least in part, identify true rhythmic gastrointestinal activity.

In one exemplary embodiment, as shown in FIG. 47, a method 4700 of extracting valid gastrointestinal tract EMG data from a raw time series data set acquired from a skin-surface mounted electrode patch includes: obtaining data from a skin-surface mounted electrode patch configured to sense and acquire EMG voltage signals at block S4710; identifying rhythmic activity within a series of training data sets comprising a series of rhythmic and non-rhythmic raw EMG voltage signals band passed filtered at one or more cut-off frequencies at block S4720; training a machine learning model on the identified rhythmic activity in the training data set at block S4730; and applying the machine learning model to a series of raw time series data at different bandpass filters at block S4740. The machine learning model is configured to: identify periods of rhythmic activity and classify and/or rank each of the one or more periods at block S4750; identify and isolate the true rhythmic activity from among all the rhythmic activity identified across the multiple levels based on one or more characteristics of the identified rhythmic activity at block S4760; and identify and assign the rhythmic activity to specific organs at block S4770.

In some embodiments, the identified rhythmic activity includes repeating oscillatory behavior with varying frequencies and/or peak to peak amplitudes.

In some embodiments, each identified rhythmic activity includes one or more characteristics comprising one or more of: a frequency or a combination of frequencies, a peak to peak amplitude, a noisiness/jitter around the rhythmic activity, or a combination thereof. In some such embodiments, the one or more characteristics are unique for each identified rhythmic activity.

In some embodiments, the one or more periods are classified and/or ranked based on a frequency or combination of frequencies, a peak to peak amplitude, a noisiness across the different bandpass filter levels, or a combination thereof.

In some embodiments, the specific organ may be a stomach, a small intestine, or a colon based on the one or more characteristics of the identified rhythmic activity.

In some embodiments of block S4720, cut-off frequencies could include multiple ranges. In one non-limiting scenario, the cut-off frequencies could be specific to organ frequencies of interest, for example, for the stomach, 2 to 4 cpm; small Intestine, 5 to 12 cpm; and colon, 12 to 28 cpm, along with an all-encompassing 0 to 28 cpm. Other scenarios could include generic ranges blind to organ type, for example 0 to 5 cpm, 5 to 10 cpm, 10 to 25 cpm, etc.)

In some embodiments, one or more machine learning models may be used for clinical or health status classification. For example, one or more machine learning models may be trained to determine or find patterns in signals before or after a patient recorded symptom or event (e.g., bowel movement, vomiting, pain, meals, medication, etc.), such patterns not occurring during normal activity or activity not associated with one or more patient recorded symptoms or events. Then, these data may be used to determine to which medications a patient may respond.

In some embodiments, a features extraction or clustering algorithm may be used to identify and rank parameters for predicting a status of a patient (e.g., recovery or non-recovery) after surgery or across different surgeries. Training data would be pre-labeled post-op recovery spectral data, peak data, and raw data for the recovery and non-recovery status.

FIG. 57 shows examples of training data that include peak frequency activity in the 2 to 4 cpm range corresponding to the stomach for patient's recovering from the Whipple surgery. Patients shown in the left column recovered early in contrast to the patients in the right column. As shown in FIG. 57, features may include, but are not limited to, a presence of clustering of peaks over time in a narrow band as a marker of recovery. One approach to extract the feature would be to calculate the standard deviation over time of the consecutive peak frequencies. Other features such as peak amplitudes and presence of other coordinated frequencies may also be extracted. Similarly, the training data may include activity in the small intestine and colon ranges depending upon the nature of the surgery.

Further, an overall spectrum, a motor activity strength in each organ, and/or an event response for different classes of disease may be assessed and/or compared to healthy controls and used to train a machine learning model. In some embodiments, the training data may further include clinical information (e.g., health history, demographics, event history, etc.), for example low stomach or small intestine activity in a gastroparesis patient. FIG. 58 shows examples of training data that include peak stomach activity in the 2 to 4 cpm range around a meal for healthy control subjects on the left column and patients with gastroparesis on the right column. The black vertical line at timepoint 0 represents the meal intake. While the healthy control subjects have a robust increase in their stomach activity following a meal, the patients with gastroparesis do not display a similar increase in stomach activity following a meal. Other non-limiting examples include low small intestine or colon activity in a constipation patient, unusually high activity in any organ in a diarrhea patient, and unusually low or high activity in any organ or a unique pattern of activity in a patient with an inflammatory condition such as Inflammatory Bowel Disease. The training data may also include patient response data to particular medications, so that during the testing or use phase, the ML model may be able to predict which medications a patient will respond to.

Figure 49:
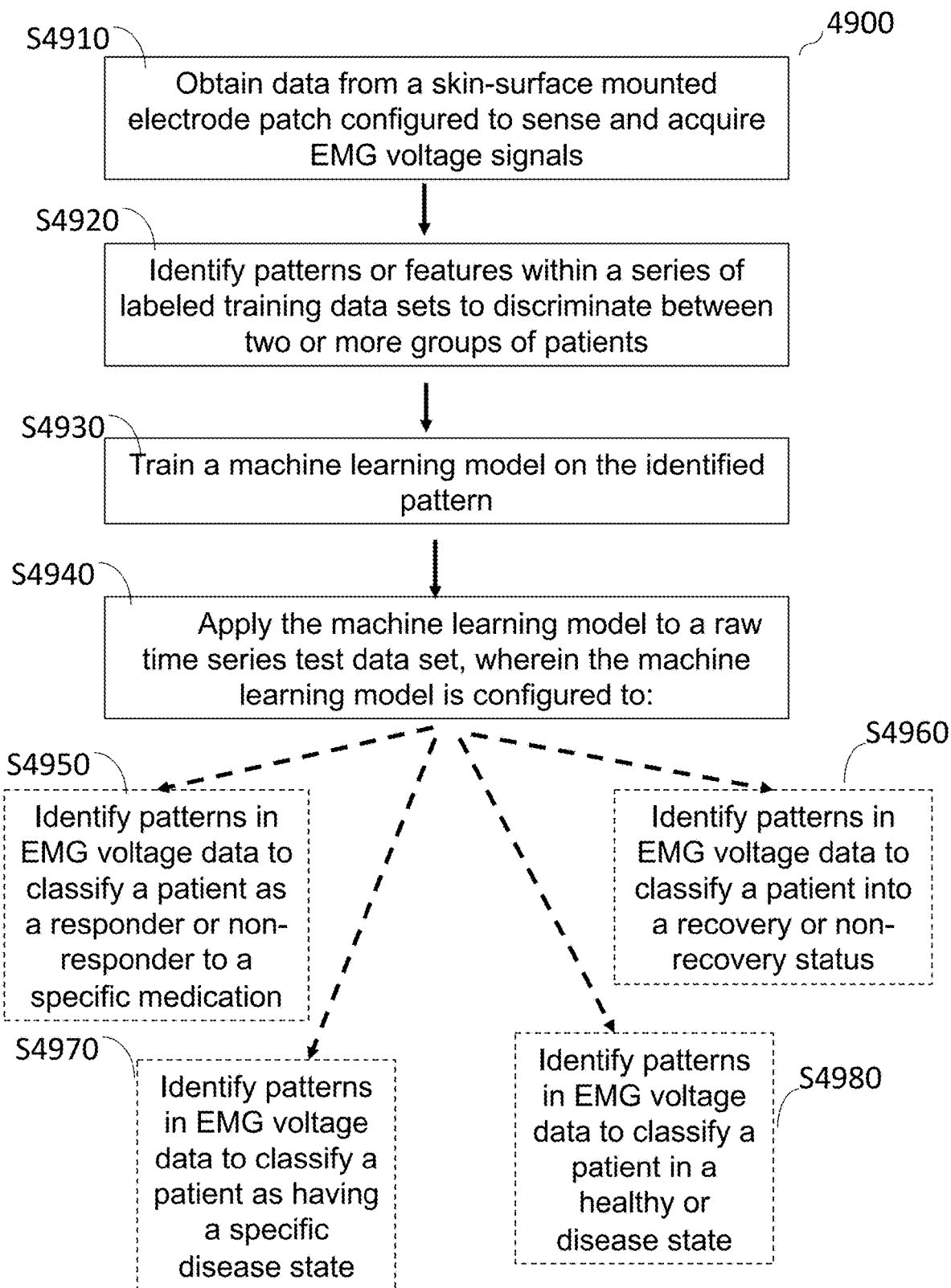
FIG. 49 shows a flow diagram of a method of extracting valid gastrointestinal tract EMG data from a raw time series data set using a machine learning model trained to, at least in part, identify patterns in EMG voltage data.

For example, as shown in FIG. 49, a method 4900 of extracting valid gastrointestinal tract EMG data from a raw time series data set acquired from a skin-surface mounted electrode patch includes: obtaining data from a skin-surface mounted electrode patch configured to sense and acquire EMG voltage signals at block S4910; identifying patterns and/or features within a series of labeled training data sets to discriminate between two or more groups of patients at block S4920; training a machine learning model on the identified pattern at block S4930; and applying the machine learning model to raw time series data, frequency spectrums, peak data, or a combination thereof at block S4940. The machine learning model is configured to perform any one or more of the following methods: identify patterns (e.g., in frequency, amplitude, strength, etc.) in the data (e.g., raw, spectrum, peak, etc.) associated with specific organs following surgery to classify a patient in a recovery or non-recovery status at block S4960; identify patterns (e.g., in frequency, amplitude, strength, etc.) in the data (e.g., raw, spectrum, peak, etc.) associated with specific organs and/or to specific events to classify a patient into a healthy or disease state at block S4980; identify patterns to classify a patient as a responder or non-responder to a specific medication at block S4950; and/or identify patterns and/or peak behavior as being representative of a specific disease state at block S4980.

In some embodiments, the identified data may include raw EMG voltage signals or sequentially computed frequency spectrums or frequency peaks of patients with recovered and non-recovered status following any given surgery. This could be similarly applied to identifying patterns and features within a series of labeled training data sets to discriminate between healthy and disease states in patients.

In some embodiments, patterns include, but are not limited to, weak or strong peak activity or combination of frequency and amplitudes across the organs following a surgery, before or after an event (e.g., surgery, medication, bowel movement, etc.). Examples of patterns include, but are not limited to, low stomach or small intestine activity in a gastroparesis patient; low small intestine or colon activity in a constipation patient; unusually high activity in any organ in a diarrhea patient; unusually low or high activity in any organ; or a unique pattern of activity in a patient with an inflammatory condition such as Inflammatory Bowel Disease.

Further, for example, an overall spectrum, a motor activity strength in each organ, and/or an event response for different classes of disease may be classified as compared to healthy controls. Additional clinical information may be included, for example, low stomach or small intestine activity in a gastroparesis patient, low small intestine or colon activity in a constipation patient, unusually high activity in any organ in a diarrhea patient, or unusually low or high activity in any organ or a unique pattern of activity in a patient with an inflammatory condition such as Inflammatory Bowel Disease.

In some embodiments, raw data, spectrum data, or peak data may be used to create an image that can then be used to train one or more machine learning models to recognize the image as being peaks attributable to certain organs or representative of a disease state.

In some embodiments, one or more machine learning models may be used to recognize peaks in time dependent spectra using existing detected peaks as training sets. This may be paired with one or more other machine learning models trained to detect artifacts and distinguish them from real peaks based on, for example, smoothness of rise and fall with and without a smoothing filter, etc.

Further for peak detection, to identify colon activity, nighttime colon activity may be used to assess a range of frequencies of the colon and/or how the frequency of the colon changes between day and night and/or over time. For example, a frequency of the colon may overlap with a frequency of the small intestine around 12 cpm. To determine whether this 12 cpm peak corresponds to the colon or the small intestine, the colon activity or frequency is assessed over time to determine how the signals change over time and to further distinguish its activity from that of other organs. In some embodiments, all the candidate colon peaks are identified and assessed for smoothness in time development between the peaks (e.g., by calculating derivatives, standard deviations, etc. over shorter periods of time, etc.). If there is smoothness between the candidate peaks, then the peaks are determined to be coming from the same GI organ.

After the data are extracted as outlined above, the extracted data may be presented as a percentile rank to assess gastric activity of an individual as compared to a population. The method includes calculating one or more volumes (i.e., integrating the peak to calculate volume) over time for one or more frequency ranges for each peak representing a GI organ, averaging or summing the one or more volumes over a time period, and comparing the summed or averaged volume to one or more summed or averaged volumes of one or more comparison groups in a percentile ranking system. For example, a comparison group may include healthy controls, one or more or a group of symptomatic patients, one or more groups that are known to have certain symptoms, one or more groups known to have received one or more treatments, one or more groups having a certain condition, etc.

Another method of determining gastrointestinal activity may include assessing a function of a specific organ over time. For example, the method includes detecting functional abnormalities in one or more gastrointestinal organs, for example delayed gastric emptying, gastroesophageal reflux disease, constipation, etc. In one, non-limiting example, a method for detecting delayed gastric emptying or gastroparesis is described herein. Gastroparesis is a motility disorder in which the stomach doesn't empty food as quickly as it should. When the GI tract works normally, the stomach should be 90% empty within four hours of eating a meal. When food sits in the stomach for a long time instead, it can cause pain, nausea and other uncomfortable symptoms. A method for detecting gastroparesis includes: identifying a gastric signal (e.g., at substantially 3 cpm), according to any of the methods described elsewhere herein; determining a first time that correlates to a maximum value (e.g., signal volume) of the signal and a second time after the first time which represents an emptying value; and comparing the emptying value to the maximum value to determine a degree of gastric emptying as a function of time. The degree of gastric emptying may be represented as a percentage, fraction, etc. Subsequent emptying values may be identified at n number of time points after the maximum value time point until the stomach is near or greater than 80% empty, near or greater than 85% empty, near or greater than 90% empty, near or greater than 95% empty, near or greater than 98% empty, etc.

For example, a comparison between the emptying value and the maximum value may show a decrease in gastric activity of 50%, 25%, 10%, etc. as a function of time. If the degree of gastric emptying is not greater than 90%+/−10% or less than 90%+/−10%, the method may include outputting an alert that the individual is likely to have gastroparesis.

Figure 45:
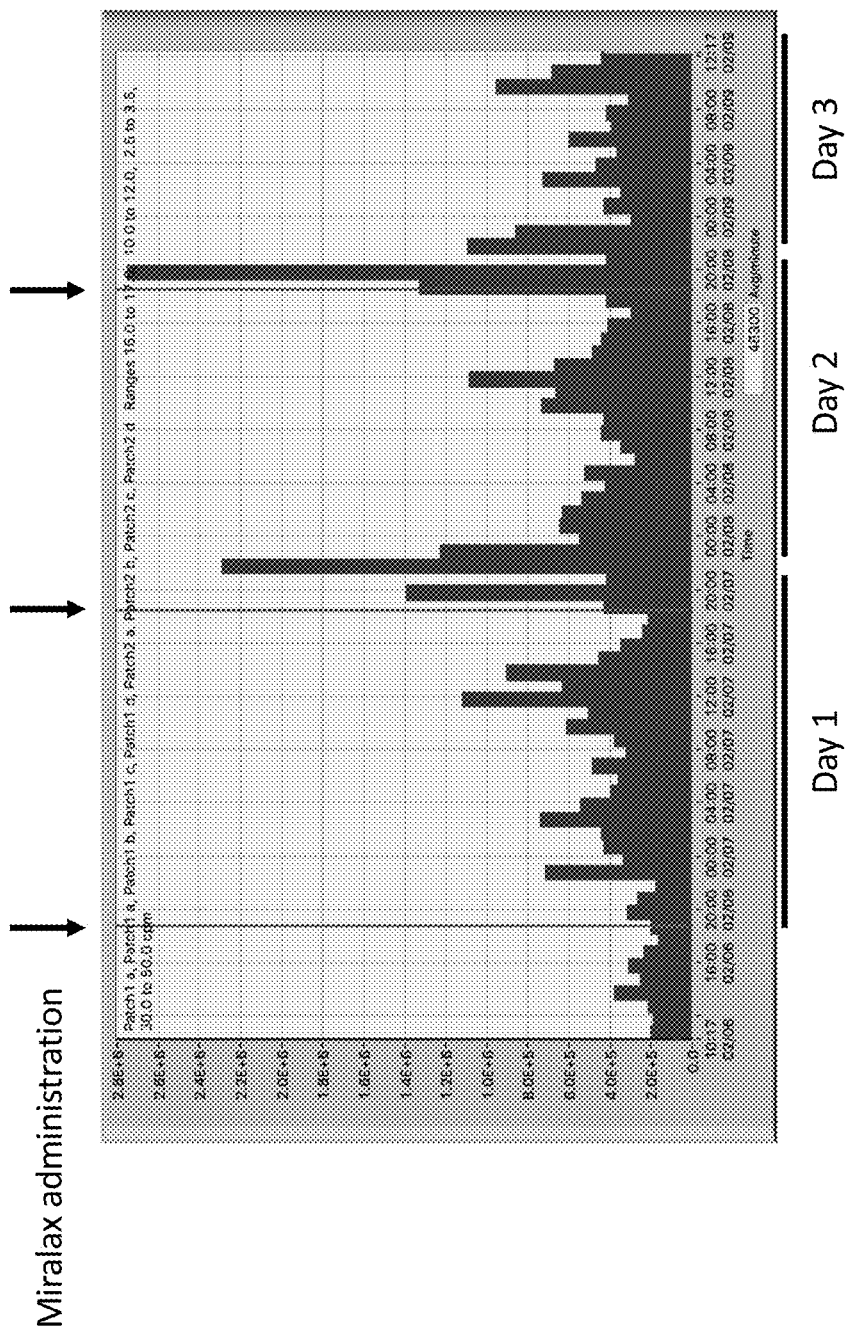
FIG. 45 shows a graph depicting spectral energy over a three-day Miralax treatment cycle.

In some embodiments, peak detection may be correlated with one or more user inputs of symptoms, treatments, conditions, etc. to correlate the daily measured gastrointestinal signals with daily patient experiences. The variability of each day may be exploited to determine how one or more GI organs respond to treatments, activities, etc.; to correlate symptoms with an activity observed in one or more GI organs, etc. For example, if a patient had pain one day and not another, peaks would be identified that differ between the two days to identify potential causes (e.g., which GI organ) for the experienced pain. To demonstrate the ability of the system to sense changes in GI activity overtime and correlate them to user inputs or events, FIG. 45 shows the spectral energy in the 15-17 cpm range over a three-day timeframe during a Miralax treatment cycle. As shown in FIG. 45, Miralax was administered to the patient on days 1, 2, and 3. Comparing Day 1 to Days 2 and 3, Miralax treatment showed a significant increase in spectral energy on Days 2 and 3.

Any one or more features of any embodiment disclosed herein can be combined with any one or more other features of any other embodiment, without departing from the scope of the present invention. Further, although the present inventions have been disclosed in the context of certain preferred embodiments and examples, it will be understood by those skilled in the art that the present inventions extend beyond the specifically disclosed embodiments to other alternative embodiments and/or uses and obvious modifications and equivalents thereof. Thus, it is intended that the scope of the present inventions herein disclosed should not be limited by the particular disclosed embodiments described above, but should be determined only by a fair reading of the claims that follow.

The systems and methods and variations thereof can be embodied and/or implemented at least in part as a machine configured to receive a computer-readable medium storing computer-readable instructions. The instructions are preferably executed by computer-executable components preferably integrated with the system and one or more portions of the processor. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions. As used in the description and claims, the singular form "a", "an" and "the" include both singular and plural references unless the context clearly dictates otherwise. For example, the term "peak" may include, and is contemplated to include, a plurality of peaks. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. A method of extracting, for a patient, valid gastrointestinal tract EMG data from a raw time series data set, the method comprising:
    positioning an electrode patch onto an abdominal region of the patient, the electrode patch including an array of bipolar electrode pairs that comprises two or more bipolar electrode pairs arranged orthogonally relative to each other, wherein the electrode patch is configured to sense and acquire EMG voltage signals;
    obtaining, by a processor, data from the electrode patch, wherein the electrode patch further comprises unique identifiers for individuating the obtained data;
    identifying, by the processor and based on at least one identifier of the unique identifiers, a plurality of artifacts within a first data set representing a raw time series training data set derived from the EMG voltage signals;
    performing, by the processor and using the first data set, artifact processing on a second data set representing a raw time series test data set associated with at least one gastrointestinal organ of the patient, the second data set being used to generate a clean time series data set by performing signal isolation based on subtraction of patterns of data that are ascribable to sources other than the valid gastrointestinal tract EMG data, wherein the artifact processing comprises:
        identifying one or more artifacts in the second data set and classifying each of the one or more artifacts in the second data set based on one or more characteristics of the one or more artifacts,
        eliminating, based at least in part on the classifying, the one or more identified artifacts from the second data set by tracking the one or more classified artifacts down to any of a zero-crossing or a midpoint-crossing point on either side of a high amplitude artifact, and
        replacing the one or more identified artifacts from the second data set with any of interpolated points or constant value points that span a gap across the eliminated one or more classified artifacts.

2. The method of claim 1, wherein:
    wherein the identified plurality of artifacts comprises a set of data points nominally centered on a point of largest excursion from an average value of zero-crossing and extending toward an average or zero-crossing; and
    identifying the plurality of artifacts within the first data set is based on a standard deviation of the set of data points.

3. The method of claim 2, wherein identifying the plurality of artifacts within the first data set is based on a percentile ranking of the set of points where a respective identified artifact within the first data set is identified as a structure having at least one data point in a percentile greater than a ninety eighth percentile of values associated with the set of points or less than a second percentile of values associated with the set of data points.

4. The method of claim 1, wherein identifying the plurality of artifacts within the first data set comprises offsetting data amplitude by an average amplitude, thereby creating a data set with an average value of zero.

5. The method of claim 1, wherein identifying the plurality of artifacts within the first data set comprises:
    tracking at least one artifact from the plurality of artifacts to a nearest zero-crossing or midpoint-crossing;
    selecting a first point on a first side nearest to the zero-crossing or midpoint-crossing;
    selecting a second point on a second side nearest to the zero-crossing or midpoint-crossing; and
    interpolating replacement points between the first point and the second point.

6. The method of claim 1, wherein identifying the plurality of artifacts within the first data set comprises tracking at least one of the plurality of artifacts to a nearest zero-crossing or midpoint-crossing, and setting all replacement points to a zero value or a midpoint value.

7. The method of claim 1, wherein identifying the plurality of artifacts within the first data set comprises using an adaptive threshold criterion based on statistical measures complementary to a statistical measure used to set a preliminary threshold.

8. The method of claim 1, wherein identifying the plurality of artifacts within the first data set comprises using characteristics of data shape that have been previously identified as artifactual.

9. The method of claim 8, wherein the data shape includes a rapid initial excursion followed by an approximately exponential decay with or without subsequent ringing.

10. The method of claim 1, wherein the one or more artifact from the second data set comprises an artifact amplitude lower than an amplitude of surrounding rhythmic activity.

11. The method of claim 1, wherein the plurality of artifacts in the first data set is identified and classified based on comparing the first data set to patterns or features associated with control data sets that include data associated with patients having one or more of a healthy gastrointestinal tract, a symptomatic gastrointestinal tract, a gastrointestinal tract receiving treatment, and a gastrointestinal tract with a defined gastrointestinal condition.

12. The method of claim 1, wherein the artifact processing on the second data set further comprises:
    detecting, in the second data set, one or more signal events leading up to a meal event, a bowel movement event, a pain event, or a sleep event;
    categorizing the one or more signal events based on at least one of:
        a signal weakness,
        a signal strength,
        an organ activity level of the at least one gastrointestinal organ of the patient,
        a change in the organ activity level; and
    classifying, based on the categorizing and the one or more signal events, a patient associated with the second data set into a disease state or a health state.

13. The method of claim 12, wherein the categorizing of the one or more signal events comprises identifying signal patterns associated with a specific organ to identify the organ activity level, the signal patterns including detected patterns of rest and detected patterns of non-rest.

14. The method of claim 1, wherein the second data set is obtained post-surgery on the at least one gastrointestinal organ of the patient, and the artifact processing on the second data set further comprises:
    identifying, in the second data set, signal patterns associated with the at least one gastrointestinal organ; and
    determining, based on signal patterns, a status for the patient, the status comprising a recovery state or a non-recovery state.

15. The method of claim 14, wherein:
    the one or more characteristics comprise amplitude, periodicity of variations, frequency of rapid variations, or envelope shape; and
    the signal patterns comprise patterns of signal frequency, signal amplitude, or signal strength.

16. The method of claim 1, further comprising:
    extracting, by the processor, one or more patterns of events from the clean time series data set; and
    determining, by the processor and based on the one or more patterns of events, diagnostic information representing rhythmic activity associated with the at least one gastrointestinal organ and how the rhythmic activity relates to one or more functional gastrointestinal disorders.

17. The method of claim 1, wherein the second data set represents a raw time series test data set associated with the at least one gastrointestinal organ of the patient, the second data set being obtained after the patient receives one or more treatments for the at least one gastrointestinal organ, and the artifact processing on the second data set further comprises:
    identifying, in the second data set, signal patterns associated with the at least one gastrointestinal organ; and
    determining, based on the signal patterns, a response to the one or more treatments for the at least one gastrointestinal organ.

18. A system for non-invasive monitoring of gastrointestinal tract activity, the system comprising:
    an electromyographic-sensing patch adapted for attachment to a skin surface of an abdominal region of a patient and including an array of bipolar electrode pairs comprising two or more bipolar electrode pairs arranged orthogonally relative to each other;
    a processor communicatively coupled to the electromyographic-sensing patch; and
    memory having instructions stored thereon, wherein execution of the instructions causes the processor to perform a method comprising:
        obtaining data from the electromyographic-sensing patch, the electromyographic-sensing patch being configured to sense and acquire EMG voltage signals,
        wherein the electromyographic-sensing patch comprises unique identifiers for individuating the obtained data;
        identifying, based on at least one identifier of the unique identifiers, a plurality of artifacts within a first data set representing a raw time series training data set derived from the EMG voltage signals;
        performing, using the first data set, artifact processing on a second data set representing a raw time series test data set associated with at least one gastrointestinal organ of the patient, the second data set being used to generate a clean time series data set by performing signal isolation based on subtraction of patterns of data that are ascribable to sources other than the valid gastrointestinal tract EMG data, wherein the artifact processing comprises:
            identifying one or more artifacts in the second data set and classifying each of the one or more artifacts in the second data set based on one or more characteristics of the one or more artifacts,
            eliminating, based at least in part on the classifying, the one or more identified artifacts from the second data set by tracking the one or more classified artifacts down to any of a zero-crossing or a midpoint-crossing point on either side of a high amplitude artifact, and
            replacing the one or more identified artifacts from the second data set with any of interpolated points or constant value points that span a gap across the eliminated one or more classified artifacts.

19. The system of claim 18, wherein the electromyographic-sensing patch further comprises a circuit board having a battery and a second processor configured to receive the EMG voltage signals from the array of bipolar electrode pairs and transmit data to a processor on a remote computing device or a computing device networked to the processor.

20. The system of claim 18, wherein the second data set represents a raw time series test data set associated with the at least one gastrointestinal organ of the patient, the second data set being obtained after the patient receives one or more treatments for the at least one gastrointestinal organ, and the artifact processing on the second data set further comprises:
   identifying, in the second data set, signal patterns associated with the at least one gastrointestinal organ; and
   determining, based on the signal patterns, a response to the one or more treatments for the at least one gastrointestinal organ.

21. The method of claim 1, wherein the individuating of the obtained data is performed according to each unique identifier per a location on a skin surface of the abdominal region relative to an underlying gastrointestinal tract region of the patient.

\* \* \* \* \*